US010239936B2

(12) United States Patent
Cooper et al.

(10) Patent No.: US 10,239,936 B2
(45) Date of Patent: Mar. 26, 2019

(54) METHODS AND COMPOSITIONS RELATED TO SOLUBLE MONOCLONAL VARIABLE LYMPHOCYTE RECEPTORS OF DEFINED ANTIGEN SPECIFICITY

(71) Applicant: The UAB Research Foundation, Birmingham, AL (US)

(72) Inventors: Max D. Cooper, Atlanta, GA (US); Brantley R. Herrin, Decatur, GA (US); Matthew N. Alder, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/052,986

(22) Filed: Feb. 25, 2016

(65) Prior Publication Data

US 2016/0376348 A1 Dec. 29, 2016

Related U.S. Application Data

(63) Continuation of application No. 12/375,804, filed as application No. PCT/US2007/074620 on Jul. 27, 2007, now abandoned.

(60) Provisional application No. 60/835,033, filed on Aug. 2, 2006.

(51) Int. Cl.
| | |
|---|---|
| *A61K 39/40* | (2006.01) |
| *C07K 16/12* | (2006.01) |
| *C07K 16/10* | (2006.01) |
| *C07K 16/34* | (2006.01) |

(52) U.S. Cl.
CPC ...... *C07K 16/1278* (2013.01); *C07K 16/1018* (2013.01); *C07K 16/1063* (2013.01); *C07K 16/34* (2013.01); *C07K 2317/14* (2013.01); *C07K 2317/20* (2013.01); *C07K 2317/33* (2013.01); *C07K 2317/35* (2013.01); *C07K 2317/76* (2013.01)

(58) Field of Classification Search
None
See application file for complete search history.

(56) References Cited

U.S. PATENT DOCUMENTS

| 6,521,448 B1 | 2/2003 | Edge et al. |
| 6,903,201 B2 | 6/2005 | Padigaru et al. |
| 2002/0025554 A1 | 2/2002 | Khodadoust |
| 2003/0175733 A1 | 9/2003 | Kirst et al. |
| 2012/0189640 A1 | 7/2012 | Cooper et al. |

FOREIGN PATENT DOCUMENTS

| EP | 2049564 | 4/2009 |
| WO | 2006083275 | 8/2006 |
| WO | 2008016854 | 2/2008 |

OTHER PUBLICATIONS

U.S. Appl. No. 12/375,804 , "Final Office Action", dated Sep. 10, 2013, 10 pages.
U.S. Appl. No. 12/375,804 , "Final Office Action", dated Aug. 25, 2015, 13 pages.
U.S. Appl. No. 12/375,804 , "Non Final Office Action", dated Oct. 28, 2014, 10 pages.
U.S. Appl. No. 12/375,804 , "Office Action", dated Dec. 7, 2012, 9 pages.
Acton et al., "Bactericidal antibody response in the Pacific hagfish, *Eptatretus stoutii*", Infect. Immun. 4:160-6 (1971).
Acton et al., "Induced Bactericidal Response in the Hagfish", J. Bacteriol. 99:626-8 (1969).
Adler et al., "Diversity and function of adaptive immune receptors in a jawless vertebrate", Science, vol. 310, Dec. 23, 2005, pp. 1970-1973.
Alder et al., "Antibody responses of variable lymphocyte receptors in the lamprey", Nature immunology 9.3 (2008): 319-327.
Anders et al., "Signaling danger: toll-like receptors and their potential roles in kidney disease", Journal of the American Society of Nephrology 15.4 (2004): 854-867.
Anderson et al., "Evolution of hematopoisesis: Three members of the PU.1 transcription factor family in a cartilaginous fish, *Raja eglanteria*", Proc. Natl. Acad. Sci. USA 98:553-8 (2001).
Ardavín et al., "Ultrastructure and changes during metamorphosis of the lympho-hemopoietic tissue of the larval anadromous sea lamprey *Petromyzon marinus*", Developmental & Comparative Immunology 11.1 (1988): 79-93.
AU2013242811 , Patent Examination Report No. 1 for Australian Patent Application No. 2013242811 dated Jun. 15, 2015.
Azumi et al., "Genomic analysis of immunity in a Urochordate and the emergence of the vertebrate immune system:"waiting for Godot"", Immunogenetics 55.8 (2003): 570-581.
Beckman , "Jawless Fish Have Form of Adaptive Immunity", Science 310.5756 (2005): 1892-1893.
Bell et al., "Leucine-rich repeats and pathogen recognition in Toll-like receptors.", Trends, Immunol, vol. 24, No. 10, 2003, pp. 528-533.
Beutler , "Innate immunity: an overview", Molecular immunology 40.12 (2004): 845-859.
Binz et al., "High-affinity binders selected from designed ankyrin repeat protein libraries", Nature biotechnology 22.5 (2004): 575-582.
Boffa et al., "Immunoglobulins and transferring in marine lamprey sera", Nature 214:700-2 (1967).
Bottaro et al., "S region transcription per se promotes basal IgE class switch recombination but additional factors regulate the efficiency of the process", The EMBO Journal 13.3 (1994): 665.

(Continued)

Primary Examiner — Jana A Hines
Assistant Examiner — Khatol S Shahnan Shah
(74) Attorney, Agent, or Firm — Kilpatrick Townsend & Stockton, LLP

(57) ABSTRACT

Disclosed are compositions and methods related to variable lymphocyte receptors (VLRs). More particularly, disclosed are a variety of antigen specific polypeptides, including soluble, monoclonal, and multivalent forms, as well as methods of using the polypeptides, antibodies that bind the antigen specific polypeptides, and nucleic acids, vectors and expression systems that encode the polypeptides. Antigen specific polypeptides that selectively bind pathogens, like anthrax, and carbohydrates, like blood group determinants, are specifically disclosed.

3 Claims, 23 Drawing Sheets

Specification includes a Sequence Listing.

(56) References Cited

OTHER PUBLICATIONS

Boydston et al., "Orientation within the exosporium and structural stability of the collagen-like glycoprotein BclA of Bacillus anthracis", Journal of bacteriology 187.15 (2005): 5310-5317.
Bryan et al., "Polymorphic microsatellite markers for the land-locked sea lamprey, Petromyzon marinus", Conservation Genetics 4.1 (2003): 113-116.
Canadian Application No. 2,659,574 , "Office Action", dated Oct. 16, 2014, 3 pages.
Canadian Application No. 2,659,574 , "Office Action", dated Jul. 26, 2013, 4 pages.
Canadian Application No. 2,659,574 , "Office Action", dated Nov. 26, 2015, 4 pages.
Chamaillard , "Nods, Nalps and Naip: Intracellular regulators of bacterial-induced inflammation", Cellular microbiology 5.9 (2003): 581-592.
Cooper , "Ammocoete lymphoid cell populations in vitro", 4th Leukocyte Culture Conference. OR McIntyre (Ed). New York Appleton Century-Crofts. 1971.
Cooper et al., "The evolution of adaptive immune systems", Cell 124.4 (2006): 815-822.
De Bouteiller et al., "Recognition of double-stranded RNA by human toll-like receptor 3 and downstream receptor signaling requires multimerization and an acidic pH", Journal of Biological Chemistry 280.46 (2005): 38133-38145.
Donelson , "Antigenic variation and the African trypanosome genome", Acta tropica 85.3 (2003): 391-404.
Eason et al., "Mechanisms of antigen receptor evolution", Seminars in immunology. vol. 16. No. 4. Academic Press, 2004.
European Application No. 07813487.1 , Extended Search Report and Written Opinion dated Apr. 16, 2012 in related European Patent Application No. 07813487.1.
European Application No. 07813487.1 , "Office Action", dated Apr. 15, 2016, 4 pages.
European Application No. 07813487.1 , "Office Action", dated Nov. 18, 2014, 9 Pages.
Finstad et al., "Evolution of the immune response. Ii. Morphologic studies on the origin of the thymus and organized lymphoid tissue", Laboratory investigation; a journal of technical methods and pathology 13 (1964): 490-512.
Finstad et al., "The evolution of the immune response: III. immunologic responses in the lamprey", The Journal of experimental medicine 120.6 (1964): 1151-67.
Flajnik , "Comparative analyses of immunoglobulin genes: surprises and portents", Nature Reviews Immunology 2.9 (2002): 688-698.
Flajnik et al., "Comparative genomics of the MHC: glimpses into the evolution of the adaptive immune system", Immunity 15.3 (2001): 351-362.
Flajnik et al., "Evolution of innate and adaptive immunity: can we draw a line?", Trends in immunology 25.12 (2004): 640-644.
Forey et al., "Agnathans and the origin of jawed vertebrates", Nature 361:129-134 (1993).
Fujii et al., "A histological and electron-microscopic study of the cell types involved in rejection of skin allografts in ammocoetes", Cell and tissue research 231.2 (1983): 301-312.
Fujii , "Electron microscopy of the leucocytes of the typhlosole in ammocoetes, with special attention to the antibody-producing cells", Journal of morphology 173.1 (1982): 87-100.
Fujii et al., "Immunity in lamprey I. Production of haemolytic and haemagglutinating antibody to sheep red blood cells in Japanese lampreys", Developmental & Comparative Immunology 3 (1979): 441-451.
Fujii et al., "Immunity in lamprey II. Antigen-binding responses to sheep erythrocytes and hapten in the ammocoete", Developmental & Comparative Immunology 3 (1979): 609-620.
Fujii et al., "Immunity in lamprey III. Occurrence of the complement-like activity", Developmental & Comparative Immunology 5.2 (1981): 251-259.
Good et al., "The biology of lampreys. II", Immunology (Eds Hardisty, M.V. & Potter, I.C.) 405-432 (Academic Press, London 1972).
Grimholt, et al., "MHC polymorphism and disease resistance in Atlantic salmon (*Salmo salar*); facing pathogens with single expressed major histocompatibility class I and class II loci", Immunogenetics 55.4 (2003): 210-219.
Hagen et al., "The immune response in adult sea lamprey (*Petromyzon marinus* L.): the effect of temperature", Comparative Biochemistry and Physiology Part A: Physiology 82.1 (1985): 207-210.
Haire et al., "Members of the Ikaros gene family are present in early representative vertebrates", The Journal of Immunology 165.1 (2000): 306-312.
Hamrick et al., "Antigenic variation of gonococcal pilin expression in vivo: analysis of the strain FA1090 pilin repertoire and identification of the pilS gene copies recombining with pilE during experimental human infection", Microbiology 147.4 (2001): 839-849.
Hein et al., "Processing of switch transcripts is required for targeting of antibody class switch recombination", The Journal of experimental medicine 188.12 (1998): 2369-2374.
Herrin et al., "Structure and specificity of lamprey monoclonal antibodies", Proceedings of the National Academy of Sciences 105.6 (2008): 2040-2045.
Hutchings et al., "Indirect sandwich ELISA for antigen detection of African swine fever virus: Comparison of polyclonal and monoclonal antibodies", Feb. 1, 2006, 213-217 pages.
Ikezawa , "Glycosylphosphatidylinositol (GPI)-anchored proteins", Biological and pharmaceutical bulletin 25.4 (2002): 409-417.
Jones et al., "Plant innate immunity—direct and indirect recognition of general and specific pathogen-associated molecules", Current opinion in immunology 16.1 (2004): 48-62.
Japanese Application No. 2009-522978 , "Office Action", dated Dec. 24, 2013, 9 pages.
Kajava , "Structural diversity of leucine-rich repeat proteins", Journal of molecular biology 277.3 (1998): 519-527.
Kasahara et al., "On the origins of the adaptive immune system: novel insights from invertebrates and cold-blooded vertebrates", Trends in immunology 25.2 (2004): 105-111.
Kaufman , "The origins of the adaptive immune system: whatever next?", Nature immunology 3.12 (2002): 1124-1125.
Kilarski et al., "The presence of plasma cells in the lamprey (*Agnatha*)", Developmental & Comparative Immunology 5.2 (1981): 361-366.
Kim et al., "Structural diversity of the hagfish variable lymphocyte receptors", Journal of Biological Chemistry 282.9 (2007): 6726-6732.
Kobe et al., "The leucine-rich repeat as a protein recognition motif", Current opinion in structural biology 11.6 (2001): 725-732.
Kobe et al., "The leucine-rich repeat: a versatile binding motif", Trends in biochemical sciences 19.10 (1994): 415-421.
Kumar et al., "MEGA3: integrated software for molecular evolutionary genetics analysis and sequence alignment", Briefings in bioinformatics 5.2 (2004): 150-163.
Laird et al., "50 million years of chordate evolution: Seeking the origins of adaptive immunity", Proceedings of the National Academy of Sciences 97.13 (2000): 6924-6926.
Landmann et al., "CD14, new aspects of ligand and signal diversity", Microbes and infection 2.3 (2000): 295-304.
Linthicum et al., "Immunologic responses of Pacific hagfish III. Serum antibodies to cellular antigens", The Journal of Immunology 105.4 (1970): 912-918.
Litman et al., "Reconstructing immune phylogeny: new perspectives", Nature Reviews Immunology 5.11 (2005): 866-879.
Litman et al., "The evolution of the immune response VIII. Structural studies of the lamprey immunoglobulin", The Journal of Immunology 105.5 (1970): 1278-1285.
Lopez et al., "The alpha and beta chains of human platelet glycoprotein Ib are both transmembrane proteins containing a leucine-rich amino acid sequence", Proceedings of the National Academy of Sciences 85.7 (1988): 2135-2139.
Mallatt et al., "Fossil sister group of craniates: predicted and found", Journal of Morphology 258.1 (2003): 1-31.

(56) References Cited

OTHER PUBLICATIONS

Marchalonis et al., "Phylogenetic origins of antibody structure III. Antibodies in the primary immune response of the sea lamprey, *Petromyzon marinus*", The Journal of experimental medicine 127.5 (1968): 891-914.

Mayer et al., "Identification of Two Ikaros-like Transcription Factors in Lamprey", Scandinavian journal of immunology 55.2 (2002): 162-170.

Mayer et al., "Isolation and characterization of lymphocyte-like cells from a lamprey", Proceedings of the National Academy of Sciences 99.22 (2002): 14350-14355.

Meyer et al., "Recent advances in the (molecular) phylogeny of vertebrates", Annual Review of Ecology, Evolution, and Systematics (2003): 311-338.

Nagawa et al., "Antigen-receptor genes of the agnathan lamprey are assembled by a process involving copy choice", Nature immunology 8.2 (2007): 206-213.

Newton et al., "Chemotactic responses of hagfish (*Vertebrata, Agnatha*) leucocytes", Developmental & Comparative Immunology 18.4 (1994): 295-303.

Pancer et al., "Prototypic T cell receptor and CD4-like coreceptor are expressed by lymphocytes in the agnathan sea lamprey", Proceedings of the National Academy of Sciences of the United States of America 101.36 (2004): 13273-13278.

Pancer, "Somatic diversification of variable lymphocyte receptors in the agnathan sea lamprey", Nature 430.6996 (2004): 174-180.

Pancer, "The evolution of adaptive immunity", Annu. Rev. Immunol. 24 (2006): 497-518.

Pancer et al., "Variable lumphocyte receptors in hagfish", Proc. Natl. Acad. Sci. USA 102:9224-9 (2005).

Penn et al., "MHC heterozygosity confers a selective advantage against multiple-strain infections", Proceedings of the National Academy of Sciences 99.17 (2002): 11260-11264.

Perey et al., "Evolution of the immune response. VI. First and second set skin homograft rejections in primitive fishes", Laboratory investigation; a journal of technical methods and pathology 19.6 (1968): 591-97.

Piavis et al., "Blood cell lineage in the sea lamprey, *Petromyzon marinus* (Pisces: Petromyzontidae)", Copeia (1971): 722-728.

Pignot, "Characterization of two novel proteins, NgRH1 and NgRH2, structurally and biochemically homologous to the Nogo-66 receptor", Journal of neurochemistry 85.3 (2003): 717-728.

Pollara et al., "The Evolution of the Immune Response VII. Antibody to Human "O" Cells and Properties of the Immunoglobulin in Lamprey", The Journal of Immunology 105.3 (1970): 738-745.

Prieto et al., "Expression of Human H-type α1, 2-Fucosyltransferase Encoding for Blood Group H (O) Antigen in Chinese Hamster Ovary Cells Evidence for Preferential Fucosylation and Truncation of Polylactosamine Sequences", Journal of Biological Chemistry 272.4 (1997): 2089-2097.

Raison et al., "A cell-surface opsonic receptor on leucocytes from the phylogenetically primitive vertebrate, Eptatretus stouti", Immunology & Cell Biology 72.4:326-332 (1994).

Rast et al., "α, β, γ, and δ T cell antigen receptor genes arose early in vertebrate phylogeny", Immunity 6.1 (1997): 1-11.

Rogozin et al., "Evolution and diversification of lamprey antigen receptors: evidence for involvement of an AID-APOBEC family cytosine deaminase", Nature immunology 8.6 (2007): 647-656.

Schluter et al., "'Big Bang' emergence of the combinatorial immune system", Developmental and comparative immunology 23.2 (1998): 107-111.

Schwede et al., "Protein structure computing in the genomic era", Research in Microbiology 151.2 (2000): 107-112.

Science, "Supporting Online Material", vol. 310, 2005, pp. 1970-1973.

Shintani et al., "Do lampreys have lymphocytes? The Spi evidence", Proceedings of the National Academy of Sciences 97.13 (2000): 7417-7422.

Steichen et al., "Identification of the immunodominant protein and other proteins of the Bacillus anthracis exosporium", Journal of bacteriology 185.6 (2003): 1903-1910.

Stumpp et al., "Designing repeat proteins: modular leucine-rich repeat protein libraries based on the mammalian ribonuclease inhibitor family", Journal of molecular biology 332.2 (2003): 471-487.

Suzuki et al., "Construction of a bacterial artificial chromosome library from the inshore hagfish, *Eptatretus burgeri*: a resource for the analysis of the agnathan genome", Genes & genetic systems 79.4 (2004): 251-253.

Suzuki et al., "Transcriptome analysis of hagfish leukocytes: a framework for understanding the immune system of jawless fishes", Developmental & Comparative Immunology 28.10 (2004): 993-1003.

Uinuk-Ool, "Identification and characterization of a TAP-family gene in the lamprey", Immunogenetics 55.1 (2003): 38-48.

Uinuk-Ool et al., "Lamprey lymphocyte-like cells express homologs of genes involved in immunologically relevant activities of mammalian lymphocytes", Proceedings of the National Academy of Sciences 99.22 (2002): 14356-14361.

Wang et al., "Characterization of the vls antigenic variation loci of the Lyme disease spirochaetes Borrelia garinii Ip90 and Borrelia afzelii ACAI", Molecular microbiology 47.5 (2003): 1407-1417.

Zapata et al., "Plasma cells in the ammocoete of Petromyzon marinus", Cell and tissue research, vol. 221, Issue 1, 1981, pp. 203-208.

Notice of Allowance in related Canadian Application No. 2,659,574 dated Dec. 14, 2016.

Examination Report No. 1 in related Australian Application No. 2016203994 dated May 19, 2017.

Alder et al., Diversity and Function of Adaptive Immune Receptors in a Jawless Vertebrate, Science, vol. 310, Dec. 23, 2005, pp. 1970-1973.

Examination Report No. 2 issued for Australian Application No. 2016203994 dated May 9, 2018 (3 pages).

Notice of Acceptance for Australian Application No. 2016203994 dated May 25, 2018 (3 pages).

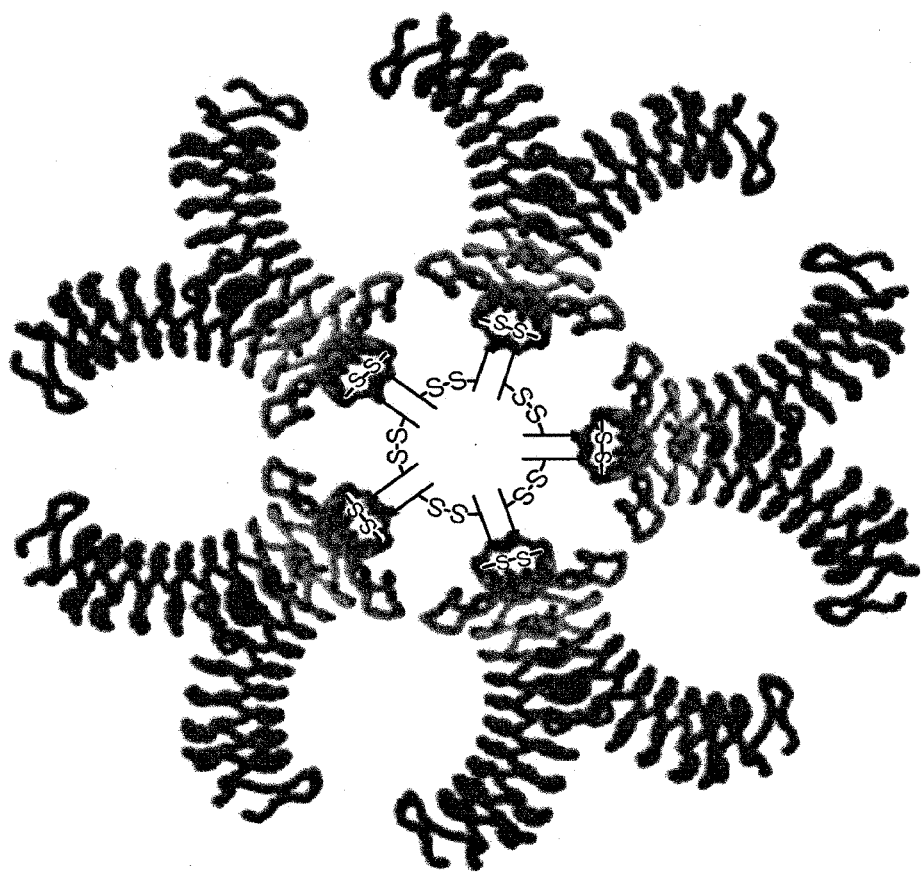
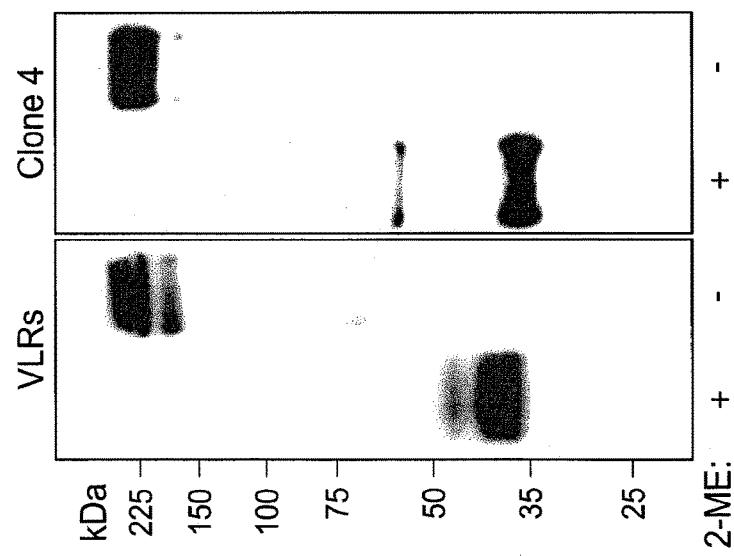
FIG. 1B
FIG. 1A

```
anthracis : LGLPAGLYAFNSGGISLDLGINDPVPFNTVGSQFGTAISQLDADIFVISETGFYKITVJANTATASV : 67
cereus    : LGLPAGLYAFNSAGISLDLGINDPVPFNTVGSQFGTAISQLDADIFVISETGFYKITVJWNTAAISV : 67
anthracis : GGLTIQVNGVPVPGTGSSLISLGAPIVIQAITQITTTPSLVEVIVTGLSLALGTSASIIEKMA : 134
cereus    : GGLTIQVNGLPVPGTGATLISMGAPIVQAITQITTTPSLVEVIVTGLSLALGTSASIIEKIA : 134
```

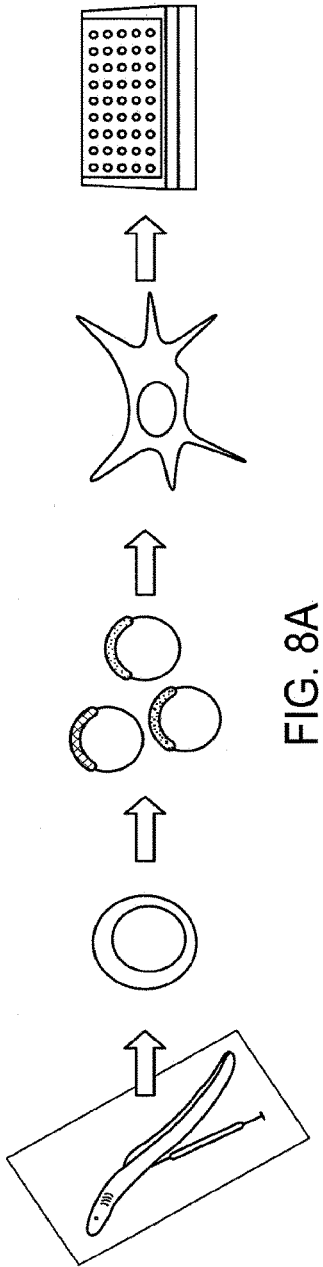
FIG. 7
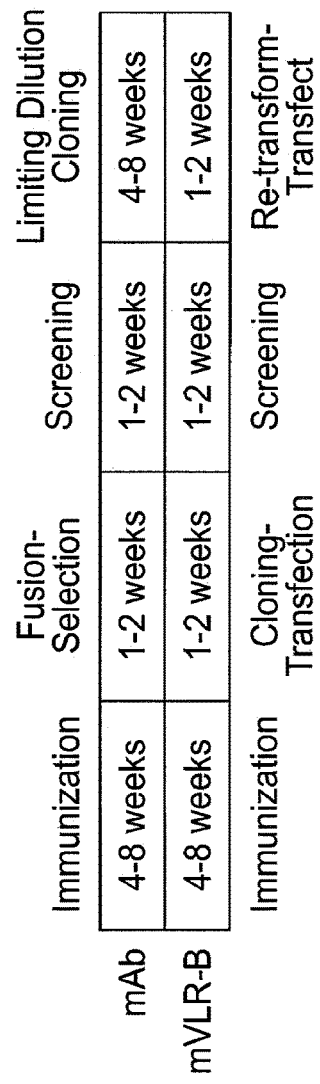
FIG. 8A
FIG. 8B

WT Spores

Anti-BclA mVLR-B

ΔBclA Spores

Anti-BclA mVLR-B

FIG. 9C

BCIA-CTD

FIG. 9E

```
B. anthracis  LGLPAGLYAFNSGGISLDLGINDPVPFNTVGSQFG 35
B. cereus T   LGLPAGLYAFNSAGISLDLGLNAPVPFNTVGSQFG 35

B. anthracis  TAISQLDADTFVISETGFYKITVIANTATASVLGG 70
B. cereus T   TAISQLDADTFVIAETGFYKITVIVYTAAISVLGG 70

B. anthracis  LTIQVNGVPVPGTGSSLISLGAPIVIQAITQITTT 105
B. cereus T   LTIQVNGVSVPGTGATLISVGAPIVVQAITQITTT 105

B. anthracis  PSLVEVIVTGLGLSLALGTSASIIIEKVA 134
B. cereus T   PSLVEVIVTGLGLSLALGTNASIIIEKVA 134
```

FIG. 9D

```
           <           LRRNT              ><    LRR1
vBA41    CPSQCSCSGTDVNCHERRLASVPAEIPTTTKILRLYI
vBA191   CPSQCSCSGTDVNCHERRLASVPAEIPTTTKILRLYI
VLR4     CPSQCSCSGTTVNCQERSLASVPAGIPTTTQVLHLYI
VLR5     CPSQCSCSGTDINCHERSLRSVPVGIPTTTQVLYLYI

><       LRRV            ><
vBA41    NQITKLEPGVFHSLTALTSLELGGNQLTALPAGIFDK
vBA191   NQITKLEPGVFDSLTQLTYLNLAVNQLTALPVGVFDN
VLR4     NQITKLEPGVFDSLTQLTYLNLAVNQLTALPVGVFDK
VLR5     NKITKLEPGIFDSLTQLTYLNLAVNQLTALPVGYFDH

LRRVe              ><         CP
vBA41    LTKLTHLALHINQLKSIPRGAFDNLKSLTHIYLFNN
vBA191   LTQLSILNMHTNQLKNIPRGAFDNLKSLTHIYLFNN
VLR4     LTKLTHLALHINQLKSIPMGVFDNLKSLTHIYLFNN
VLR5     LVNLQQLSLHTNQLKSIPRGAFDNLKSLTHIWLFNN
```

FIG. 12A

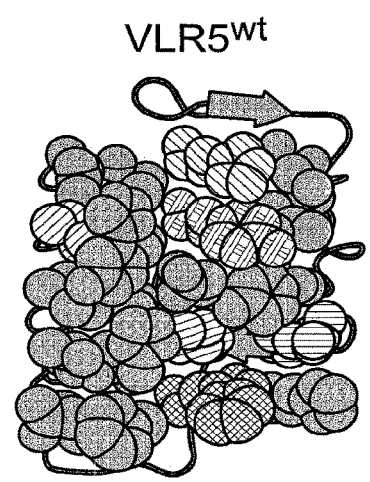

FIG. 12B

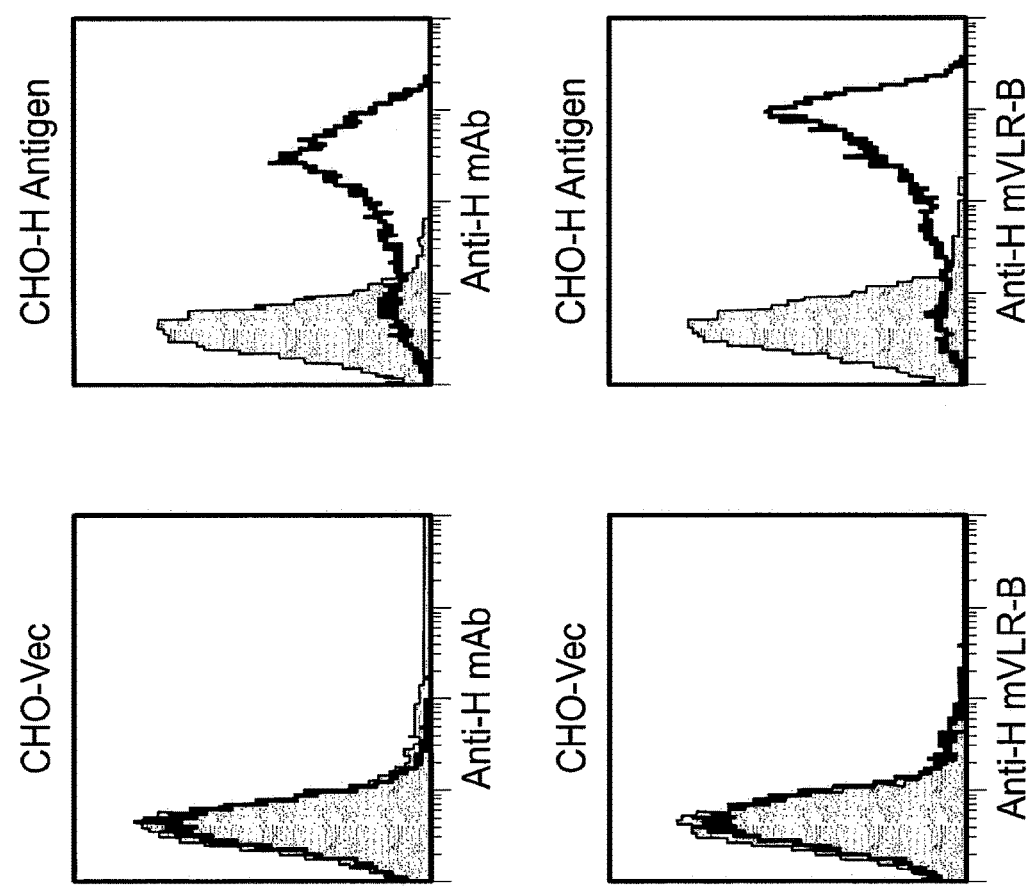

SEQUENCE LISTING

<160> NUMBER OF SEQ ID NOS: 61

<210> SEQ ID NO 1
<211> LENGTH: 134
<212> TYPE: PRT
<213> ORGANISM: Bacillus anthracis.

<400> SEQUENCE: 1

Leu Gly Leu Pro Ala Gly Leu Tyr Ala Phe Asn Ser Gly Gly Ile Ser
 1               5                  10                  15

Leu Asp Leu Gly Ile Asn Asp Pro Val Pro Phe Asn Thr Val Gly Ser
            20                  25                  30

Gln Phe Gly Thr Ala Ile Ser Gln Leu Asp Ala Asp Thr Phe Val Ile
        35                  40                  45

Ser Glu Thr Gly Phe Tyr Lys Ile Thr Val Ile Ala Asn Thr Ala Thr
    50                  55                  60

Ala Ser Val Leu Gly Gly Leu Thr Ile Gln Val Asn Gly Val Pro Val
65                  70                  75                  80

Pro Gly Thr Gly Ser Ser Leu Ile Ser Leu Gly Ala Pro Ile Val Ile
                85                  90                  95

Gln Ala Ile Thr Gln Ile Thr Thr Pro Ser Leu Val Glu Val Ile
            100                 105                 110

Val Thr Gly Leu Gly Leu Ser Leu Ala Leu Gly Thr Ser Ala Ser Ile
                115                 120                 125

Ile Ile Glu Lys Val Ala
        130

<210> SEQ ID NO 2
<211> LENGTH: 134
<212> TYPE: PRT
<213> ORGANISM: Bacillus cereus

<400> SEQUENCE: 2

Leu Gly Leu Pro Ala Gly Leu Tyr Ala Phe Asn Ser Ala Gly Ile Ser
1               5                   10                  15

Leu Asp Leu Gly Leu Asn Ala Pro Val Pro Phe Asn Thr Val Gly Ser
                20                  25                  30

Gln Phe Gly Thr Ala Ile Ser Gln Leu Asp Ala Asp Thr Phe Val Ile
            35                  40                  45

Ala Glu Thr Gly Phe Tyr Lys Ile Thr Val Ile Val Tyr Thr Ala Ala
    50                  55                  60

Ile Ser Val Leu Gly Gly Leu Thr Ile Gln Val Asn Gly Val Ser Val
65                  70                  75                  80

Pro Gly Thr Gly Ala Thr Leu Ile Ser Val Gly Ala Pro Ile Val Val
                85                  90                  95

Gln Ala Ile Thr Gln Ile Thr Thr Pro Ser Leu Val Glu Val Ile
            100                 105                 110

Val Thr Gly Leu Gly Leu Ser Leu Ala Leu Gly Thr Asn Ala Ser Ile
                115                 120                 125

Ile Ile Glu Lys Val Ala
        130

<210> SEQ ID NO 3
<211> LENGTH: 144
<212> TYPE: PRT
<213> ORGANISM: Artificial Sequence
<220> FEATURE:
<223> OTHER INFORMATION: Synthetically generated peptide

<400> SEQUENCE: 3

Cys Pro Ser Gln Cys Ser Cys Ser Gly Thr Thr Val Asn Cys Gln Glu
1               5                   10                  15

Arg Ser Leu Ala Ser Val Pro Ala Gly Ile Pro Thr Thr Thr Gln Val
                20                  25                  30

Leu His Leu Tyr Ile Asn Gln Ile Thr Lys Leu Glu Pro Gly Val Phe
            35                  40                  45

Asp Ser Leu Thr Gln Leu Thr Tyr Leu Asn Leu Ala Val Asn Gln Leu
    50                  55                  60

Thr Ala Leu Pro Val Gly Val Phe Asp Lys Leu Thr Lys Leu Thr His
65                  70                  75                  80

Leu Ala Leu His Ile Asn Gln Leu Lys Ser Ile Pro Met Gly Val Phe

```
                        85                  90                  95

Asp Asn Leu Lys Ser Leu Thr His Ile Tyr Leu Phe Asn Asn Pro Trp
            100                 105                 110

Asp Cys Glu Cys Ser Asp Ile Leu Tyr Leu Lys Asn Trp Ile Val Gln
            115                 120                 125

His Ala Ser Ile Val Asn Pro Leu Gly Asn Gly Gly Val Asp Asn Val
        130                 135                 140

<210> SEQ ID NO 4
<211> LENGTH: 144
<212> TYPE: PRT
<213> ORGANISM: Artificial Sequence
<220> FEATURE:
<223> OTHER INFORMATION: Synthetically generated peptide

<400> SEQUENCE: 4

Cys Pro Ser Gln Cys Ser Cys Ser Gly Thr Asp Ile His Cys His Glu
1               5                   10                  15

Arg Ser Leu Arg Ser Val Pro Val Gly Ile Pro Thr Thr Thr Gln Val
            20                  25                  30

Leu Tyr Leu Tyr Thr Asn Lys Ile Thr Lys Leu Glu Pro Gly Leu Phe
        35                  40                  45

Asp Ser Leu Thr Gln Leu Thr Tyr Leu Asn Leu Ala Val Asn Gln Leu
    50                  55                  60

Thr Ala Leu Pro Val Gly Val Phe Asp His Leu Val Asn Leu Gln Gln
65                  70                  75                  80

Leu Ser Leu His Thr Asn Gln Leu Lys Ser Ile Pro Arg Gly Ala Phe
                85                  90                  95

Asp Asn Leu Lys Ser Leu Thr His Ile Trp Leu Phe Asn Asn Pro Trp
            100                 105                 110

Asp Cys Glu Cys Ser Asp Ile Leu Tyr Leu Lys Asn Trp Ile Val Gln
            115                 120                 125

His Ala Ser Ile Val Asn Pro Leu Gly Asn Gly Gly Val Asp Asn Val
        130                 135                 140

<210> SEQ ID NO 5
<211> LENGTH: 270
<212> TYPE: PRT
<213> ORGANISM: Artificial Sequence
<220> FEATURE:
<223> OTHER INFORMATION: Synthetically generated peptide

<400> SEQUENCE: 5

Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Ser Gly Thr Thr
            20                  25                  30

Val Asn Cys Gln Glu Arg Ser Leu Ala Ser Val Pro Ala Gly Ile Pro
        35                  40                  45

Thr Thr Thr Gln Val Leu His Leu Tyr Ile Asn Gln Ile Thr Lys Leu
    50                  55                  60

Glu Pro Gly Val Phe Asp Ser Leu Thr Gln Leu Thr Tyr Leu Asn Leu
65                  70                  75                  80

Ala Val Asn Gln Leu Thr Ala Leu Pro Val Gly Val Phe Asp Lys Leu
                85                  90                  95

Thr Lys Leu Thr His Leu Ala Leu His Ile Asn Gln Leu Lys Ser Ile
            100                 105                 110
```

```
Pro Met Gly Val Phe Asp Asn Leu Lys Ser Leu Thr His Ile Tyr Leu
        115                 120                 125

Phe Asn Asn Pro Trp Asp Cys Glu Cys Ser Asp Ile Leu Tyr Leu Lys
130                 135                 140

Asn Trp Ile Val Gln His Ala Ser Ile Val Asn Pro Leu Gly Asn Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
            260                 265                 270
```

<210> SEQ ID NO 6
<211> LENGTH: 270
<212> TYPE: PRT
<213> ORGANISM: Artificial Sequence
<220> FEATURE:
<223> OTHER INFORMATION: Synthetically generated peptide

<400> SEQUENCE: 6

```
Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Ser Gly Thr Asp
                20                  25                  30

Ile His Cys His Glu Arg Ser Leu Arg Ser Val Pro Val Gly Ile Pro
            35                  40                  45

Thr Thr Thr Gln Val Leu Tyr Leu Tyr Thr Asn Lys Ile Thr Lys Leu
        50                  55                  60

Glu Pro Gly Leu Phe Asp Ser Leu Thr Gln Leu Thr Tyr Leu Asn Leu
65                  70                  75                  80

Ala Val Asn Gln Leu Thr Ala Leu Pro Val Gly Val Phe Asp His Leu
                85                  90                  95

Val Asn Leu Gln Gln Leu Ser Leu His Thr Asn Gln Leu Lys Ser Ile
            100                 105                 110

Pro Arg Gly Ala Phe Asp Asn Leu Lys Ser Leu Thr His Ile Trp Leu
        115                 120                 125

Phe Asn Asn Pro Trp Asp Cys Glu Cys Ser Asp Ile Leu Tyr Leu Lys
130                 135                 140

Asn Trp Ile Val Gln His Ala Ser Ile Val Asn Pro Leu Gly Asn Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Thr Pro Glu Phe Ile Pro Glu Thr
        195                 200                 205
```

```
Thr Thr Ser Pro Gln Pro Val Ile Thr Thr Gln Lys Pro Lys Pro Leu
        210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
            260                 265                 270

<210> SEQ ID NO 7
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Pro or Leu
<220> FEATURE:
<221> NAME/KEY: VARIANT
<222> LOCATION: 14
<223> OTHER INFORMATION: Xaa = any amino acid
<220> FEATURE:
<221> NAME/KEY: VARIANT
<222> LOCATION: 15
<223> OTHER INFORMATION: Xaa = Ser, Tyr, Asn or His

<400> SEQUENCE: 7

Lys Asn Trp Ile Val Gln His Ala Ser Ile Val Asn Xaa Xaa Xaa Gly
1               5                   10                  15

Gly Val Asp Asn Val Lys
            20

<210> SEQ ID NO 8
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Pro Or Leu
<220> FEATURE:
<221> NAME/KEY: VARIANT
<222> LOCATION: 14, 15
<223> OTHER INFORMATION: Xaa = any amino acid
<220> FEATURE:
<221> NAME/KEY: VARIANT
<222> LOCATION: 16
<223> OTHER INFORMATION: Xaa = Ser, Tyr, Asn or His

<400> SEQUENCE: 8

Lys Asn Trp Ile Val Gln His Ala Ser Ile Val Asn Xaa Xaa Xaa Xaa
1               5                   10                  15

Gly Gly Val Asp Asn Val Lys
            20

<210> SEQ ID NO 9
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 9

Cys Pro Ser Gln Cys Ser Cys
```

```
                   1               5

<210> SEQ ID NO 10
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 10

Cys Pro Ser Arg Cys Ser Cys
  1               5

<210> SEQ ID NO 11
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 11

Cys Pro Ala Gln Cys Ser Cys
  1               5

<210> SEQ ID NO 12
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 12

Cys Pro Ser Gln Cys Leu Cys
  1               5

<210> SEQ ID NO 13
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 13

Cys Pro Ser Gln Cys Pro Cys
  1               5

<210> SEQ ID NO 14
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 14

Asn Gly Ala Thr Cys Lys Lys
  1               5

<210> SEQ ID NO 15
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 15

Asn Glu Ala Leu Cys Lys Lys
  1               5
```

```
<210> SEQ ID NO 16
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 16

Thr Asn Thr Pro Val Arg Ala Val Thr Glu Ala Ser Thr Ser Pro Ser
1               5                   10                  15

Lys Cys Pro

<210> SEQ ID NO 17
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 17

Ser Gly Lys Pro Val Arg Ser Ile Ile Cys Pro
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 18

Ser Ser Lys Ala Val Leu Asp Val Thr Glu Glu Ala Ala Glu Asp
1               5                   10                  15

Cys Val

<210> SEQ ID NO 19
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 19

Gln Ser Lys Ala Val Leu Glu Ile Thr Glu Lys Asp Ala Ala Ser Asp
1               5                   10                  15

Cys Val

<210> SEQ ID NO 20
<211> LENGTH: 320
<212> TYPE: PRT
<213> ORGANISM: Artificial Sequence
<220> FEATURE:
<223> OTHER INFORMATION: Synthetically generated peptide

<400> SEQUENCE: 20

Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Ser Gly Thr Thr
                20                  25                  30

Val Asp Cys Arg Ser Lys Arg His Ala Ser Val Pro Ala Gly Ile Pro
            35                  40                  45

Thr Asn Ala Gln Ile Leu Tyr Leu His Asp Asn Gln Ile Thr Lys Leu
```

```
            50                  55                  60
Glu Pro Gly Val Phe Asp Ser Leu Ile Asn Leu Lys Glu Leu Tyr Leu
 65                  70                  75                  80

Gly Ser Asn Gln Leu Gly Ala Leu Pro Val Gly Val Phe Asp Ser Leu
                 85                  90                  95

Thr Gln Leu Thr Val Leu Asp Leu Gly Thr Asn Gln Leu Thr Val Leu
            100                 105                 110

Pro Ser Ala Val Phe Asp Arg Leu Val His Leu Lys Glu Leu Phe Met
            115                 120                 125

Cys Cys Asn Lys Leu Thr Glu Leu Pro Arg Gly Ile Glu Arg Leu Thr
        130                 135                 140

His Leu Thr His Leu Ala Leu Asp Gln Asn Gln Leu Lys Ser Ile Pro
145                 150                 155                 160

His Gly Ala Phe Asp Arg Leu Ser Ser Leu Thr His Ala Tyr Leu Phe
                165                 170                 175

Gly Asn Pro Trp Asp Cys Glu Cys Arg Asp Ile Met Tyr Leu Arg Asn
                180                 185                 190

Trp Val Ala Asp His Thr Ser Ile Ala Met Arg Trp Asp Gly Lys Ala
            195                 200                 205

Val Asn Asp Pro Asp Ser Ala Lys Cys Ala Gly Thr Asn Thr Pro Val
210                 215                 220

Arg Ala Val Thr Glu Ala Ser Thr Ser Pro Ser Lys Cys Pro Gly Tyr
225                 230                 235                 240

Val Ala Thr Thr Thr Thr Pro Thr Thr Thr Pro Glu Phe Ile Pro
                245                 250                 255

Glu Thr Thr Thr Ser Pro Gln Pro Val Ile Thr Thr Gln Lys Pro Lys
            260                 265                 270

Pro Leu Trp Asn Phe Asn Cys Thr Ser Ile Gln Glu Arg Lys Asn Asp
                275                 280                 285

Gly Gly Asp Cys Gly Lys Pro Ala Cys Thr Thr Leu Leu Asn Cys Ala
        290                 295                 300

Asn Phe Leu Ser Cys Leu Cys Ser Thr Cys Ala Leu Cys Arg Lys Arg
305                 310                 315                 320

<210> SEQ ID NO 21
<211> LENGTH: 813
<212> TYPE: DNA
<213> ORGANISM: Artificial Sequence
<220> FEATURE:
<223> OTHER INFORMATION: Synthetically generated oligonucleotide

<400> SEQUENCE: 21
atgtggatca agtggatcgc cacgctggtc gcctttggcg ccctggtgca aagtgcggta    60
gcatgtccct cgcagtgttc gtgctcaggg acaactgtga actgccaaga gagaagcctc   120
gcgtctgtgc ctgcgggaat ccccaccacc acgcaagttc tgcatttgta cataaatcag   180
atcacgaagc tcgagccagg ggtgtttgat agtctgacgc aactgactta tctgaacctt   240
gctgttaacc agctgacggc tcttcccgtt ggggtgtttg acaaactgac caaactcact   300
catctggctc tgcacatcaa tcaactgaag agcattccca tgggcgtttt tgacaacctc   360
aagagcctca ctcacatcta tctgttcaac aaccccctggg actgcgagtg ttcggacatc   420
ctctatctga gaactggat tgtgcagcac gcaagcatcg tgaatccatt gggcaatggg   480
ggagttgata acgtgaagtg ctctggtacc aataccccg tccgtgcggt caccgaggcc   540
agcactagcc cctcgaaatg cccaggctac gttgctacga ccacgacgcc gacgacgacc   600
```

```
acgcccgaat tcatccctga gaccaccacc tcgccgcagc ccgtgatcac aacccagaaa    660
cccaagcctc tgtggaattt caactgcacc tcaattcagg agaggaagaa cgacggtggc    720
gactgcggaa agcccgcctg cacaactctc ctgaactgcg cgaatttcct cagctgcctc    780
tgctcgacct gcgccctctg caggaaacgt tga                                 813
```

<210> SEQ ID NO 22
<211> LENGTH: 250
<212> TYPE: PRT
<213> ORGANISM: Artificial Sequence
<220> FEATURE:
<223> OTHER INFORMATION: Synthetically generated peptide

<400> SEQUENCE: 22

```
Met Trp Ile Lys Trp Ile Ala Thr Leu Val Ala Phe Gly Ala Leu Val
  1               5                  10                  15

Gln Ser Ala Val Ala Cys Pro Ser Gln Cys Ser Cys Arg Val Trp Ser
             20                  25                  30

Gly Leu Arg Tyr Thr Asp Cys Ser Ser Lys Gly Leu Ser Ser Val Pro
         35                  40                  45

Asn Glu Ile Pro Gly Asn Thr Gln Val Leu Val Leu Ser Gly Asn Gln
     50                  55                  60

Ile Glu Ser Leu Ser Glu Gly Val Phe Asp Arg Leu Val Asn Leu Gln
 65                  70                  75                  80

Lys Leu Trp Leu Asn Ser Asn Arg Leu Lys Ser Ile Pro Arg Gly Ala
                 85                  90                  95

Phe Asp Asn Leu Lys Ser Leu Thr Asn Ile Trp Leu Ser Ser Asn Pro
            100                 105                 110

Trp Asp Cys Glu Cys Ser Asp Ile Leu Tyr Leu Lys Asn Trp Ile Val
        115                 120                 125

Gln His Ala Ser Ile Val Asn Pro Asp Gly His Gly Gly Val Asp Asn
    130                 135                 140

Val Lys Cys Ser Gly Thr Asn Thr Pro Val Arg Ala Val Thr Glu Ala
145                 150                 155                 160

Ser Thr Ser Pro Ser Lys Cys Pro Gly Tyr Val Ala Thr Thr Thr Thr
                165                 170                 175

Pro Thr Thr Thr Thr Pro Glu Phe Ile Pro Glu Thr Thr Thr Ser Pro
            180                 185                 190

Gln Pro Val Ile Thr Thr Gln Lys Pro Lys Pro Leu Trp Asn Phe Asn
        195                 200                 205

Tyr Thr Ser Ile Gln Glu Arg Lys Asn Asp Gly Asp Cys Gly Lys
    210                 215                 220

Pro Ala Cys Thr Thr Leu Leu Asn Cys Ala Asn Phe Leu Ser Cys Leu
225                 230                 235                 240

Cys Ser Thr Cys Ala Leu Cys Arg Lys Arg
                245                 250
```

<210> SEQ ID NO 23
<211> LENGTH: 753
<212> TYPE: DNA
<213> ORGANISM: Artificial Sequence
<220> FEATURE:
<223> OTHER INFORMATION: Synthetically generated oligonucleotide

<400> SEQUENCE: 23

```
atgtggatca gtggatcgc cacgctggtc gcctttggcg ccctggtgca aagtgcggta    60
```

```
gcatgtccct cgcagtgttc gtgtcgcgtg tggtctggac tccgttatac ggactgtagc    120
agcaaagggc tgagttcggt tcccaatgag atccctggca acacccaggt tctggttttg    180
agtggcaatc aaattgagag tctctccgag ggggtgtttg accgcctggt gaatctgcag    240
aagctgtggt tgaacagcaa ccggctgaag agcattccca ggggcgcctt tgacaacctc    300
aagagcctca ctaacatctg gctgtccagc aaccccctggg actgcgagtg ttcggacatc    360
ctctatctaa agaactggat tgtgcagcat gcaagcatcg tgaatccaga cggccatggg    420
ggagttgata acgtgaagtg ctctggtacc aataccccg tccgtgcggt caccgaggcc    480
agcactagcc cctcgaaatg cccaggctac gttgctacga ccacgacgcc gacgacgacc    540
acgcccgaat tcatccctga ccaccacc tcgccgcagc ccgtgatcac aacccagaaa    600
cccaagcctc tgtggaattt caactacacc tcaattcagg agaggaagaa cgacggtggc    660
gactgcggaa agcccgcctg cacaactctc ctgaactgcg cgaatttcct cagctgcctc    720
tgctcgacct gcgccctctg caggaaacgt tga                                 753
```

<210> SEQ ID NO 24
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 24
tgtccctcgc agtgttcgtg t          21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 25
tgtccctcgc ggtgttcgtg t          21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 26
tgtcccgcgc agtgttcgtg t          21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 27
tgtccctcgc agtgtttgtg t          21

<210> SEQ ID NO 28
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 28
tgtccctcgc agtgtccgtg t                                      21

<210> SEQ ID NO 29
<211> LENGTH: 57
<212> TYPE: DNA
<213> ORGANISM: Artificial Sequence
<220> FEATURE:
<223> OTHER INFORMATION: Synthetically generated oligonucleotide

<400> SEQUENCE: 29
accaataccc ccgtccgtgc ggtcaccgag gccagcacta gcccctcgaa atgccca     57

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
ccaccatgtg gatcaagtgg atcgcc                                 26

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31
gagagctagc tcaacgtttc ctgcagaggg c                           31

<210> SEQ ID NO 32
<211> LENGTH: 963
<212> TYPE: DNA
<213> ORGANISM: Artificial Sequence
<220> FEATURE:
<223> OTHER INFORMATION: Synthetically generated oligonucleotide

<400> SEQUENCE: 32
atgtggatca agtggatcgc cacgctggtc gcctttggcg ccctggtgca aagtgcggta     60
gcatgtccct cgcagtgttc ctgctcaggg acaactgtgg attgccggag caaacgccac    120
gcatccgtgc ctgcgggaat ccccaccaat gcgcagattc tgtatttaca cgacaatcag    180
atcacgaagc tcgagcccgg ggtgtttgac agcctcataa atctgaagga gctgtatctg    240
ggctcgaacc agctggggc tctacccgtt ggggttttg acagtctgac gcaacttact    300
gtcctggacc ttggtaccaa ccagctaaca gttctaccct ctgcggtgtt tgatcgcctg    360
gtgcatctaa aagagctgtt tatgtgctgc aataagctca cggagctgcc ccgtggcatt    420
gagagactca cccatttgac tcatttagct ctggaccaaa accagttgaa gagcatcccg    480
catggagcgt tcgaccgtct cagctccctc acccacgcct atttatttgg caacccatgg    540
gattgcgagt gcagggacat tatgtacctc aggaactggg tcgcagacca cacttctatt    600
gcaatgcgct gggatgggaa ggccgttaac gaccccgact ctgccaagtg cgctggtacc    660
aataccccg tccgtgcggt caccgaggcc agcactagcc cctcgaaatg cccaggctac    720
gttgctacga ccacgacgcc gacgacgacc acgcccgaat tcatccctga ccaccacc     780
tcgccgcagc ccgtgatcac aacccagaaa cccaagcctc tgtggaattt caactgcacc    840

```
tcaattcagg agaggaagaa cgacggtggc gactgcggaa agcccgcctg cacaactctc    900
ctgaactgcg cgaatttcct cagctgcctc tgctcgacct gcgccctctg caggaaacgt    960
tga                                                                  963
```

<210> SEQ ID NO 33
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 33

Ser Arg Asp Thr
 1

<210> SEQ ID NO 34
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 34

Asp His Tyr Ile
 1

<210> SEQ ID NO 35
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 35

Ser Gly Tyr Glu
 1

<210> SEQ ID NO 36
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 36

Thr Gly Asp Val
 1

<210> SEQ ID NO 37
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 37

Cys Cys Phe Glu
 1

<210> SEQ ID NO 38
<211> LENGTH: 4
<212> TYPE: PRT
<213> ORGANISM: Artificial Sequence
<220> FEATURE:
<223> OTHER INFORMATION: Synthetically generated peptide -continued

```
<400> SEQUENCE: 38

Gln Asp Ala His
  1

<210> SEQ ID NO 39
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 39

Gly Phe Tyr His
  1

<210> SEQ ID NO 40
<211> LENGTH: 43
<212> TYPE: PRT
<213> ORGANISM: Artificial Sequence
<220> FEATURE:
<223> OTHER INFORMATION: Synthetically generated peptide

<400> SEQUENCE: 40

Asn Cys Thr Ser Ile Gln Glu Arg Lys Asn Asp Gly Gly Asp Cys Gly
  1               5                  10                  15

Lys Pro Ala Cys Thr Thr Leu Leu Asn Cys Ala Asn Phe Leu Ser Cys
             20                  25                  30

Leu Cys Ser Thr Cys Ala Leu Cys Arg Lys Arg
         35                  40

<210> SEQ ID NO 41
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 41

Cys Pro Ser Gln Cys Ser Cys Ser Gly Thr Asp Val Asn Cys His Glu
  1               5                  10                  15

Arg Arg Leu Ala Ser Val Pro Ala Glu Ile Pro Thr Thr Thr Lys Ile
             20                  25                  30

Leu Arg Leu Tyr Ile Asn Gln Ile Thr Lys Leu Glu Pro Gly Val Phe
         35                  40                  45

His Ser Leu Thr Ala Leu Thr Ser Leu Glu Leu Gly Gly Asn Gln Leu
     50                  55                  60

Thr Ala Leu Pro Ala Gly Ile Phe Asp Lys Leu Thr Lys Leu Thr His
 65                  70                  75                  80

Leu Ala Leu His Ile Asn Gln Leu Lys Ser Ile Pro Arg Gly Ala Phe
                 85                  90                  95

Asp Asn Leu Lys Ser Leu Thr His Ile Tyr Leu Phe Asn Asn
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 42

Cys Pro Ser Gln Cys Ser Cys Ser Gly Thr Asp Val Asn Cys His Glu
```

-continued

```
              1               5                   10                  15
Arg Arg Leu Ala Ser Val Pro Ala Glu Ile Pro Thr Thr Thr Lys Ile
                      20                  25                  30

Leu Arg Leu Tyr Ile Asn Gln Ile Thr Lys Leu Glu Pro Gly Val Phe
                      35                  40                  45

Asp Ser Leu Thr Gln Leu Thr Tyr Leu Asn Leu Ala Val Asn Gln Leu
                      50                  55                  60

Thr Ala Leu Pro Val Gly Val Phe Asp Asn Leu Thr Gln Leu Ser Ile
 65                       70                  75                  80

Leu Asn Met His Thr Asn Gln Leu Lys Asn Ile Pro Arg Gly Ala Phe
                      85                  90                  95

Asp Asn Leu Lys Ser Leu Thr His Ile Tyr Leu Phe Asn Asn
                     100                 105                 110
```

<210> SEQ ID NO 43
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 43

```
Cys Pro Ser Gln Cys Ser Cys Ser Gly Thr Thr Val Asn Cys Gln Glu
 1               5                   10                  15

Arg Ser Leu Ala Ser Val Pro Ala Gly Ile Pro Thr Thr Thr Gln Val
                      20                  25                  30

Leu His Leu Tyr Ile Asn Gln Ile Thr Lys Leu Glu Pro Gly Val Phe
                      35                  40                  45

Asp Ser Leu Thr Gln Leu Thr Tyr Leu Asn Leu Ala Val Asn Gln Leu
                      50                  55                  60

Thr Ala Leu Pro Val Gly Val Phe Asp Lys Leu Thr Lys Leu Thr His
 65                       70                  75                  80

Leu Ala Leu His Ile Asn Gln Leu Lys Ser Ile Pro Met Gly Val Phe
                      85                  90                  95

Asp Asn Leu Lys Ser Leu Thr His Ile Tyr Leu Phe Asn Asn
                     100                 105                 110
```

<210> SEQ ID NO 44
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 44

```
Cys Pro Ser Gln Cys Ser Cys Ser Gly Thr Asp Ile His Cys His Glu
 1               5                   10                  15

Arg Ser Leu Arg Ser Val Pro Val Gly Ile Pro Thr Thr Thr Gln Val
                      20                  25                  30

Leu Tyr Leu Tyr Thr Asn Lys Ile Thr Lys Leu Glu Pro Gly Leu Phe
                      35                  40                  45

Asp Ser Leu Thr Gln Leu Thr Tyr Leu Asn Leu Ala Val Asn Gln Leu
                      50                  55                  60

Thr Ala Leu Pro Val Gly Val Phe Asp His Leu Val Asn Leu Gln Gln
 65                       70                  75                  80

Leu Ser Leu His Thr Asn Gln Leu Lys Ser Ile Pro Arg Gly Ala Phe
                      85                  90                  95
```

Asp Asn Leu Lys Ser Leu Thr His Ile Trp Leu Phe Asn Asn
            100                 105                 110

<210> SEQ ID NO 45
<211> LENGTH: 813
<212> TYPE: DNA
<213> ORGANISM: Artificial Sequence
<220> FEATURE:
<223> OTHER INFORMATION: Synthetically generated oligonucleotide

<400> SEQUENCE: 45

| | | | | | |
|---|---|---|---|---|---|
| atgtggatca | agtggatcgc | cacgctggtc | gcctttggcg | ccctggtgca | aagtgcggta | 60 |
| gcatgtccct | cgcagtgttc | atgctcaggg | acagatattc | actgtcatga | gagaagccta | 120 |
| cggtctgtgc | ctgtgggaat | ccccaccacc | acgcaagtgc | tgtatttgta | caccaataag | 180 |
| atcacgaagc | tcgagcccgg | gctgtttgac | agcctgacgc | aactgactta | tctgaacctt | 240 |
| gctgttaacc | agctgacggc | tcttcccgtt | ggggtgtttg | accacctggt | gaatctgcag | 300 |
| cagctgagtc | tgcacaccaa | ccagctgaag | agcattccca | ggggcgcctt | tgacaacctc | 360 |
| aagagcctca | ctcacatctg | gctgttcaac | aaccctggg | actgcgagtg | ttcggacatc | 420 |
| ctctatctga | gaactggat | tgtgcagcac | gcaagcatcg | tgaatccatt | gggcaatggg | 480 |
| ggagttgata | acgtgaagtg | ctctggtacc | aataccccg | tccgtgcggt | caccgaggcc | 540 |
| agcactagcc | cctcgaaatg | cccaggctac | gttgctacga | ccacgacgcc | gacgacgacc | 600 |
| acgcccgaat | tcatccctga | ccaccacc | tcgccgcagc | ccgtgatcac | aacccagaaa | 660 |
| cccaagcctc | tgtggaattt | caactgcacc | tcaattcagg | agaggaagaa | cgacggtggc | 720 |
| gactgcggaa | agcccgcctg | cacaactctc | ctaaactgcg | cgaatttcct | cagctgcctc | 780 |
| tgctcgacct | gcgccctctg | caggaaacgt | tga | | | 813 |

<210> SEQ ID NO 46
<211> LENGTH: 813
<212> TYPE: DNA
<213> ORGANISM: Artificial Sequence
<220> FEATURE:
<223> OTHER INFORMATION: Synthetically generated oligonucleotide

<400> SEQUENCE: 46

| | | | | | |
|---|---|---|---|---|---|
| atgtggatca | agtggatcgc | cacgctggtc | gcctttggcg | ccctggtgca | aagtgcggta | 60 |
| gcatgtccct | cgcagtgttc | gtgctcaggg | acagatgtga | actgtgacag | gaaacgcttc | 120 |
| gcgtctgtgc | ctgcggcaat | ccctatcacc | acgcaaaggc | tgtggttgag | caacaatcag | 180 |
| ttaactaagc | tcgaccccgg | agtgtttgac | agcctgaccc | aactgactta | tctggacctt | 240 |
| gctgttaacc | agctgacgtc | tctccccgct | ggaatgtttg | acaaacttac | gcagctcaca | 300 |
| tatctcattc | tgcacaccaa | ccagctgaag | agcattccca | ggggcacctt | tgataacctc | 360 |
| aagagcctca | ctcacatctg | gctatacaac | aaccctggg | actgcgagtg | ttcggacatc | 420 |
| ctctatctga | gaactggat | tgtgcagcac | gcaagcatcg | tgaatccatt | gggcaatggg | 480 |
| ggagttgata | acgtgaagtg | ctctggtacc | aataccccg | tccgtgcggt | caccgaggcc | 540 |
| agcactagcc | cctcgaaatg | cccaggctac | gttgctacga | ccacgacgcc | gacgacgacc | 600 |
| acgcccgaat | tcatccctga | ccaccacc | tcgccgcagc | ccgtgatcac | aacccagaaa | 660 |
| cccaagcctc | tgtggaattt | caactgcacc | tcaattcagg | agaggaagaa | cgacggtggc | 720 |
| gactgcggaa | agcccgcctg | cacaactctc | ctaaactgcg | cgaatttcct | cagctgcctc | 780 |
| tgctcgacct | gcgccctctg | caggaaacgt | tga | | | 813 |

<210> SEQ ID NO 47
<211> LENGTH: 270
<212> TYPE: PRT
<213> ORGANISM: Artificial Sequence
<220> FEATURE:
<223> OTHER INFORMATION: Synthetically generated peptide

<400> SEQUENCE: 47

```
Met Trp Ile Lys Trp Ile Ala Thr Leu Val Ala Phe Gly Ala Leu Val
  1               5                  10                  15

Gln Ser Ala Val Ala Cys Pro Ser Gln Cys Ser Cys Ser Gly Thr Asp
             20                  25                  30

Val Asn Cys Asp Arg Lys Arg Phe Ala Ser Val Pro Ala Ala Ile Pro
         35                  40                  45

Ile Thr Thr Gln Arg Leu Trp Leu Ser Asn Asn Gln Leu Thr Lys Leu
     50                  55                  60

Asp Pro Gly Val Phe Asp Ser Leu Thr Gln Leu Thr Tyr Leu Asp Leu
 65                  70                  75                  80

Ala Val Asn Gln Leu Thr Ser Leu Pro Ala Gly Met Phe Asp Lys Leu
                 85                  90                  95

Thr Gln Leu Thr Tyr Leu Ile Leu His Thr Asn Gln Leu Lys Ser Ile
            100                 105                 110

Pro Arg Gly Thr Phe Asp Asn Leu Lys Ser Leu Thr His Ile Trp Leu
        115                 120                 125

Tyr Asn Asn Pro Trp Asp Cys Glu Cys Ser Asp Ile Leu Tyr Leu Lys
    130                 135                 140

Asn Trp Ile Val Gln His Ala Ser Ile Val Asn Pro Leu Gly Asn Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
            260                 265                 270
```

<210> SEQ ID NO 48
<211> LENGTH: 813
<212> TYPE: DNA
<213> ORGANISM: Artificial Sequence
<220> FEATURE:
<223> OTHER INFORMATION: Synthetically generated oligonucleotide

<400> SEQUENCE: 48

```
atgtggatca agtggatcgc cacgctggtc gcctttggcg ccctggtgca aagtgcggta      60
gcatgtccct cgcagtgttc gtgctcaggg acagatgtta actgtcatga gagacgcttg     120
gcgtctgtgc ctgcggaaat ccccaccacc acgaagatcc tgcggctgta catcaatcag     180
atcacgaagc tcgagcccgg cgtgtttcac agtctgacgg cactgacttc tctggaactt     240
```

```
ggtggcaacc agctgacggc tttacccgct gggatatttg acaaactgac caaactcact    300
catctggctc tgcacatcaa tcaactgaag agcattccca ggggcgcctt tgacaacctc    360
aagagcctca ctcacatcta tctgttcaac aacccctggg actgcgagtg ttcggacatc    420
ctctatctga agaactggat tgtgcagcac gcaagcatcg tgaatccatt gggcaatggg    480
ggagttgata acgtgaagtg ctctggtacc aataccccg tccgtgcggt caccgaggcc    540
agcactagcc cctcgaaatg cccaggctac gttgctacga ccacgacgcc gacgacgacc    600
acgcccgaat tcatccctga gaccaccacc tcgccgcagc cgtgatcac aacccagaaa    660 cccaagcctc tgtggaattt caactgcacc tcaattcagg agaggaagaa cgacggtggc    720
gactgcggaa agcccgcctg cacaactctc ctaaactgcg cgaatttcct cagctgcctc    780
tgctcgacct gcgccctctg caggaaacgt tga                                 813
```

```
<210> SEQ ID NO 49
<211> LENGTH: 270
<212> TYPE: PRT
<213> ORGANISM: Artificial Sequence
<220> FEATURE:
<223> OTHER INFORMATION: Synthetically generated peptide

<400> SEQUENCE: 49

Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Ser Gly Thr Asp
            20                  25                  30

Val Asn Cys His Glu Arg Arg Leu Ala Ser Val Pro Ala Glu Ile Pro
        35                  40                  45

Thr Thr Thr Lys Ile Leu Arg Leu Tyr Ile Asn Gln Ile Thr Lys Leu
    50                  55                  60

Glu Pro Gly Val Phe His Ser Leu Thr Ala Leu Thr Ser Leu Glu Leu
65                  70                  75                  80

Gly Gly Asn Gln Leu Thr Ala Leu Pro Ala Gly Ile Phe Asp Lys Leu
                85                  90                  95

Thr Lys Leu Thr His Leu Ala Leu His Ile Asn Gln Leu Lys Ser Ile
            100                 105                 110

Pro Arg Gly Ala Phe Asp Asn Leu Lys Ser Leu Thr His Ile Tyr Leu
        115                 120                 125

Phe Asn Asn Pro Trp Asp Cys Glu Cys Ser Asp Ile Leu Tyr Leu Lys
    130                 135                 140

Asn Trp Ile Val Gln His Ala Ser Ile Val Asn Pro Leu Gly Asn Gly
145                 150                 155                 160

Gly Val Asp Asn Val Lys Cys Ser Gly Thr Asn Thr Pro Val Arg Ala
                165                 170                 175

Val Thr Glu Ala Ser Thr Ser Pro Ser Lys Cys Pro Gly Tyr Val Ala
            180                 185                 190

Thr Thr Thr Thr Pro Thr Thr Thr Pro Glu Phe Ile Pro Glu Thr
        195                 200                 205

Thr Thr Ser Pro Gln Pro Val Ile Thr Thr Gln Lys Pro Lys Pro Leu
    210                 215                 220

Trp Asn Phe Asn Cys Thr Ser Ile Gln Glu Arg Lys Asn Asp Gly Gly
225                 230                 235                 240

Asp Cys Gly Lys Pro Ala Cys Thr Thr Leu Leu Asn Cys Ala Asn Phe
                245                 250                 255

Leu Ser Cys Leu Cys Ser Thr Cys Ala Leu Cys Arg Lys Arg
```

<210> SEQ ID NO 50
<211> LENGTH: 810
<212> TYPE: DNA
<213> ORGANISM: Artificial Sequence
<220> FEATURE:
<223> OTHER INFORMATION: Synthetically generated oligonucleotide

<400> SEQUENCE: 50

```
atgtggatca agtggatcgc cacgctggtc gcctttggcg ccctggtgca aagtgcggta      60
gcatgtccct cgcagtgttc gtgcagaggg acatatgtgg actgtgatag cagaagcctc     120
gcgtctgtgc ctgcgggaat ccctaccacc acgcaagtgc tgtatttgta cagcaatcaa     180
atcacgaagc tcgaacccgg ggtgtttgac catctggtga atctgcaggg gctgtatttg     240
aacagcaaca agctaacagc tatacccgct ggggtgtttg acaaattgac cctgctcgct     300
ggtctgagtc tgcacgacaa ccaactgaag agcattccca ggggcgcctt tgacaacctc     360
aagagcctca ctcacatcta tctgttcaac aaccccctgg gactgcgagt gttcggacatc    420
ctctatctga gaactggat tgtacagcac gcaagcatcg tgaatccagg cagcggggga      480
gttgataacg tgaagtgctc tggtaccaat accccgtcc gtgcggtcac cgaggccagc      540
actagcccct cgaaatgccc aggctacgtt gctacgacca cgacgccgac gacgaccacg     600
cccgaattca tccctgagac caccacctcg ccgcagcccg tgatcacaac ccagaaaccc     660
aagcctctgt ggaatttcaa ctgcacctca attcaggaga ggaagaacga cggtggcgac     720
tgcggaaagc ccgcctgcac aactctccta aactgcgcga atttcctcag ctgcctctgc     780
tcgacctgcg ccctctgcag gaaacgttga                                      810
```

<210> SEQ ID NO 51
<211> LENGTH: 269
<212> TYPE: PRT
<213> ORGANISM: Artificial Sequence
<220> FEATURE:
<223> OTHER INFORMATION: Synthetically generated peptide

<400> SEQUENCE: 51

```
Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Arg Gly Thr Tyr
            20                  25                  30

Val Asp Cys Asp Ser Arg Ser Leu Ala Ser Val Pro Ala Gly Ile Pro
        35                  40                  45

Thr Thr Thr Gln Val Leu Tyr Leu Tyr Ser Asn Gln Ile Thr Lys Leu
    50                  55                  60

Glu Pro Gly Val Phe Asp His Leu Val Asn Leu Gln Gly Leu Tyr Leu
65                  70                  75                  80

Asn Ser Asn Lys Leu Thr Ala Ile Pro Ala Gly Val Phe Asp Lys Leu
                85                  90                  95

Thr Leu Leu Ala Gly Leu Ser Leu His Asp Asn Gln Leu Lys Ser Ile
            100                 105                 110

Pro Arg Gly Ala Phe Asp Asn Leu Lys Ser Leu Thr His Ile Tyr Leu
        115                 120                 125

Phe Asn Asn Pro Trp Asp Cys Glu Cys Ser Asp Ile Leu Tyr Leu Lys
    130                 135                 140

Asn Trp Ile Val Gln His Ala Ser Ile Val Asn Pro Gly Ser Gly Gly
145                 150                 155                 160
```

```
Val Asp Asn Val Lys Cys Ser Gly Thr Asn Thr Pro Val Arg Ala Val
                165                 170                 175

Thr Glu Ala Ser Thr Ser Pro Ser Lys Cys Pro Gly Tyr Val Ala Thr
            180                 185                 190

Thr Thr Thr Pro Thr Thr Thr Thr Pro Glu Phe Ile Pro Glu Thr Thr
        195                 200                 205

Thr Ser Pro Gln Pro Val Ile Thr Thr Gln Lys Pro Lys Pro Leu Trp
    210                 215                 220

Asn Phe Asn Cys Thr Ser Ile Gln Glu Arg Lys Asn Asp Gly Gly Asp
225                 230                 235                 240

Cys Gly Lys Pro Ala Cys Thr Thr Leu Leu Asn Cys Ala Asn Phe Leu
                245                 250                 255

Ser Cys Leu Cys Ser Thr Cys Ala Leu Cys Arg Lys Arg
                260                 265
```

<210> SEQ ID NO 52
<211> LENGTH: 810
<212> TYPE: DNA
<213> ORGANISM: Artificial Sequence
<220> FEATURE:
<223> OTHER INFORMATION: Synthetically generated oligonucleotide

<400> SEQUENCE: 52

```
atgtggatca agtggatcgc cacgctggtc gcctttggcg ccctggtgca agtgcggta      60
gcatgtccct cgcagtgttc gtgctcaggg acaactgtgg attgtagtgg aaaagcctc    120
gcatctgtgc ctgcggcaat ccctatcacc acgcaaaggc tgtggttgag caacaatcag   180
ttaactaagc tcgaccccgg agtgtttgac agcctggtga atctgcagca gctgtggtta   240
gaaatcaacc agctgacatc tctccccgca ggggtgtttg acaaattgac cctgctcgct   300
ggtctgagtc tgcacgacaa ccaactgaag agtattccca ggggcgcctt tgacaacctc   360
aagagcctca ctcacatctg gctgtacaac aaccccctggg actgcgagtg ttcggacatc   420
ctctatctga gaactggat tgtacagcac gcaagcatcg tgaatccagg cagcggggga   480
gttgataacg tgaagtgctc tggtaccaat accccgtcc gtgcggtcac cgaggccagc   540
actagcccct cgaaatgccc aggctacgtt gctacgacca cgacgccgac gacgaccacg   600
cccgaattca tccctgagac caccacctcg ccgcagcccg tgatcacaac ccagaaaccc   660
aagcctctgt ggaatttcaa ctgcacctca attcaggaga ggaagaacga cggtggcgac   720
tgcggaaagc ccgcctgcac aactctccta aactgcgcga atttcctcag ctgcctctgc   780
tcgacctgcg ccctctgcag gaaacgttga                                   810
```

<210> SEQ ID NO 53
<211> LENGTH: 269
<212> TYPE: PRT
<213> ORGANISM: Artificial Sequence
<220> FEATURE:
<223> OTHER INFORMATION: Synthetically generated peptide

<400> SEQUENCE: 53

```
Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Ser Gly Thr Thr
            20                  25                  30

Val Asp Cys Ser Gly Lys Ser Leu Ala Ser Val Pro Ala Ala Ile Pro
        35                  40                  45
```

```
Ile Thr Thr Gln Arg Leu Trp Leu Ser Asn Asn Gln Leu Thr Lys Leu
     50                  55                  60
Asp Pro Gly Val Phe Asp Ser Leu Val Asn Leu Gln Gln Leu Trp Leu
 65                  70                  75                  80
Glu Ile Asn Gln Leu Thr Ser Leu Pro Ala Gly Val Phe Asp Lys Leu
                 85                  90                  95
Thr Leu Leu Ala Gly Leu Ser Leu His Asp Asn Gln Leu Lys Ser Ile
            100                 105                 110
Pro Arg Gly Ala Phe Asp Asn Leu Lys Ser Leu Thr His Ile Trp Leu
        115                 120                 125
Tyr Asn Asn Pro Trp Asp Cys Glu Cys Ser Asp Ile Leu Tyr Leu Lys
    130                 135                 140
Asn Trp Ile Val Gln His Ala Ser Ile Val Asn Pro Gly Ser Gly Gly
145                 150                 155                 160
Val Asp Asn Val Lys Cys Ser Gly Thr Asn Thr Pro Val Arg Ala Val
                165                 170                 175
Thr Glu Ala Ser Thr Ser Pro Ser Lys Cys Pro Gly Tyr Val Ala Thr
            180                 185                 190
Thr Thr Thr Pro Thr Thr Thr Pro Glu Phe Ile Pro Glu Thr Thr
        195                 200                 205
Thr Ser Pro Gln Pro Val Ile Thr Thr Gln Lys Pro Lys Pro Leu Trp
    210                 215                 220
Asn Phe Asn Cys Thr Ser Ile Gln Glu Arg Lys Asn Asp Gly Gly Asp
225                 230                 235                 240
Cys Gly Lys Pro Ala Cys Thr Thr Leu Leu Asn Cys Ala Asn Phe Leu
                245                 250                 255
Ser Cys Leu Cys Ser Thr Cys Ala Leu Cys Arg Lys Arg
            260                 265

<210> SEQ ID NO 54
<211> LENGTH: 807
<212> TYPE: DNA
<213> ORGANISM: Artificial Sequence
<220> FEATURE:
<223> OTHER INFORMATION: Synthetically generated oligonucleotide

<400> SEQUENCE: 54
atgtggatca agtggatcgc cacgctggtc gcctttggcc ctggtgcaaa gtgcggtaga      60
tgtccctcgc agtgttcgtg ctcagggaca caagtgaact gccatgagag aagactcgcg     120
tctgtgcctg cgggaatccc caccaccacg caagttctgt atttgtacac caataagatc     180
acgaagctcg agcccggcgt gtttgacagt ctgacgcaac tgactgttct gaatctcgca     240
ataaaccagc tgacggctct acccgctggg gtgtttgaca aactgaccaa actcactcat     300
ctggctctgc acatcaatca actgaagagc gtgcccaggg gcgcctttga caacctcaag     360
agcctcactc acatctatct gttcaacaac ccctgggact cgagtgttc ggacatcctc      420
tatctgaaga actggattgt acagcacgca agcatcgtga atccaggcag cggggagtt      480
gataacgtga agtgctctgg taccaatacc cccgtccgtg cggtcaccga ggccagcact     540
agccctcga aatgcccagg ctacgttgct cgaccacga cgccgacgac gaccacgccc       600
gaattcatcc ctgagaccac cacctcgccg cagcccgtga tcacaaccca gaaacccaag     660
cctctgtgga atttcaactg cacctcaatt caggagagga agaacgacgg tggcgactgc     720
ggaaagcccg cctgcacaac tctcctgaac tgcgcgaatt cctcagctg cctctgctcg     780
acctgcgccc tctgcaggaa acgttga                                         807
```

<210> SEQ ID NO 55
<211> LENGTH: 268
<212> TYPE: PRT
<213> ORGANISM: Artificial Sequence
<220> FEATURE:
<223> OTHER INFORMATION: Synthetically generated peptide

<400> SEQUENCE: 55

```
Met Trp Ile Lys Trp Ile Ala Thr Leu Val Ala Phe Gly Pro Gly Ala
 1               5                  10                  15

Lys Cys Gly Arg Cys Pro Ser Gln Cys Ser Cys Ser Gly Thr Gln Val
            20                  25                  30

Asn Cys His Glu Arg Arg Leu Ala Ser Val Pro Ala Gly Ile Pro Thr
        35                  40                  45

Thr Thr Gln Val Leu Tyr Leu Tyr Thr Asn Lys Ile Thr Lys Leu Glu
    50                  55                  60

Pro Gly Val Phe Asp Ser Leu Thr Gln Leu Thr Val Leu Asn Leu Ala
65                  70                  75                  80

Ile Asn Gln Leu Thr Ala Leu Pro Ala Gly Val Phe Asp Lys Leu Thr
                85                  90                  95

Lys Leu Thr His Leu Ala Leu His Ile Asn Gln Leu Lys Ser Val Pro
            100                 105                 110

Arg Gly Ala Phe Asp Asn Leu Lys Ser Leu Thr His Ile Tyr Leu Phe
        115                 120                 125

Asn Asn Pro Trp Asp Cys Glu Cys Ser Asp Ile Leu Tyr Leu Lys Asn
    130                 135                 140

Trp Ile Val Gln His Ala Ser Ile Val Asn Pro Gly Ser Gly Gly Val
145                 150                 155                 160

Asp Asn Val Lys Cys Ser Gly Thr Asn Thr Pro Val Arg Ala Val Thr
                165                 170                 175

Glu Ala Ser Thr Ser Pro Ser Lys Cys Pro Gly Tyr Val Ala Thr Thr
            180                 185                 190

Thr Thr Pro Thr Thr Thr Thr Pro Glu Phe Ile Pro Glu Thr Thr Thr
        195                 200                 205

Ser Pro Gln Pro Val Ile Thr Thr Gln Lys Pro Lys Pro Leu Trp Asn
    210                 215                 220

Phe Asn Cys Thr Ser Ile Gln Glu Arg Lys Asn Asp Gly Gly Asp Cys
225                 230                 235                 240

Gly Lys Pro Ala Cys Thr Thr Leu Leu Asn Cys Ala Asn Phe Leu Ser
                245                 250                 255

Cys Leu Cys Ser Thr Cys Ala Leu Cys Arg Lys Arg
            260                 265
```

<210> SEQ ID NO 56
<211> LENGTH: 792
<212> TYPE: DNA
<213> ORGANISM: Artificial Sequence
<220> FEATURE:
<223> OTHER INFORMATION: Synthetically generated oligonucleotide

<400> SEQUENCE: 56

```
atgtggatca agtggatcgc cacgctggtc gcctttggcg ccctggtgca aagtgcggta      60
gcatgtccct cgcagtgttc gtgctcaggg acaactgtgg attgtagtgg gaaaagcctc     120
gcatctgtgc ctgcgggaat ccccaccacc acgcaagtgc tgtatttgta caccaatcag     180
atcacgaagc tcgagcccgg cgtgtttgac cgcctggtga atctgcagaa gctgtggttg     240
```

```
aacagcaacc agctgacctc tctccccgct ggggtgtttg acaaactgac ccagctcaat    300
catctgtttc tgaacaacaa ccagctgaag agcgttccca ggggcgcctt tgacaacctc    360
aagagcctca ctcagatctg gctgtacaac aacccctggg actgcgcttg ctcagacatc    420
ctctacctca gcggctggct gggccagcac gcagggaaag agcagggcca ggctgtctgc    480
tctggtacca ataccccgt ccgtgcggtc accgaggcca gcactagccc ctcgaaatgc    540
ccaggctacg ttgctacgac cacgacgccg acgacgacca cgcccgaatt catccctgag    600
accaccacct cgccgcagcc cgtgatcaca cccagaaac ccaagcctct gtggaatttc    660
aactgcacct caattcagga gaggaagaac gacggtggcg actgcggaaa gcccgcctgc    720
acaactctcc taaactgcgc gaatttcctc agctgcctct gctcgacctg cgccctctgc    780
aggaaacgtt ga                                                        792
```

<210> SEQ ID NO 57
<211> LENGTH: 263
<212> TYPE: PRT
<213> ORGANISM: Artificial Sequence
<220> FEATURE:
<223> OTHER INFORMATION: Synthetically generated peptide

<400> SEQUENCE: 57

```
Met Trp Ile Lys Trp Ile Ala Thr Leu Val Ala Phe Gly Ala Leu Val
1               5                   10                  15

Gln Ser Ala Val Ala Cys Pro Ser Gln Cys Ser Cys Ser Gly Thr Thr
            20                  25                  30

Val Asp Cys Ser Gly Lys Ser Leu Ala Ser Val Pro Ala Gly Ile Pro
        35                  40                  45

Thr Thr Thr Gln Val Leu Tyr Leu Tyr Thr Asn Gln Ile Thr Lys Leu
    50                  55                  60

Glu Pro Gly Val Phe Asp Arg Leu Val Asn Leu Gln Lys Leu Trp Leu
65                  70                  75                  80

Asn Ser Asn Gln Leu Thr Ser Leu Pro Ala Gly Val Phe Asp Lys Leu
                85                  90                  95

Thr Gln Leu Asn His Leu Phe Leu Asn Asn Gln Leu Lys Ser Val
            100                 105                 110

Pro Arg Gly Ala Phe Asp Asn Leu Lys Ser Leu Thr Gln Ile Trp Leu
        115                 120                 125

Tyr Asn Asn Pro Trp Asp Cys Ala Cys Ser Asp Ile Leu Tyr Leu Ser
    130                 135                 140

Gly Trp Leu Gly Gln His Ala Gly Lys Glu Gln Gly Gln Ala Val Cys
145                 150                 155                 160

Ser Gly Thr Asn Thr Pro Val Arg Ala Val Thr Glu Ala Ser Thr Ser
                165                 170                 175

Pro Ser Lys Cys Pro Gly Tyr Val Ala Thr Thr Thr Pro Thr Thr
            180                 185                 190

Thr Thr Pro Glu Phe Ile Pro Glu Thr Thr Thr Ser Pro Gln Pro Val
        195                 200                 205

Ile Thr Thr Gln Lys Pro Lys Pro Leu Trp Asn Phe Asn Cys Thr Ser
    210                 215                 220

Ile Gln Glu Arg Lys Asn Asp Gly Gly Asp Cys Gly Lys Pro Ala Cys
225                 230                 235                 240

Thr Thr Leu Leu Asn Cys Ala Asn Phe Leu Ser Cys Leu Cys Ser Thr
                245                 250                 255
```

Cys Ala Leu Cys Arg Lys Arg
         260

<210> SEQ ID NO 58
<211> LENGTH: 738
<212> TYPE: DNA
<213> ORGANISM: Artificial Sequence
<220> FEATURE:
<223> OTHER INFORMATION: Synthetically generated oligonucleotide

<400> SEQUENCE: 58

```
atgtggatca agtggatcgc cacgctggtc gcctttggcg ccctggtgca agtgcggta      60
gcatgtccct cgcagtgttc gtgctcaggg acacatgtga actgtgaacg gaaacgcctc    120
acgtctgtgc ctgcgggaat ccccaccacc acgcaaactc tgtgggggga cagtaatcag    180
atcacgaagc tcgagcccgg ggtgcttgac cgcctggtga atctgcaggg gttgggtctg    240
cagaacaacc agctgaagag cgttcccagg ggcgcgtttg ataacctcaa gagcctcact    300
cacatctggc tgttcggcaa ccctgggac tgcgaatgtt cggacatcct ctatctgaag    360
aactggattg tacagcacgc aagcatcgtg aatccaggca gcggggagt tgataacgtg    420
aagtgctctg gtaccaatac ccccgtccgt gcggtcaccg aggccagcac tagcccctcg    480
aaatgcccag ctacgttgc tacgaccacg acgccgacga cgaccacgcc cgaattcatc    540
cctgagacca ccacctcgcc gcagcccgtg atcacaaccc agaaacccaa gcctctgtgg    600
aatttcaact gcacctcaat tcaggagagg aagaacgacg gtggcgactg cggaaagccc    660
gcctgcacaa ctctcctaaa ctgcgcgaat tcctcagct gcctctgctc gacctgcgcc    720
ctctgcagga aacgttga                                                   738
```

<210> SEQ ID NO 59
<211> LENGTH: 245
<212> TYPE: PRT
<213> ORGANISM: Artificial Sequence
<220> FEATURE:
<223> OTHER INFORMATION: Synthetically generated peptide

<400> SEQUENCE: 59

Met Trp Ile Lys Trp Ile Ala Thr Leu Val Ala Phe Gly Ala Leu Val
 1               5                  10                  15

Gln Ser Ala Val Ala Cys Pro Ser Gln Cys Ser Cys Ser Gly Thr His
             20                  25                  30

Val Asn Cys Glu Arg Lys Arg Leu Thr Ser Val Pro Ala Gly Ile Pro
         35                  40                  45

Thr Thr Thr Gln Thr Leu Trp Gly Asp Ser Asn Gln Ile Thr Lys Leu
     50                  55                  60

Glu Pro Gly Val Leu Asp Arg Leu Val Asn Leu Gln Gly Leu Gly Leu
65                  70                  75                  80

Gln Asn Asn Gln Leu Lys Ser Val Pro Arg Gly Ala Phe Asp Asn Leu
                 85                  90                  95

Lys Ser Leu Thr His Ile Trp Leu Phe Gly Asn Pro Trp Asp Cys Glu
            100                 105                 110

Cys Ser Asp Ile Leu Tyr Leu Lys Asn Trp Ile Val Gln His Ala Ser
        115                 120                 125

Ile Val Asn Pro Gly Ser Gly Gly Val Asp Asn Val Lys Cys Ser Gly
    130                 135                 140

Thr Asn Thr Pro Val Arg Ala Val Thr Glu Ala Ser Thr Ser Pro Ser
145                 150                 155                 160

```
Lys Cys Pro Gly Tyr Val Ala Thr Thr Thr Pro Thr Thr Thr Thr
                165                 170                 175
Pro Glu Phe Ile Pro Glu Thr Thr Ser Pro Gln Pro Val Ile Thr
            180                 185                 190
Thr Gln Lys Pro Lys Pro Leu Trp Asn Phe Asn Cys Thr Ser Ile Gln
        195                 200                 205
Glu Arg Lys Asn Asp Gly Gly Asp Cys Gly Lys Pro Ala Cys Thr Thr
    210                 215                 220
Leu Leu Asn Cys Ala Asn Phe Leu Ser Cys Leu Cys Ser Thr Cys Ala
225                 230                 235                 240
Leu Cys Arg Lys Arg
            245
```

<210> SEQ ID NO 60
<211> LENGTH: 810
<212> TYPE: DNA
<213> ORGANISM: Artificial Sequence
<220> FEATURE:
<223> OTHER INFORMATION: Synthetically generated oligonucleotide

<400> SEQUENCE: 60

| | | | | | |
|---|---|---|---|---|---|
| atgtggatca | agtggatcgc | cacgctggtc | gcctttggcg | ccctggtgca | aagtgcggta | 60 |
| gcatgtccct | cgcagtgttc | gtgctcaggg | acagatgtta | actgtcatga | gagacgcttg | 120 |
| gcgtctgtgc | ctgcggaaat | ccccaccacc | acgaagatcc | tgcggctgta | catcaatcag | 180 |
| atcacgaagc | tcgagccagg | ggtgtttgat | agtctgacgc | aactgactta | tctgaacctt | 240 |
| gctgttaacc | agctgacggc | tcttcccgtt | ggggtgtttg | acaacctgac | ccagcttagc | 300 |
| atactgaata | tgcacaccaa | ccagctgaag | aacattccca | ggggcgcctt | tgacaacctc | 360 |
| aagagcctca | ctcacatcta | tctgttcaac | aaccccctggg | actgcgagtg | ttcggacatc | 420 |
| ctctatctga | agaactggat | tgtacagcac | gcaagcatcg | tgaatccagg | cagcggggga | 480 |
| gttgataacg | tgaagtgctc | tggtaccaat | accccgtcc | gtgcggtcac | cgaggccagc | 540 |
| actagcccct | cgaaatgccc | aggctacgtt | gctacgacca | cgacgccgac | gacgaccacg | 600 |
| cccgaattca | tccctgagac | caccacctcg | ccgcagcccg | tgatcacaac | ccagaaaccc | 660 |
| aagcctctgt | ggaatttcaa | ctgcacctca | attcaggaga | ggaagaacga | cggtggcgac | 720 |
| tgcggaaagc | ccgcctgcac | aactctccta | aactgcgcga | atttcctcag | ctgcctctgc | 780 |
| tcgacctgcg | ccctctgcag | gaaacgttga | | | | 810 |

<210> SEQ ID NO 61
<211> LENGTH: 269
<212> TYPE: PRT
<213> ORGANISM: Artificial Sequence
<220> FEATURE:
<223> OTHER INFORMATION: Synthetically generated peptide

<400> SEQUENCE: 61

```
Met Trp Ile Lys Trp Ile Ala Thr Leu Val Ala Phe Gly Ala Leu Val
  1               5                  10                  15
Gln Ser Ala Val Ala Cys Pro Ser Gln Cys Ser Cys Ser Gly Thr Asp
            20                  25                  30
Val Asn Cys His Glu Arg Arg Leu Ala Ser Val Pro Ala Glu Ile Pro
        35                  40                  45
Thr Thr Thr Lys Ile Leu Arg Leu Tyr Ile Asn Gln Ile Thr Lys Leu
    50                  55                  60
Glu Pro Gly Val Phe Asp Ser Leu Thr Gln Leu Thr Tyr Leu Asn Leu
```

```
                65                    70                    75                    80
Ala Val Asn Gln Leu Thr Ala Leu Pro Val Gly Val Phe Asp Asn Leu
                    85                    90                    95

Thr Gln Leu Ser Ile Leu Asn Met His Thr Asn Gln Leu Lys Asn Ile
                    100                   105                   110

Pro Arg Gly Ala Phe Asp Asn Leu Lys Ser Leu Thr His Ile Tyr Leu
                    115                   120                   125

Phe Asn Asn Pro Trp Asp Cys Glu Cys Ser Asp Ile Leu Tyr Leu Lys
                    130                   135                   140

Asn Trp Ile Val Gln His Ala Ser Ile Val Asn Pro Gly Ser Gly Gly
145                 150                   155                   160

Val Asp Asn Val Lys Cys Ser Gly Thr Asn Thr Pro Val Arg Ala Val
                    165                   170                   175

Thr Glu Ala Ser Thr Ser Pro Ser Lys Cys Pro Gly Tyr Val Ala Thr
                    180                   185                   190

Thr Thr Thr Pro Thr Thr Thr Thr Pro Glu Phe Ile Pro Glu Thr Thr
                    195                   200                   205

Thr Ser Pro Gln Pro Val Ile Thr Thr Gln Lys Pro Lys Pro Leu Trp
        210                 215                   220

Asn Phe Asn Cys Thr Ser Ile Gln Glu Arg Lys Asn Asp Gly Gly Asp
225                 230                   235                   240

Cys Gly Lys Pro Ala Cys Thr Thr Leu Leu Asn Cys Ala Asn Phe Leu
                    245                   250                   255

Ser Cys Leu Cys Ser Thr Cys Ala Leu Cys Arg Lys Arg
                260                 265
```

METHODS AND COMPOSITIONS RELATED TO SOLUBLE MONOCLONAL VARIABLE LYMPHOCYTE RECEPTORS OF DEFINED ANTIGEN SPECIFICITY

CROSS-REFERENCE TO RELATED APPLICATIONS

This application is a continuation of U.S. patent application Ser. No. 12/375,804, filed Apr. 28, 2009, which is a filing under 35 U.S.C. § 371 based on PCT/US2007/074620, filed Jul. 27, 2007, which claims priority to U.S. Ser. No. 60/835,033, filed Aug. 2, 2006, each of which is incorporated by reference herein in their entirety.

BACKGROUND OF THE INVENTION

Jawless vertebrates were recently demonstrated to have antigen specific receptors called variable lymphocyte receptors (VLRs). These VLRs play a role in adaptive immunity but are distinctly different from immunoglobulin-type antigen receptors found in jawed vertebrates. VLRs are clonally diverse and comprise leucine-rich repeat (LRR) modules. VLRs were previously isolated from lampreys or hagfish and are known to have a GPI anchor and be membrane bound. However, no cell lines were available for large scale VLR production because of these characteristics.

SUMMARY OF THE INVENTION

As embodied and broadly described herein, the present application relates to antigen specific polypeptides and methods and compositions related thereto. The present application further relates to methods of making soluble, monoclonal VLRs. These methods are commercially useful for the large scale production of VLRs. Furthermore, provided herein are VLRs made by these methods, including, by way of example and not limitation, VLRs specific for pathogens like anthrax, HIV, and influenza and specific for carbohydrates such as blood group determinants. Further provided are antibodies to VLRs and nucleic acids that encode VLRs. Methods of using VLRs, encoding nucleic acids, and antibodies to VLRs are also disclosed.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and together with the description, serve to explain the principles of the VLRs and methods and compositions related thereto.

FIG. 1A is a Western blot of VLRs isolated from lamprey serum and VLRs isolated from culture medium. Blood was collected from lamprey larvae in the presence of EDTA as an anti-coagulant. Blood cells were pelleted by centrifugation at 1,000 g for 5 min, followed by removal of the plasma supernatant. The plasma was treated with the reducing agent 2-mercapto-ethanol (2-ME) or left untreated, then loaded onto SDS-PAGE gels (left panel). In the right panel of FIG. 1A, a cloned VLR cDNA was transfected into HEK-293T cells. Forty-eight hours after transfection, culture medium from the transfected cells was harvested and loaded onto SDS-PAGE gels with or without 2-ME pre-treatment. VLR expression was detected by Western blot with anti-VLR mAb (4C4). FIG. 1B is a model of a multivalent VLR.

Figure 2:
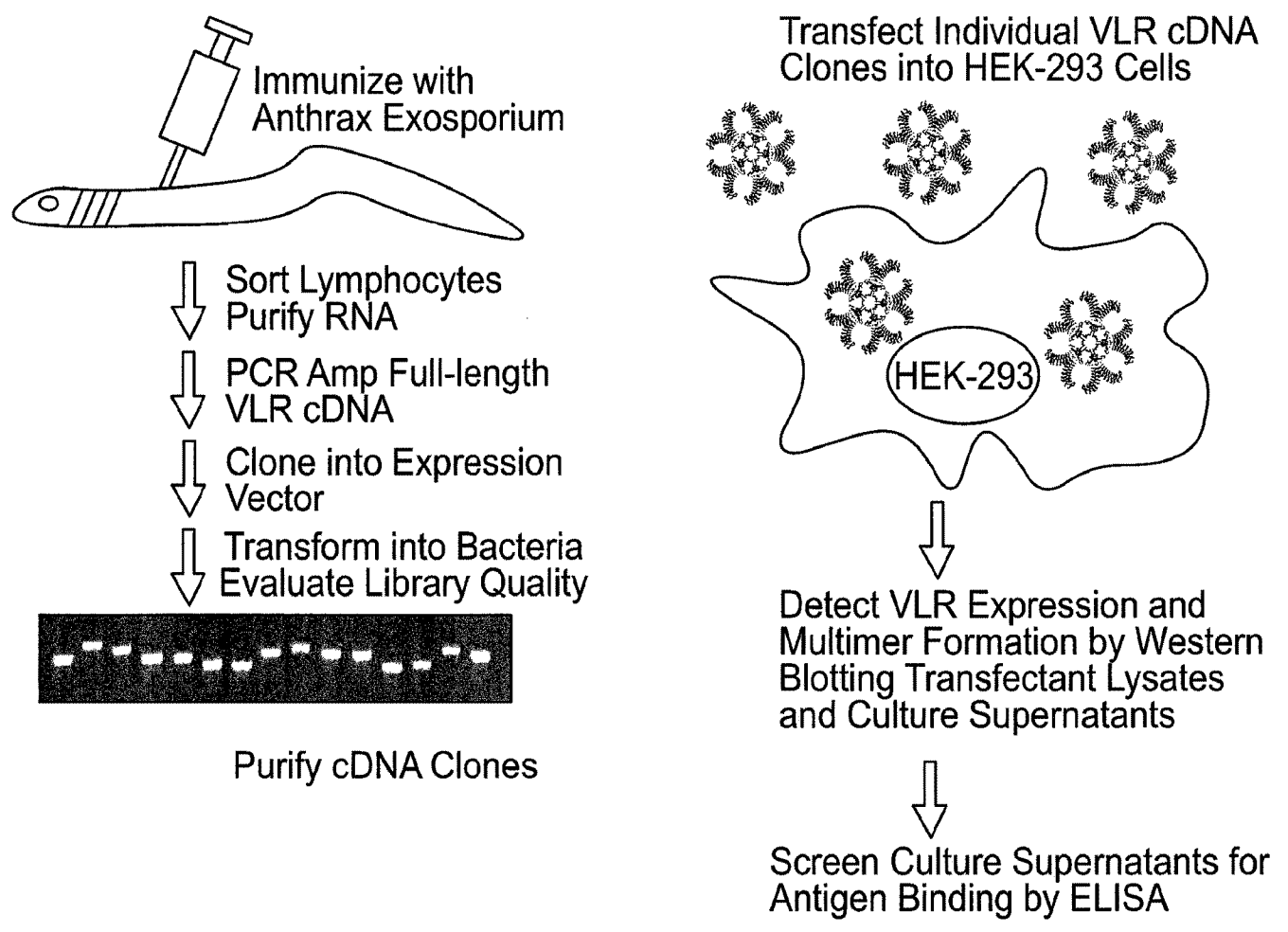

FIG. 2 is a schematic of the method for making antigen-specific VLRs.

FIG. 3A shows the results using detergent soluble lysates prepared from transfected HEK-293 cells treated with 2-mercaptoethanol before loading onto SDS-PAGE gels. FIGS. 3B and 3C are Western blots of supernatants removed from VLR transfectants 48 hours after transfection, then loaded directly onto SDS-PAGE gels (B) or pre-treated with 2-mercaptonethanol (C). VLR expression was detected by Western blotting with anti-VLR mAb (4C4).

FIG. 4 is a bar graph identifying the specificity of binding of several VLRs. Culture supernatants from VLR transfected HEK-293 cells were incubated in 96-well plates coated with the indicated antigens. VLR binding was detected with anti-VLR mAb (4C4) followed by AP conjugated goat anti-mouse-Ig secondary antibody.

FIG. 9D shows sequence alignment of BclA-CTD from *B. anthracis* (SEQ ID NO: 1) and *B. cereusT* (SEQ ID NO:2). Solvent exposed amino acid differences are shaded black, buried amino acid differences are shaded gray. FIG. 9E shows surface representation of *B. anthracis* BclA-CTD tertiary structure. Differences in amino acid sequence between *B. anthracis* and *B. cereus* are shaded black.

In FIG. 10A, supernatant from VLR4 transfected HEK-293T cells were incubated with BclA-CTD-conjugated sepharose beads, then washed and tested for elution with the indicated conditions (TEA=triethylamine, EtGlycol=ethylene glycol). VLR4 elution was detected by Western blotting with anti-VLR-B mAb (4C4). In FIG. 10B, for large scale purification, VLR4 was purified from stable transfectant supernatant by BclA-CTD affinity purification and eluted with triethylamine pH11.5. Purified VLR4 was separated by non-reducing 8% SDS-PAGE and detected with Gelcode blue staining. In FIG. 10C, the relative migration of purified recombinant VLR4 and high molecular weight protein standards (Amersham Biosciences) in 5, 6, 7, 8, 10, and 12% native polyacrylamide gels were measured and used to construct Ferguson plots to estimate the molecular weight of multimeric VLR4. In FIG. 10D, monomers, dimers, and oligomers were detected by Western blotting VLR4-containing supernatant under partial reducing conditions.

In FIG. 11A, supernatants from VLR4 wild-type (WT) and GPI-stop transfected HEK-293T cells were separated on a non-reducing 10% SDS-PAGE gel and Western blotted with anti-VLR mAb (4C4) followed by HRP-conjugated goat anti-mouse polyclonal Ab. In FIG. 11B, VLR4 was purified from HEK-293T cell supernatant, separated by reducing SDS-PAGE, Gel-code blue stained, and excised by scalpel. The excised VLR4 band was alkylated by iodoacetamide and digested with trypsin. The tryptic peptides were separated by RP-HPLC and analyzed by ESI-MS/MS. Y-ions are indicated on mass spectrum. FIG. 11C is a schematic of VLR4 WT and GPI-stop constructs. GPI cleavage site is shown in italics and indicated by an arrow. Tryptic peptide identified by MS/MS is indicated by a black line above the sequence (SEQ ID NO:40). FIG. 11D is a graph showing results of ELISA of VLR4 WT and GPI-stop binding to BclA-1-island coated plates.

FIGS. 12A-C show modulation of VLR5 avidity by site-directed mutagenesis of hypervariable amino acids on the concave surface. FIG. 12A is a multiple sequence alignment of high avidity (vBA41 (SEQ ID NO:41), vBA191 (SEQ ID NO:42), and VLR4 (SEQ ID NO:43)) and low avidity (VLR5 (SEQ ID NO:44)) anti-Bcla-CTD VLR-B antibodies. Hypervariable positions are in the boxes, VLR5 amino acids that differ from consensus residues utilized by high avidity VLR-B antibodies are shaded with a certain pattern if they reside in hypervariable positions. Sequence differences outside of hypervariable positions are shaded grey. FIG. 12B is a model of the concave surface of VLR5. Discrepancies in amino acids utilized by VLR5 versus the consensus of the high avidity anti-BclA-CTD VLR-B antibodies are shaded with the same pattern as in A. For example, the pattern over the H at position 13 in FIG. 12A corresponds to the circles shaded with the same pattern in FIG. 12B. The pattern over the Y at position 34 in FIG. 12A corresponds to the circles shaded with the same pattern in FIG. 12B. The pattern over the T at position 37 in FIG. 12A corresponds to the circles shaded with the same pattern in FIG. 12B. The pattern over the Q at position 80 in FIG. 12A corresponds to the circles shaded with the same pattern in FIG. 12B. The pattern over the S at position 82 in FIG. 12A corresponds to the circles shaded with the same pattern in FIG. 12B. The pattern over the W at position 106 in FIG. 12A corresponds to the circles shaded with the same pattern in FIG. 12B. In FIG. 12C, the relative avidity of VLR-B antibodies were measured by surface plasmon resonance (BiaCore 3000). BclA-1-island was covalently conjugated to a Biacore CM5 chip, then VLR transfectant supernatants, normalized for protein expression, were flowed over the chip. The chip was regenerated after each binding cycle with triethylamine pH 11.5.

FIG. 14A shows hemagglutinin responses of animals immunized with increasing numbers of human O erythrocytes. Blood samples were obtained before and 28 days after immunizations; immunization was on days 1 and 14. FIG. 14B shows hemagglutination titers before and after plasma adsorption with beads coated with a monoclonal anti-VLR-B or a control antibody. Error bars indicate standard error of the mean. FIG. 14C shows flow cytometric analysis comparing H antigen reactivity of plasma from immunized lamprey versus an anti-H monoclonal mouse antibody; staining is shown for α1,2-fucosyltransferase CHO cell transfectants expressing the H antigen. No reactivity was observed for non-transfected CHO cells. FIG. 14D shows that depletion of H antigen-specific VLR antibodies by adsorption with H antigen-bearing CHO cells removes hemagglutinating activity from plasma. Depletion of H antigen-reactive VLRs has little effect on the VLR plasma level.

FIGS. 15A and B show recombinant VLR antibody specificity for the H antigen. In FIG. 15A, CHO cells transfected with α1,2-fucosyltransferase to produce the H antigen or vector alone transfected cells were stained with anti-H mAb or supernatant from HEK 293T cells transfected with VLR-B specific for the H antigen. Gray represents unstained cells and black with no fill represents cells stained with mAb or VLR antibodies. FIG. 15B shows a Western blot of lamprey plasma before and after treatment with 2-mercaptoethanol to reduce disulfide bonds.

FIGS. 16A-C show VLR antibody response to immunization with *B. anthracis* exosporium. Plasma samples from immunized (black bars) and unimmunized (white bars) lamprey were assayed by ELISA. FIG. 16A shows evaluation of antigen dose requirement. VLR antibody response to BclA before (x) and after two intraperitoneal immunizations with 1 (♦), 0.1 (■) or 0.01 (▲)µg of *B. anthracis* exosporium. Booster immunizations were given after two weeks and plasma samples were obtained at four weeks. FIG. 16B shows that the VLR antibody response is directed toward the C terminal domain of the spore coat protein BclA (BslA-CTD). FIG. 16C shows the specificity of VLR antibodies for

*B. anthracis* spore coat protein BclA after two immunizations with anthrax exosporium (1 µg). Error bars indicate standard error of the mean.

Figure 17A:
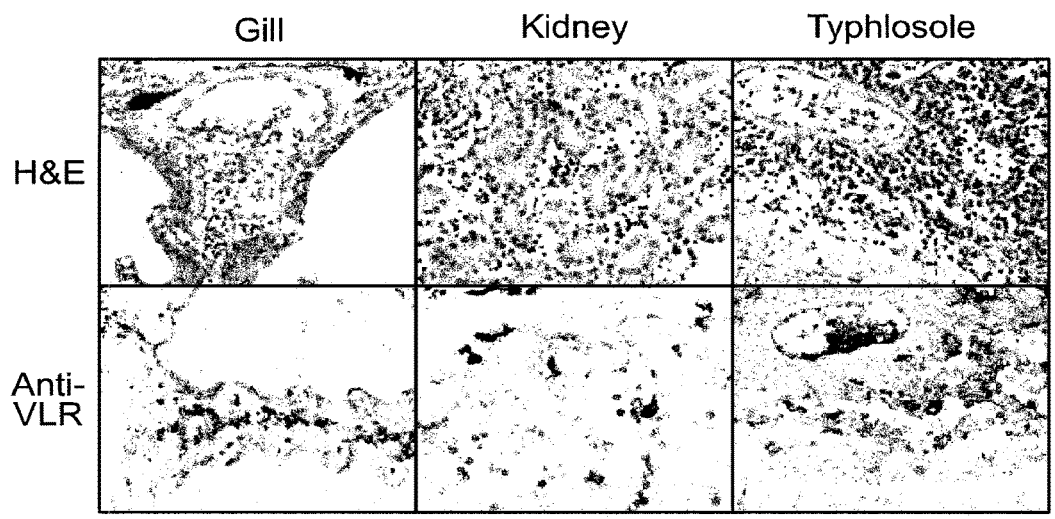
Figure 17B:
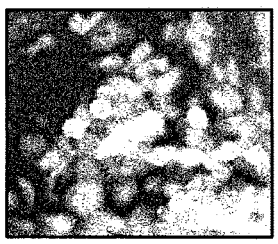
Figure 17D:
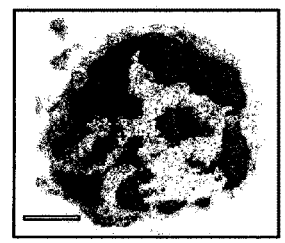
Figure 17C:
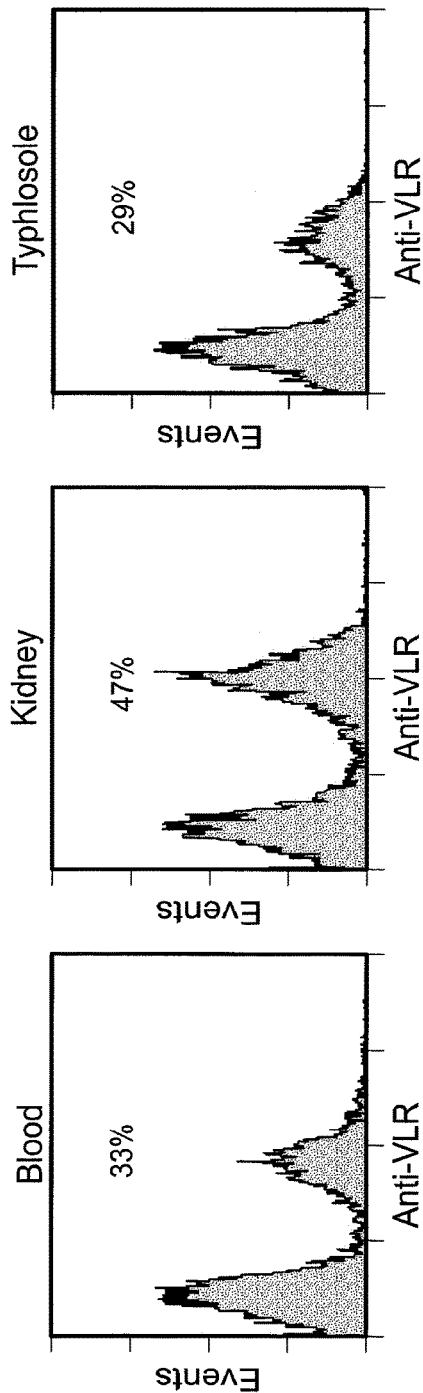

FIGS. 17A-D show tissue distribution of VLR+ lymphocytes. FIG. 17A shows immunohistochemical analysis of VLR-B+ cells in different organs. Paraffin sections were stained with hematoxylin and eosin (top) or anti-VLR mAb using DAB as a chromogen (bottom). FIG. 17B shows immunofluorescence identification of VLR-B+ lymphocytes within a large blood vessel of the gill region (corresponds with large blood vessel at gill base in top left panel of A). FIG. 17C shows immunofluorescence analysis of VLR expression by lymphocytes from blood, kidney, and typhlosole. Histograms depict analysis of cells in the 'lymphocyte gate' isolated from different tissues. FIG. 17D shows transmission electron microscopy (EM) of VLR-B+ and VLR-B– cells sorted from 'lymphocyte gate' of blood sample: photomicrographs of resting VLR+ lymphocyte (top) and thrombocyte with characteristic nuclear cleft (bottom).

Figure 18:
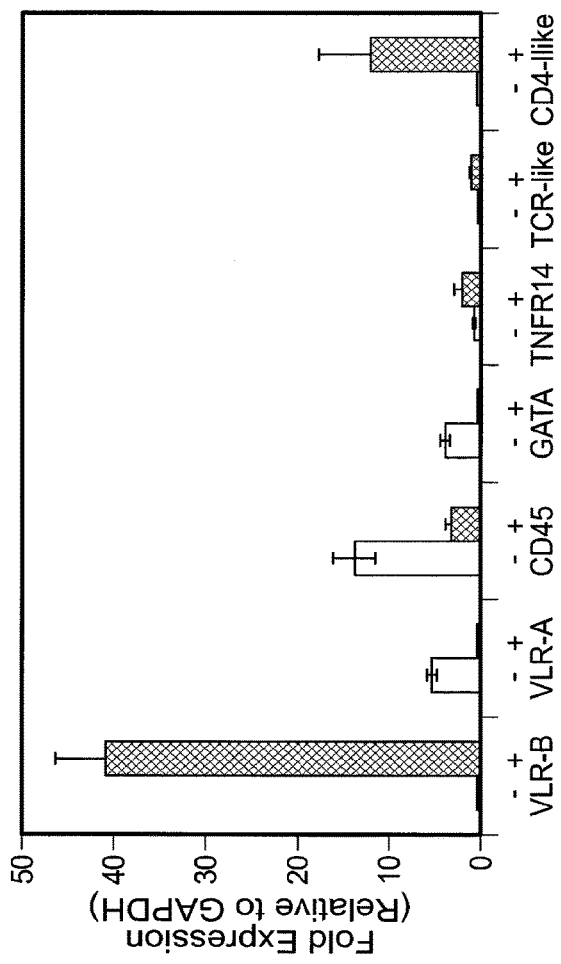

FIG. 18 is a graph showing the gene expression profile for VLR-B+ and VLR-B– lymphocyte populations. Quantitative PCR analysis of VLR-B+ and VLR-B cells isolated by fluorescence activated cell sorting of cells in 'lymphocyte gate'.

Figure 19A:
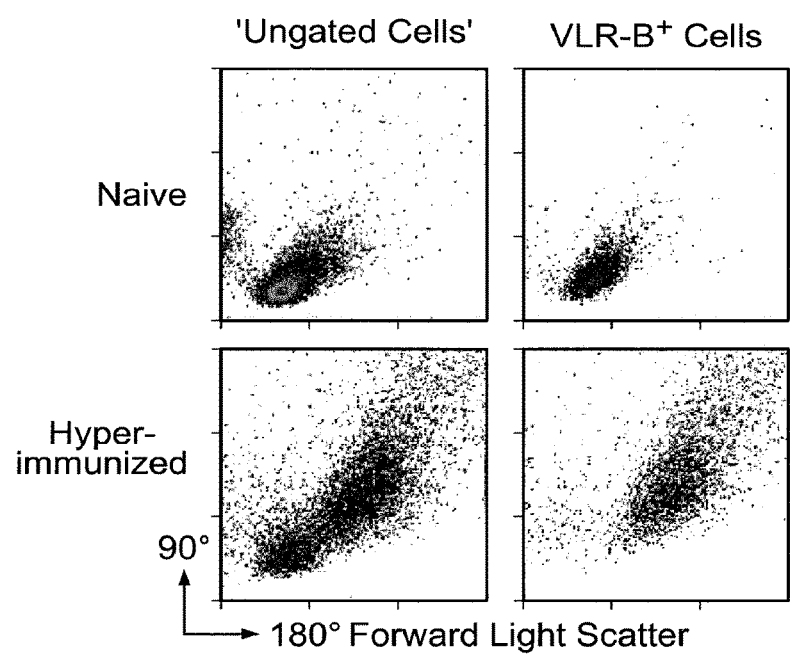
Figure 19B:
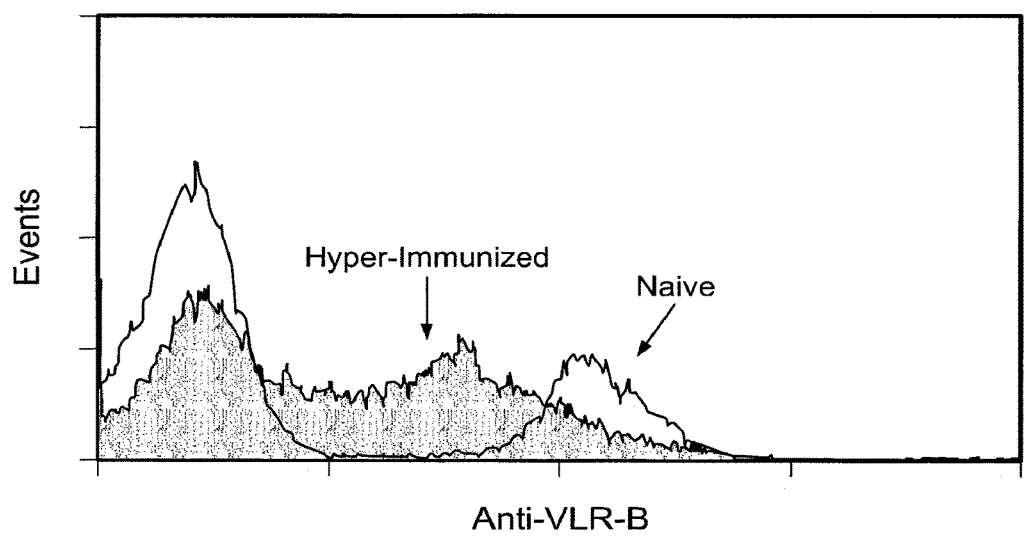

FIGS. 19A and 19B show lymphoblastoid response of VLR-B+ lymphocytes in lamprey hyperimmunized with anthrax exosporium. FIG. 19A shows flow cytometric analysis of forward and side light scatter characteristics of ungated blood leukocytes versus VLR-B+ cells. Blood samples were from animals 14 days after booster injection of a super-immunogenic dose of *B. anthracis* exosporium (>25 µg).

FIG. 19B shows cell surface expression of VLR-B. There was a decrease in VLR-B expression levels following hyper immunization with anthrax exosporium.

Figure 20A:
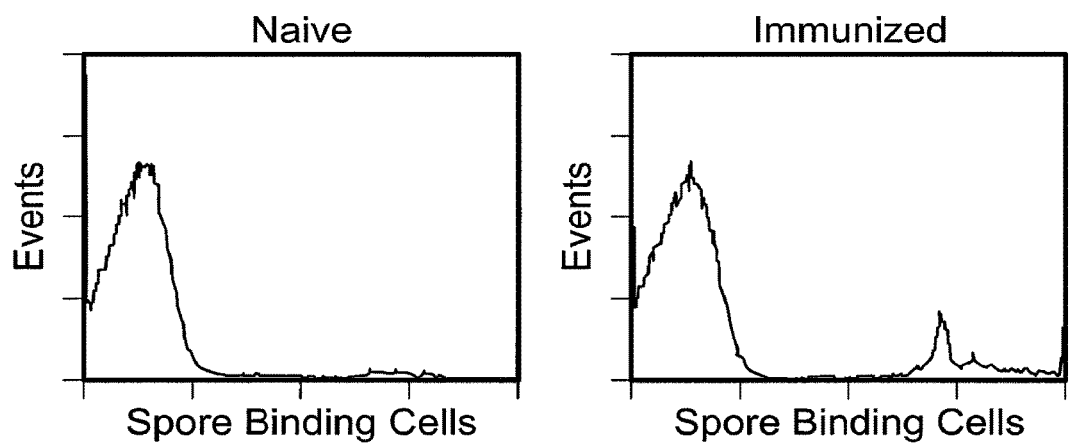
Figure 20B:
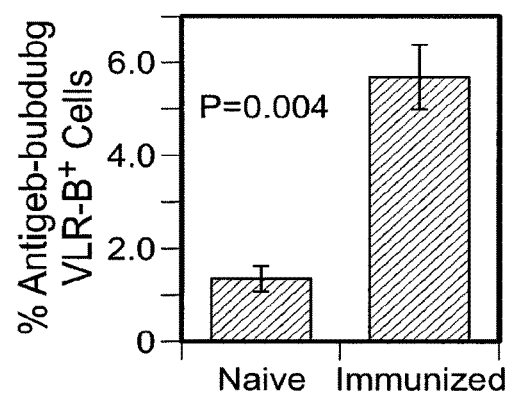

FIGS. 20A and 20B show analysis of the frequency of antigen binding VLR-B+ cells before and after immunization with *B. anthracis* exosporium. FIG. 20A shows flow cytometric analysis of VLR-B+ cells in blood samples from naive and immunized animals co-stained with 4C4 anti-VLR monoclonal antibody and fluorescent-tagged spores. FIG. 20B shows percentage of anthrax spore binding cells before and after (28 days) immunization with *B. anthracis* exosporium.

Figure 21A:
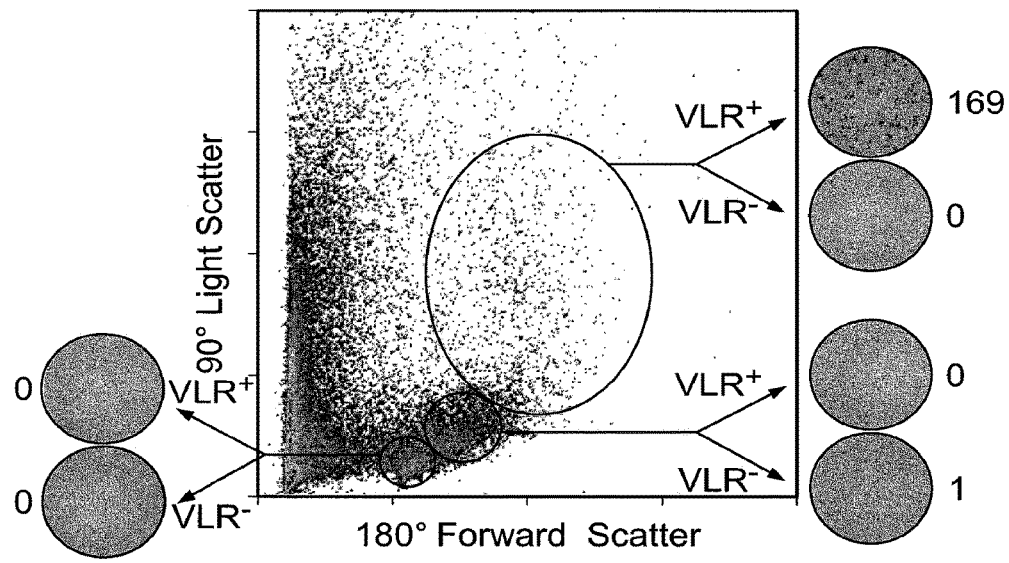
Figure 21B:
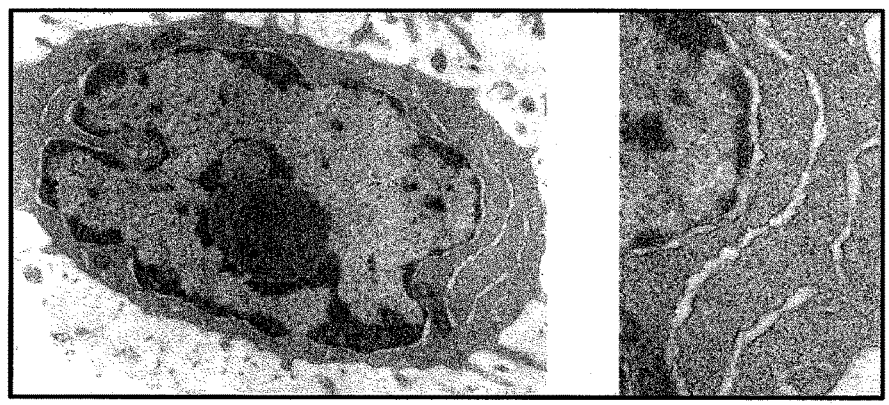

FIGS. 21A and 21B show characterization of VLR-B secreting cells induced by immunization with *B. anthracis* exosporium. Pooled cells were sorted from six 13 cm lamprey larvae 14 days after a booster immunization with 1 µg of exosporium. FIG. 21A shows ELISPOT assay of VLR-B antibody secreting cells among VLR-B+ and VLR-B– populations of cells with different light scatter characteristics. Cells secreting VLR-B antibodies specific for the BclA anthrax coat protein were found in the subpopulation of relatively large VLR-B bearing cells. FIG. 21B shows EM analysis of large VLR-B+ producing cells indicates their plasmacytoid morphology with expanded rough endoplasmic reticulum.

Figure 22:
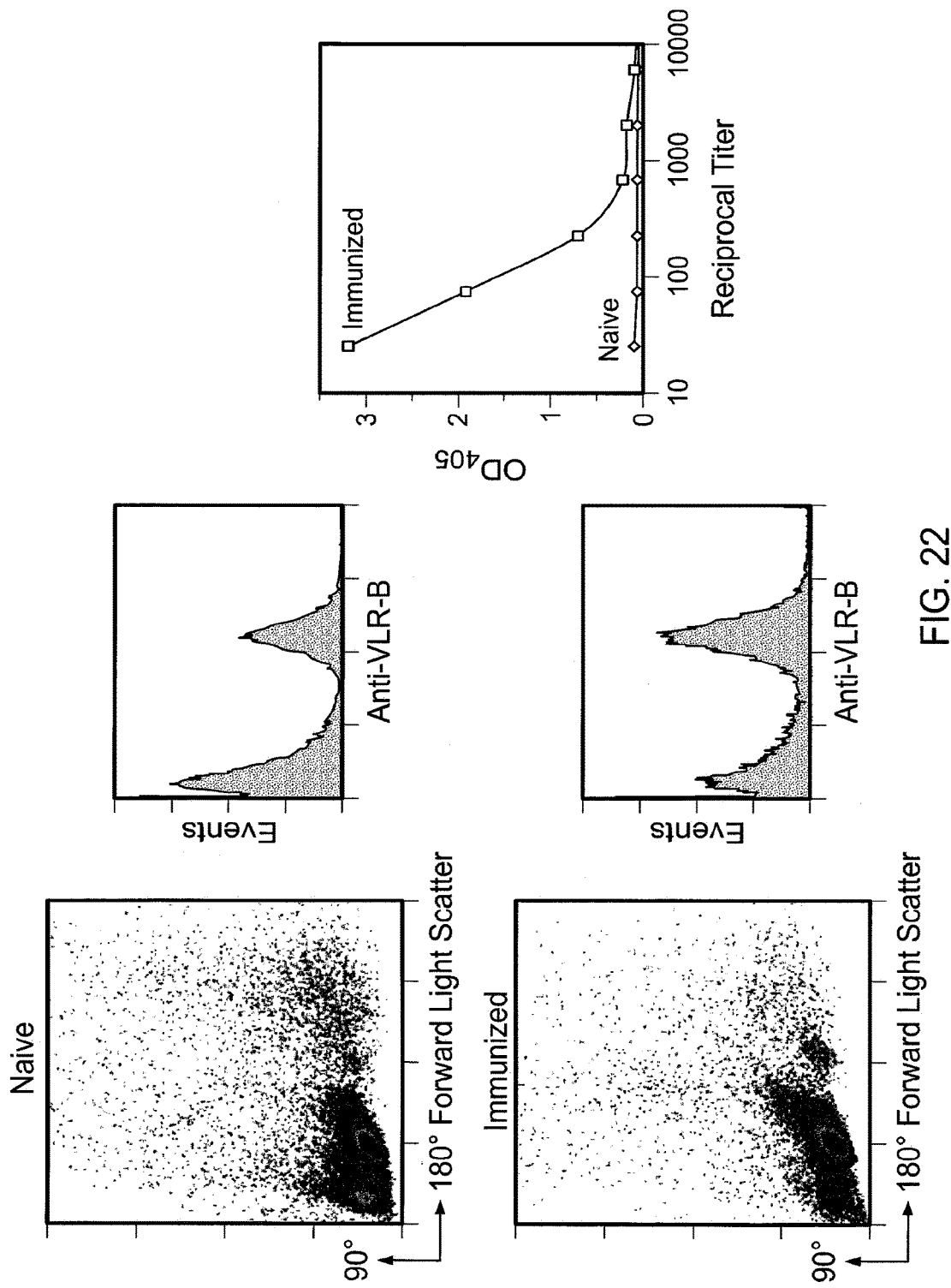

FIG. 22 shows comparison of naive and immunized lamprey following injection with non-mitogenic dose of anthrax exosporium. Immunized lamprey were injected twice with 1 µs of anthrax exosporium. This dose of anthrax dose not induce lymphoblastoid transformation but still generates a specific immune response to BclA-CTD.

Figure 23:
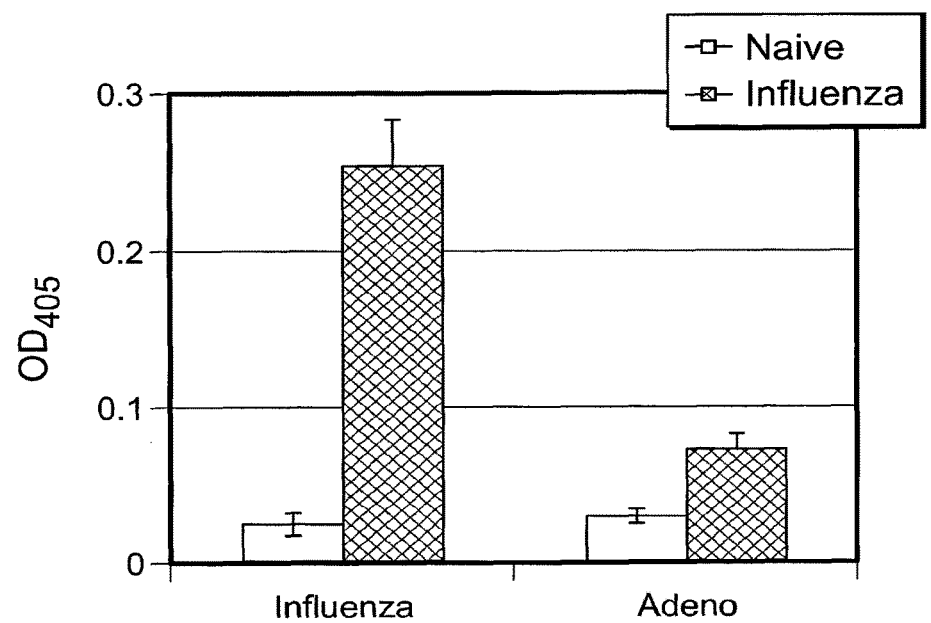

FIG. 23 shows that lamprey immunized with influenza virus produce VLRs specific for immunogen. ELISA assay performed with 1:50 dilution of lamprey plasma.

Figure 24:
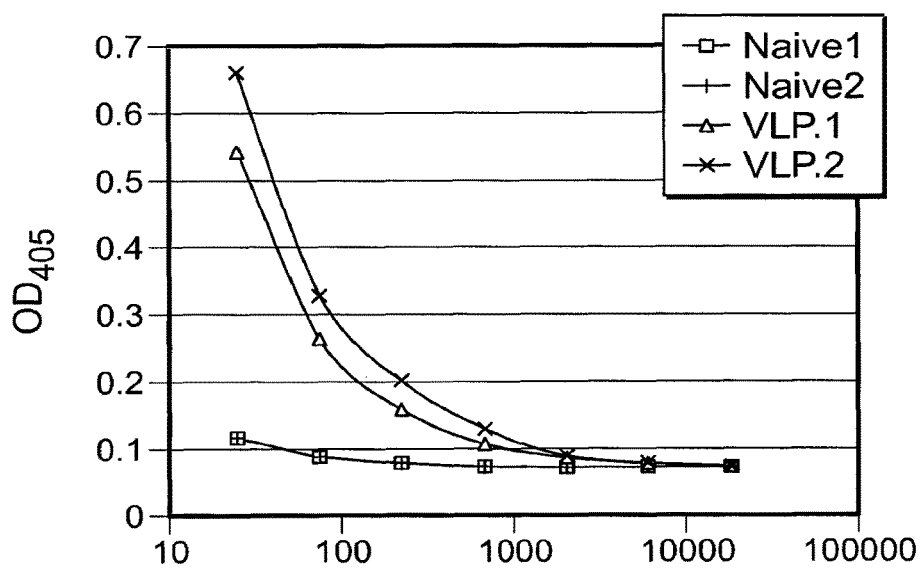

FIG. 24 shows that lamprey immunized with HIV virus like particles (VLPs) produce VLR-B antibodies specific for HIV envelope protein gp120 subunit. ELISA plates were coated with purified recombinant HIV gp120 overnight and then incubated with naive or HIV VLP immunized lamprey plasma. Gp120 binding VLR-B antibodies were detected with anti-VLR-B mAb (4C4) and alkaline phosphatase-conjugated goat anti-mouse IgG polyclonal antibody.

DETAILED DESCRIPTION

The adaptive immune system in jawless vertebrates is comprised of clonally diverse lymphocytes. They have been named V lymphocytes, because they express Variable Lymphocyte Receptors (VLRs) derived from the assembly of leucine-rich repeat (LRR) gene segments, rather than the immunoglobulin V, D, and J gene subunits utilized by jawed vertebrates. Two VLR genes, VLR-A and VLR-B, have been identified in lamprey and hagfish, the two extant representatives of the jawless vertebrates (agnathans). The germline VLR genes are incomplete in that they have coding regions only for the invariant N-terminal and C-terminal sequences separated by intervening sequences, lacking canonical splice sites. During development of cells of the lymphocyte lineage, flanking LRR modular units are sequentially inserted into the incomplete VLR gene with a concomitant deletion of the intervening sequences via a gene conversion mechanism to generate a mature VLR gene. The gene conversion process may be catalyzed by recently identified activation-induced deaminase/apolipoprotein B-editing catalytic protein (AID-APOBEC) family members with lymphocyte restricted expression.

VLR-B+ lymphocytes (VB cells) constitute a major component of the humoral arm of the lamprey adaptive immune system. As described herein, immunization of lamprey with particulate antigens, such as, for example, *B. anthracis* exosporium or human red blood cells, induces the differentiation of plasmacytoid cells and their secretion of antigen-specific VLR-B antibodies. Structural analysis of hagfish VLR-B lacking most of the stalk region confirmed the previous modeling prediction that the hypervariable amino acids are concentrated on the concave surface of the receptor to form a putative antigen binding site. Secreted VLR-B antibodies function analogously to antibodies in jawed vertebrates, whereby antigen stimulation results in secretion of VLR-B as an effector molecule, which binds to antigen and promotes clearance of infection, presumably by neutralization, opsonization, and other mechanisms.

Monoclonal antibodies are valuable research and therapeutic tools that take advantage of the remarkable ability of the jawed vertebrate adaptive immune system to recognize almost any foreign molecule. As described herein, the tremendous repertoire of diversity of the agnathan adaptive immune system can be exploited to produce soluble VLR-B clones of known specificity, with similar properties to monoclonal antibodies. Described herein is a method of producing soluble, recombinant monoclonal VLR-B antibodies of defined antigen specificity.

Provided herein is a scaleable method of making antigen specific polypeptides, and, more specifically, a method of making soluble, monoclonal antigen specific polypeptides such as VLRs. Also provided are compositions, including specific VLRs, multivalent VLRs, and antibodies to VLRs as well as methods of using the compositions.

The method of making a soluble, monoclonal antigen specific polypeptide comprises the steps of (1) isolating a cDNA clone encoding an antigen specific polypeptide, wherein the antigen specific polypeptide comprises an N-terminal leucine rich repeat (LRRNT), one or more leucine rich repeats (LRRs), a C-terminal leucine rich repeat (LRCCT), and a connecting peptide, wherein the connecting peptide comprises an alpha helix; (2) transfecting a cell with the cDNA clone in culture medium, wherein the cell proliferates; and (3) isolating the antigen specific polypeptide from the culture medium. Even more specifically, the method of making the antigen specific protein comprises (1) administering to a lamprey or hagfish a target antigen (e.g., a target carbohydrate, a target protein, a target pathogen, a target glycoprotein, a target lipid, a target glycolipid, etc.); (2) isolating an antigen specific protein-encoding RNA from lymphocytes of the lamprey or hagfish; (3) amplifying antigen specific protein encoding cDNA from the isolated RNA; (4) cloning the cDNA into an expression vector; (5) expressing the expression vector in a bacterium transformed with the expression vector; (6) isolating a cDNA clone; (7) transfecting a cultured cell with a the isolated cDNA clone; (8) screening the culture supernatant for an ability to bind the target antigen, and (9) isolating the antigen specific protein from the supernatant that binds the target antigen. The antigen can be administered in an amount sufficient to produce antigen-specific VLRs. For example, 0.01, 0.1, 1, 2, 5, 10, 15, 20, 25, 30, 35, 40, 45, 50, 75 or 100 µg or any amount in between 0.01 and 100 µs or more of antigen can be administered to the lamprey or hagfish.

Optionally, the isolated cDNA clone does not encode a sequence that prevents the formation of soluble VLRs. In the LRRCT region, approximately 50% of VLR clones contain: KNWIVQHASIVN-(P/L)-X-(S/Y/N/H)-GGVDNVK (SEQ ID NO:7) or KNWIVQHASIVN-(P/L)-XX-(S/Y/N/H)-GGVDNVK (SEQ ID NO: 8), where (P/L) means either P or L in that position, X means any amino acid and (S/Y/N/H) means either S, Y, N or H in that position. These sequences result in VLRs that are secreted and membrane bound. VLRs without SEQ ID NOs:7 or 8 are only membrane bound. SEQ ID NOs:7 or 8 can be mutated to prevent or reduce membrane anchoring in any cDNA clone that contains this sequence by methods known to those of ordinary skill in the art. Further provided are soluble, monoclonal antigen specific polypeptides made by the methods described herein. Thus, a soluble VLR contains SEQ ID NOs:7 or 8 or contains a mutation in SEQ ID NOs:7 or 8 that reduces or prevents membrane anchoring. A soluble VLR optionally lacks the transmembrane domain, the GPI anchor, the hydrophobic tail, the stalk region, or any combination of these regions.

A variable lymphocyte receptor or VLR is an antigen specific polypeptide having certain structural characteristics and functions. VLRs comprise 1-12 leucine rich repeats and have been shown to function in adaptive immunity. More particularly VLRs comprise an N-terminal leucine rich repeat (LRRNT), one or more leucine rich repeats (LRRs) (referred to herein as the internal LRRs), a C-terminal leucine rich repeat (LRRCT), and a connecting peptide, wherein the connecting peptide comprises an alpha helix. The length of the VLR can comprise as few as about 130 amino acids or as many as about 225 amino acids. Examples of the general structure and specific sequences of the polypeptides and encoding nucleic acids are provided in PCT/US2005/0179; Pancer and Cooper (2006) Annual Rev. Immunology 24:497-518, Alder et al (2005) Science 310: 1892-93; Pancer et al. (2005) P.N.A.S. 102 (9224-29) which are each incorporated herein by reference in their entireties for the VLRs and methods of using VLRs as taught therein. Furthermore, numerous examples of various regions (including the signal peptide, LRRNT, LRR, LRRCT, connecting peptide, stalk and hydrophobic tails) can be found in these references and the references are similarly incorporated by reference for the VLR regions.

Optionally, the connecting peptide of the VLR is located on the N-terminal side of the LRRCT, and more specifically located between an internal LRR and the LRRCT. The connecting peptide can be linked to an internal LRR and the LRRCT. Thus disclosed herein are VLRs comprising a LRRNT, one or more internal LRRs, a connecting peptide, and a LRRCT, in that order. Also disclosed are VLRs, wherein the internal LRR region between the LRRNT and the LRRCT comprises 1, 2, 3, 4, 5, 6, 7, 8, or 9 leucine rich repeats, with LRR 1 located adjacent to or closest to the LRRNT. As used herein LRRs 1, 2, 3, 4, 5, 6, 7, 8, or 9 are considered to run from the LRRNT to the LLRCT, consecutively. Thus, disclosed herein are VLRs comprising a LRRNT, 1, 1-2, 1-3, 1-4, 1-5, 1-6, 1-7, 1-8, or 1-9 LRRs, a connecting peptide, and a LRRCT, in that order.

Leucine rich repeats or LRRs are short sequence motifs typically involved in protein-protein interactions, wherein the LRRs comprise multiple leucine residues. LRRs contain leucine or other aliphatic residues, for example, at positions 2, 5, 7, 12, 16, 21, and 24. However, it is understood and herein contemplated that the leucine or other aliphatic residues can occur at other positions in addition to or in the place of residues at positions 2, 5, 7, 12, 16, 21, and 24. For example, a leucine can occur at position 3 rather than position 2. It is also understood that structurally, the LRR motifs form β-sheet structures. Thus, for example, a disclosed polypeptide comprising a LRRNT, 5 separate LRRs, a LRRCT, and a connecting peptide would comprise 7 β-sheet structures and the alpha helix of the connecting peptide.

It is understood that the length and sequence of each internal LRR can vary from the other internal LRRs in the VLR as well as from the LRRNT and LRRCT. For example, VLRs can comprise a LRRNT, 1 to 9 LRRs, a connecting peptide, and a LRRCT, wherein the first internal LRR is LRR1, and wherein LRR1 comprises less than about 20 amino acids. Also disclosed are VLRs, wherein LRR1 comprises about 18 amino acids. Optionally, the VLR further comprises LRRs 2 to 9, wherein LRRs 2 to 9 are less than about 25 amino acids each. Also disclosed are VLRs, wherein LRRs 2 to 9 comprise about 24 amino acids each. LRRs 1 to 9 can be the same or different from each other in a given VLR both in length and in specific amino acid sequence.

The terminal LRRs, designated LRRNT and LRRCT, are typically longer than each internal LRR. The LRRNT and LRRCT comprise invariant regions (regions that have little variation relative to the rest of the polypeptide as compared to similar variable lymphocyte receptors). The variable regions provide the receptors with specificity, but the invariant regions and general structural similarities across receptors help maintain the protective immunity functions. The VLR can comprise an LRRNT, wherein the LRRNT comprises less than about 40 amino acids. Thus the LRRNT optionally comprises the amino acid sequence CPSQCSC (SEQ ID NO:9), CPSRCSC (SEQ ID NO: 10), CPAQCSC (SEQ ID NO: 11), CPSQCLC (SEQ ID NO: 12), CPSQCPC (SEQ ID NO: 13), NGATCKK (SEQ ID NO: 14), or NEALCKK (SEQ ID NO: 15) in the presence or absence of one or more conservative amino acid substitutions.

Also disclosed are VLRs comprising a LRRCT, wherein the LRRCT is less than about 60 amino acids, and optionally from 40 to 60 amino acids in length. In particular, specifically disclosed are VLRs, wherein the LRRCT comprises the amino acid sequence TNTPVRAVTEASTSPSKCP (SEQ ID NO:16), SGKPVRSIICP (SEQ ID NO: 17), SSKAVLDVTEEEAAEDCV (SEQ ID NO: 18), or QSKAV-LEITEKDAASDCV (SEQ ID NO: 19) in the presence or absence of conservative amino acid substitutions.

Typically the connecting peptides of VLRs are short peptides less than 15 amino acids in length and comprise an alpha helix. Thus, for example, specifically disclosed are connecting peptides of 10, 11, 12, 13, 14, and 15 amino acids in length comprising an alpha helix. The connecting peptide serves to link structural components of the VLR, including to the LRRCT.

The VLRs described herein selectively bind an antigen or an agent, much as an antibody selectively binds an antigen or agent. By selectively binding or specifically binding is meant that the VLR binds one agent or antigen to the partial or complete exclusion of other antigens or agents. By binding is meant a detectable binding at least about 1.5 times the background of the assay method. For selective or specific binding such a detectable binding can be detected for a given antigen or agent but not for a control antigen or agent.

VLRs may be naturally occurring or non-naturally occurring. Fragments or variants of VLRs are described below wherein the fragment or variant retains the ability of the VLR to selectively bind an antigen or agent. Thus, VLR, like the term antibody, includes various versions having various specificities. VLRs are tested for their desired activity using the in vitro assays described herein, or by analogous methods, after which their therapeutic, diagnostic or other purification activities are tested according to known testing methods. For example, ELISA, dot blot, Western blot analysis, and other testing methods can be used to test activity and/or specificity. VLRs can be detected by direct labeling of the VLR or by using a secondary VLR or an antibody that binds VLRs, analogous to a secondary antibody, and wherein the antibody or secondary VLR are labeled directly or indirectly. Antibodies to VLR and labels are described in more detail below.

Provided herein is a multivalent protein comprising multiple antigen specific polypeptides, such as VLRs wherein each antigen specific polypeptide comprises a N-terminal leucine rich repeat (LRRNT), one or more leucine rich repeats (LRRs), a C-terminal leucine rich repeat (LRCCT), and connecting peptide, wherein the connecting peptide comprises an alpha helix. As used herein, the term LRR-1 refers to the first LRR following the LRRNT. As used herein, the term LRRV refers to LRR Variable, which is an LRR that follows the LRR-1 but comes before the LRRCT. As used herein, the term LRRV, refers to LRR Variable end, which is the last LRR that comes before the LRRCT. However, if the VLR contains an LRRNT, one LRR and the LRRCT. The LRR between the LRRNT and LRRCT is designated LRR-1. A schematic of a multivalent VLR is shown in FIG. 1. The multivalent protein comprises two to twelve (i.e., 2, 3, 4, 5, 6, 7, 8, 9, 10, 11, or 12) antigen specific polypeptides. The multivalent protein binds a target protein, a target carbohydrate, target glycoprotein, target proteoglycan, or a target pathogen. Multivalent proteins optionally are designed to bind a variety of target proteins, carbohydrates, glycoprotens, proteoglycans, pathogens, or any combination thereof. For example, a divalent protein can comprise a first and second antigen specific polypeptide, wherein the first antigen specific polypeptide selectively binds a first protein, carbohydrate, glycoprotein, proteoglycan, or pathogen and wherein the second antigen specific polypeptide selectively binds a second protein, carbohydrate, glycoprotein, proteoglycan, or pathogen. Similarly, a trivalent protein comprises a first, second, and third antigen specific polypeptide wherein each binds a different target; a tetravalent comprises a first, second, third and fourth antigen specific polypeptide wherein each binds a different target. As one example, a divalent protein comprises a first antigen specific polypeptide that binds the H blood group determinant and a second antigen specific polypeptide that binds the A or B group determinant. Preferably the multivalent protein and/or the antigen specific polypeptides are soluble.

Also provided herein are antigen specific polypeptides that bind a target carbohydrate, including, for example, a blood group determinant. The blood group determinant includes, for example, the A determinant, the B determinant, or the H determinant. By way of example, an antigen specific polypeptide that specifically binds the H determinant is provided. By way of further example, the antigen specific polypeptide that specifically binds the H determinant comprises the amino acid sequence of SEQ ID NO:20. Provided herein are nucleic acids that can encode the antigen specific polypeptide of SEQ ID NO:20, including, for example, SEQ ID NO:32. Other examples include nucleic acids that encode SEQ ID NO:20 with one or more conservative amino acid substitutions.

Antigen specific polypeptides that bind carbohydrates have many uses in identifying, quantifying, isolating, and imaging the target carbohydrate. By way of example, provided herein is a method of typing blood comprising contacting a blood sample with the antigen specific polypeptide that selectively binds a blood group determinant, wherein the antigen specific polypeptide is detectably labeled (directly or indirectly). The labeled antigen specific polypeptide bound to one or more cells in the blood sample is detected. The presence or absence of the label indicates the blood type. Thus, for example, using the antigen specific polypeptide that binds the H determinant, the presence of label in a blood sample indicates an O blood type. Similarly, the presence of label when an A determinant-specific polypeptide is used indicates either A or AB blood type. The presence of label when a B determinant-specific polypeptide is used indicates either B or AB blood type. One or more antigen specific polypeptides can be used with the same blood sample. Optionally, different labels can be attached to each antigen specific polypeptide if they have a different specificity. Accordingly, an FITC label could be linked directly or indirectly to the VLR that selectively binds an H determinant, whereas fluorescent labels that fluoresce at different wavelengths can be linked directly or indirectly to a VLR that selectively bind an A or B determinant.

Thus, provided herein is a method of typing blood comprising contacting a blood sample with a first antigen specific polypeptide, wherein the first antigen specific polypeptide is detectably labeled with a first label and wherein the first antigen specific polypeptide is specific for a first blood determinant; contacting the blood sample with a second antigen specific polypeptide, wherein the second antigen specific polypeptide is detectably labeled with a second label and wherein the second antigen specific polypeptide is specific for a second blood determinant; and detecting labeled first and second antigen specific polypeptides bound to one or more cell in the blood sample, the presence or absence of the first and second labels indicating the blood type.

Also disclosed are VLRs that selectively binds an agent, such as a pathogenic agent, wherein the pathogen is a bacterium, and more particularly wherein the bacterium is *Bacillus anthracis*. More particularly, provided herein is an antigen specific polypeptide wherein the binding polypeptide specifically binds a *Bacillus anthracis* cell surface polypeptide, such as BclA. Even more particularly, the antigen binding polypeptide has the amino acid sequence of SEQ ID NO: 5 (see FIG. 7) or SEQ ID NOs:22, 47, 49, 51, 53, 55, 57, 59 or 61. Also provided are nucleic acids that encode SEQ ID NOs:5, 22, 47, 49, 51, 53, 55, 57, 59 or 61, including, for example, SEQ ID NOs:21, 23, 46, 48, 50, 52, 54, 56, 58 and 60, respectively.

Numerous methods of using antigen binding polypeptides that are selective for pathogens are provided. Pathogens include any known pathogens such as, for example, bacteria and viruses. By way of example, provided herein is a method of detecting the presence of *Bacillus anthracis* in a sample, comprising contacting the sample with the antigen specific polypeptide that binds *Bacillus anthracis*, wherein the antigen specific polypeptide is detectably labeled. The labeled antigen specific polypeptide bound to the sample is detected and the presence of the label indicates the presence of *Bacillus anthracis* in the sample. Further provided is a method of reducing the pathogenicity of *Bacillus anthracis* in a subject comprising administering to the subject the antigen specific polypeptide that binds *Bacillus anthracis*.

Also, provided herein is a method of detecting the presence of a virus in a sample, comprising contacting the sample with the antigen specific polypeptide that binds the virus wherein the antigen specific polypeptide is detectably labeled. The labeled antigen specific polypeptide bound to the sample is detected and the presence of the label indicates the presence of virus in the sample. Further provided is a method of reducing the pathogenicity of a virus in a subject comprising administering to the subject the antigen specific polypeptide that binds the virus. The virus can be, for example, HIV or influenza. The antigen specific polypeptide can bind to, for example, HIV envelope protein gp120.

A method of removing a pathogen from a subject's blood sample or other biological fluid (e.g., cerebral spinal fluid) is also provided. The method comprises contacting the sample with an antigen specific polypeptide that selectively binds the pathogen. Further provided is a method of reducing the amount of a pathogen in a subject's blood comprising contacting a portion of the subject's blood with an antigen specific polypeptide that selectively binds the pathogen. Optionally, the blood to be contacted is removed and then returned to the subject. Optionally, the antigen is bound to a solid support.

Also provided herein are methods of making antigen specific proteins having a selected antigen specificity and compositions useful in these methods comprising administering to a lamprey or hagfish one or more target antigens (e.g., a target carbohydrate, a target protein, a target pathogen, a target glycoprotein, a target lipid, a target glycolipid, a target cell and any combination thereof including, for example, two carbohydrates, one carbohydrate and one protein, etc.). By way of example, provided herein is a method of making an antigen specific protein that binds a blood group determinant comprising administering to a lamprey or hagfish the blood group determinant; isolating an antigen specific protein-encoding RNA from lymphocytes of the lamprey or hagfish; amplifying antigen specific protein encoding cDNA from the isolated RNA; cloning the cDNA into an expression vector; expressing the expression vector in a bacterium transformed with the expression vector; isolating a cDNA clone; transfecting a cultured cell with a the cDNA clone; screening the culture supernatant for an ability to bind the blood group determinant, and isolating the antigen specific protein from the supernatant that binds the blood determinant. Alternatively, the erythrocyte itself, for example type O human erythrocytes, can be administered to the lamprey or hagfish to generate antigen specific proteins.

By way of another example, VLRs that specifically bind a pathogen like *Bacillus anthracis* can be made by administering to a lamprey or hagfish a cell surface *Bacillus anthracis* polypeptide isolating an antigen specific protein-encoding RNA from lymphocytes of the lamprey or hagfish; amplifying antigen specific protein encoding cDNA from the isolated RNA; cloning the cDNA into an expression vector; expressing the expression vector in a bacterium transformed with the expression vector; isolating a cDNA clone; transfecting a cultured cell with a the cDNA clone; screening the culture supernatant for an ability to bind the cell surface *Bacillus anthracis* polypeptide, and isolating the antigen specific protein from the supernatant that binds the cell surface *Bacillus anthracis* polypeptide. Alternatively, the pathogen itself, for example the *Bacillus anthracis*, can also be administered to the lamprey or hagfish to generate the antigen specific protein.

VLRs that specifically bind a pathogen such as, for example, a virus, like HIV or influenza, can be made by administering to a lamprey or hagfish a viral antigen; isolating an antigen specific protein-encoding RNA from lymphocytes of the lamprey or hagfish; amplifying antigen specific protein encoding cDNA from the isolated RNA; cloning the cDNA into an expression vector; expressing the expression vector in a bacterium transformed with the expression vector; isolating a cDNA clone; transfecting a cultured cell with a the cDNA clone; screening the culture supernatant for an ability to bind the antigen, and isolating the antigen specific protein from the supernatant that binds the antigen. As used herein a viral antigen includes the virus, a virus-like particle, a fragment of the virus, a polypeptide expressed by the virus or any other portion or part of the virus that stimulates an antigenic response in the lamprey or hagfish.

The methods of making the antigen specific polypeptides, as well as fragments and variants thereof, include making a stable cell line that expresses the nucleic acid that encodes the antigen specific polypeptide or fragment or variant thereof. Stable cell lines can be produced by a variety of methods. For example, stable cell lines can be produced by transfecting cells with expression vectors that co-express a VLR cDNA and a selectable marker, such as a gene that encodes for resistance to antibiotics. In the case of antibiotic selection, cells that stably integrate the expression vector into their genome will be resistant to antibiotics selection and survive, while other cells will die upon treatment with the antibiotic. Sub-clones may be established of cells that exhibit the highest levels of VLR secretion by such methods as limiting dilution cloning. Thus, provided herein are methods of making the antigen specific polypeptides by culturing cells of the stable cell line under conditions that allow the cells to express the antigen specific polypeptide and isolating the antigen specific polypeptide from the cells or culture medium.

Isolated populations of VLR producing lymphocytes are also provided. As used herein, VLR producing lymphocytes, VLR cells and VLR lymphocytes are used synonymously. For example, an isolated population of VLR-B+ lymphocytes are provided. As discussed in the examples below, VLR-B+ lymphocytes express VLR-B transcripts and not VLR-A transcripts. Optionally, VLR-B+ lymphocytes express TCR-like, CD-4-like and/or TNFR14. VLR-A+ cells express VLR-A transcripts and not VLR-B transcripts. Optionally, the isolated population of VLR-A+ cells express CD45 and/or GATA. The isolated populations of cells can be obtained using routine experimentation, for example, by flow cytometry or using VLR-B or VLR-A specific antibodies. A isolated population of antigen specific VLR-B+ cells are also provided. As used herein, the phrase antigen specific VLR-B+ cells refers to cells that express an antigen specific polypeptide. Such cells can be produced, for example, by immunizing a lamprey or hagfish with antigen and isolating the VLR-B+ cells by flow cytometry or using VLR-B specific antibodies, such as those provided herein, for example, 4C4 or 6C3. VLR-A+ cells can be similarly isolated.

Provided herein are nucleic acids (including, for example, isolated nucleic acids and including RNA and DNA) that encode antigen specific proteins. Nucleic acids that can encode the VLRs or regions thereof as well as variants and fragments of disclosed VLRs are disclosed herein. Nucleic acids that can encode VLRs include, but are not limited to, SEQ ID NOs:21, 23, 45, 46, 48, 50, 52, 54, 56, 58, 60 and 32. Nucleic acids that can encode LRRNTs include, but are not limited to,
SEQ ID NO:24 (TGTCCCTCGCAGTGTTCGTGT),
SEQ ID NO:25 (TGTCCCTCGCGGTGTTCGTGT),
SEQ ID NO:26 (TGTCCCGCGCAGTGTTCGTGT),
SEQ ID NO:27 (TGTCCCTCGCAGTGTTTGTGT), and
SEQ ID NO:28 (TGTCCCTCGCAGTGTCCGTGT).
Nucleic acids that can encode LRRCTs include, but are not limited to SEQ ID NO:29 (ACCAATACCCCCGTCCGT-GCGGTCACCGAGGCCAGCACTAGCCCCTCGAA ATGCCCA). Examples of nucleic acids include all degenerate sequences related to a specific polypeptide sequence and variants and derivatives thereof. The nucleic acids provided herein include complements of the encoding sequence. Nucleic acids are provided that encode any one of SEQ ID NOs:5, 6, 20, 22, 47, 49, 51, 53, 55, 57, 59, 61 or any specific regions thereof, including, for example, LRRNT (e.g., nucleic acids that encode SEQ ID NOs: 9-15), LRR, LRCCT (e.g., nucleic acids that encode SEQ ID NOs: 16-19), or the connecting peptide. More specifically, provided herein is a nucleic acid comprising SEQ ID NOs:21, 23, 45, 46, 48, 50, 52, 54, 56, 58, 60 and 32 or degenerate variants or complements thereof.

Also provided are isolated nucleic acids comprising a sequence that hybridizes under highly stringent conditions to all or any portion of SEQ ID NOs:21, 23, 45, 46, 48, 50, 52, 54, 56, 58, 60 or 32 or the complement of SEQ ID NOs:21, 23, 45, 46, 48, 50, 52, 54, 56, 58, 60 or 32. The hybridizing portion of the hybridizing nucleic acids is typically at least 15 (e.g., 20, 20, 40, or more) nucleotides in length. The hybridizing portion is at least 80% (e.g., 90% or 95%) identical to the a portion of the sequence to which it hybridizes. Hybridizing nucleic acids are useful, for example, as cloning probes, primers (e.g., PCR primer), or a diagnostic probe. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Assuming that a 1% mismatching results in a 1° C. decrease in Tm, the temperature of the final wash in the hybridization reaction is reduced accordingly (for example, if sequences having more than 95% identity are sought, the final wash temperature is decreased by 5° C.). In practice, the change in Tm can be between 0.5 and 1.5° C. per 1% mismatch. Highly stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. Salt concentrations and temperature can be varied to achieve the optimal level of identity between the probe and the target nucleic acid. Additional guidance regarding such conditions is readily available in the art, for example, in "Molecular Cloning: A Laboratory Manual," Third Edition by Sambrook et al., Cold Spring Harbor Press, 2001.

Also provided are nucleic acids having 80-99% identity (i.e., 80, 81, 82 . . . 99%) as compared to the nucleic acids sequences taught herein. Methods of determining percent identity are known in the art and are as described below in the context of amino acids.

Disclosed are compositions including primers and probes, which are capable of interacting with the VLR gene, or comparable genes. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Examples of primers taught herein include, but are not limited to, 1) 5'-CCACCATGTGGATCAAGTG-GATCGCC-3' (SEQ ID NO:30) and 2) 5'-GA-GAGCTAGCTCAACGTTTCCTGCAGAGGGC-3' (SEQ ID NO:31). Such primers can also be used as hybridization probes as discussed above. Preferably, the first primer contains a consensus Kozak sequence ahead of the start codon for optimum translation. It is also preferably 5' phosphorylated such that the PCR product can be cloned into blunt-end restriction enzyme sites. Preferably, the second primer possesses a restriction enzyme site. The resulting PCR product can then be digested with restriction enzyme and cloned into the expression vector. Preferably, the restriction enzyme site in the second primer is an NheI restriction site, since these sites have not been found in any of the characterized VLRs to date.

Also provided are expression vectors comprising the nucleic acids that encode VLR or fragments or variants thereof. Optionally, these expression vectors further comprise an expression control sequence operably linked to the nucleic acid encoding the VLR or fragment or variant thereof. Thus, provided is a vector that comprises a nucleic acid that encodes an antigen specific polypeptide (e.g., nucleic acids that encode SEQ ID NOs:5 or 22). Further provided are cultured cells comprising the expression vectors. For example, provided herein is a cultured cell transfected with the vector or a progeny of the cell, wherein the cell expresses the antigen specific polypeptide or fragment or variant thereof. Suitable expression vectors include, but are not limited to, pLPCX and pIRES-PURO2 (both from Clontech Laboratories, Inc., Mountain View, Calif.). For example, the expression vector can include both a VLR encoding nucleic acid and an antibiotic resistance gene from the same transcript by utilizing an internal ribosome entry site (IRES) sequence. This allows for efficient selection of stable cell lines.

The VLRs described herein and made by the methods described herein can be modified and varied so long as the desired function is improved or maintained. Optionally, amino acids located on the concave surface of a VLR are modified. For example, VLR5 (SEQ ID NO:6) can be modified, for example, to improve avidity by site-directed mutagenesis or affinity maturation. Variants of VLR5 with improved avidity are provided. Variants of VLR5 with increased avidity include, for example, VLR5$^{Y55R}$, VLR5$^{W127Y}$ and VLR5$^{Y55R/W127Y}$. Other VLRs can be similarly modified using the methods provided herein. Methods of making and screening multiple variants include, for example, in vitro affinity maturation using phage, yeast, bacterial or ribosome display techniques.

It is understood that one way to define any known variants and derivatives or those that might arise, of the disclosed genes and polypeptides herein is through defining the variants and derivatives in terms of identity to specific known sequences. For example, specifically disclosed are VLR variants that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to a stated sequence. Those of skill in the art readily understand how to determine the percent identity of two proteins or nucleic acids, such as genes. For example, the identity can be calculated after aligning the two sequences so that the identity is at its highest level.

Another way of calculating percent identity can be performed by published algorithms. Optimal alignment of sequences for comparison may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. U.S.A. 85:2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of percent identity can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment and calculation of percent identity. It is understood that any of the methods typically can be used and that in certain instances the results of these various methods may differ, but the skilled artisan understands if identity is found with at least one of these methods, the sequences would be said to have the stated identity or similarity.

For example, as used herein, a sequence recited as having a particular percent identity to another sequence refers to sequences that have the recited identity as calculated by any one or more of the calculation methods described above. For example, a first sequence has 80 percent identity, as defined herein, to a second sequence if the first sequence is calculated to have 80 percent identity to the second sequence using the Zuker calculation method even if the first sequence does not have 80 percent identity to the second sequence as calculated by any of the other calculation methods.

VLR variants and derivatives can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the polypeptide, thereby producing DNA encoding the variant, and thereafter expressing the DNA in recombinant cell culture. Techniques for making substitution mutations at predetermined sites in DNA having a known sequence are well known, for example, M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 1 which shows conservative substitutions.

TABLE 1

Amino Acid Substitutions.

| Original Residue | Exemplary Substitutions |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Gln, Asn |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatives are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton (1983) Proteins: Structure and Molecular Properties, W. H. Freeman & Co., San Francisco pp 79-86), acetylation of the N-terminal amine and, in some instances, amidation of the C-terminal carboxyl.

Provided herein are antibodies that selectively bind antigen specific polypeptides or VLRs or that selectively bind fragments or variants of antigen specific proteins or VLRs. Such antibodies can be used to, for example, to localize VLRs or VLR producing cells. Such antibodies can be indirectly or directly detectably labeled as discussed in more detail below. Such antibodies include, by way of example, antibodies that selectively bind the stalk region or a portion thereof, The antibodies can be monoclonal or polyclonal. Monoclonal antibodies may be prepared using hybridoma methods, such as those described by Kohler and Milstein, Nature, 256:495 (1975) or Harlow and Lane (1988) Antibodies, A Laboratory Manual. Cold Spring Harbor Publications, New York. The immunizing antigen can be an antigen specific polypeptide or any fragment (including for example, the stalk region) or variant thereof.

The monoclonal antibodies secreted by the clones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography. A variety of immunoassay formats may be used to select antibodies that selectively bind antigen specific polypeptides or fragments or variants thereof. For example, solid-phase ELISA immunoassays are routinely used to select antibodies selectively immunoreactive with target. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Further provided are chimeric antibodies, single chain antibodies, and hybrid antibodies (e.g., with dual or multiple antigen or epitope specificities), antibody conjugates and antibody fragments (such as F(ab')2, Fab', Fab and the like, including hybrid fragments) that selectively bind antigen specific polypeptides.

The VLRs and antibodies to VLRs may be directly or indirectly linked to a detectable tag or label. A detectable tag or a label is any tag that can be visualized with imaging or detection methods, in vivo or in vitro. The detectable tag can be a radio-opaque substance, radiolabel, a chemiluminescent label, a fluorescent label, or a magnetic label. The detectable tag can be selected from the group consisting of gamma-emitters, beta-emitters, and alpha-emitters, gamma-emitters, positron-emitters, X-ray-emitters and fluorescence-emitters. Suitable fluorescent compounds include fluorescein sodium, fluorescein isothiocyanate, phycoerythrin, and Texas Red sulfonyl chloride, Allophycocyanin (APC), Cy5-PE, CY7-APC, and Cascade yellow. Optionally the detectable tag can be visualized using histochemical techniques, ELISA-like assays, confocal microscopy, fluorescent detection, cell sorting methods, nuclear magnetic resonance, radioimmunoscintigraphy, X-radiography, positron emission tomography, computerized axial tomography, magnetic resonance imaging, and ultrasonography.

The label or tag may be directly bound to the VLR or antibody or, alternatively, the label or tag may be indirectly linked using a molecule or other agent that is directly linked to the label. For example, the VLR or antibody may be biotinylated and a subsequent detectable label like a fluorescently labeled strepavidin could be added to bind the biotin. Biotin is detected by any one of several techniques known in the art. For example, the biotin is detectable by binding with a fluorescence-labeled avidin and the avidin is labeled with a phycoerythrin or a catenated fluorescent label to increase the signal associate with each binding event.

Optionally, the antigen specific polypeptides or VLRs, or fragments or variants thereof, or antibodies to the antigen specific polypeptides or VLRs are bound to a solid support or a mobile solid support such as a slide, a culture dish, a multiwell plate, column, chip, array or beads. An array includes one or more multiwell arraying means such as microplates or slides. A mobile solid support refers to a set of distinguishably labeled microspheres or beads. Preferably, the microspheres are polystyrene-divinylbenzene beads. Sets of microspheres marked with specific fluorescent dyes and having specific fluorescent profiles can be obtained commercially, for example, from Luminex Corporation (Austin, Tex.).

Also provided is a plurality of polypeptides, nucleic acids, or antibodies. The plurality can be a homogeneous or heterogeneous for a selected polypeptide, nucleic acid, or antibody. Optionally the LRRs of the polypeptides are highly variable across polypeptides. Thus, the plurality can include polypeptides with different binding specificities, based on the variability of the internal LRRs.

Also provided are kits that include a container with polypeptides (soluble or membrane bound form), nucleic acids, or antibodies or a stable or mobile solid support with polypeptides, nucleic acids, or antibodies attached.

The polypeptides and nucleic acids can be used in a variety of techniques. For example, the polypeptides can be used to detect a selected agent, to block the activity of a selected agent, to purify an agent, as an imaging tool, and as a therapeutic agent.

Provided herein are composition comprising the polypeptides or nucleic acids and a pharmaceutically acceptable carrier. The compositions can also be administered in vivo. The compositions may be administered orally, parenterally (e.g., intravenously), by intramuscular injection, by intraperitoneal injection, transdermally, extracorporeally, topically or the like. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands.

By pharmaceutically acceptable is meant a material that is not biologically or otherwise undesirable, i.e., the material may be administered to a subject, along with the polypeptide, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable carriers and their formulations are described in Remington: *The Science and Practice of Pharmacy* (21st ed.) ed. David B. Troy, publ. Lippicott Williams & Wilkins 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

The variable lymphocyte receptors and variable lymphocyte receptor fragments and variants can also be administered to patients or subjects as a nucleic acid preparation (e.g., DNA or RNA) that encodes the variable lymphocyte receptor or variable lymphocyte receptor fragment or variant, such that the patient's or subject's own cells take up the nucleic acid and produce and secrete the encoded variable lymphocyte receptor or variable lymphocyte receptor fragment.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, Wolff, J. A., et al., *Science*, 247, 1465-1468, (1990); and Wolff, J. A. *Nature*, 352, 815-818, (1991). Transfer vectors can be any nucleotide construction used to deliver nucleic acids into cells (e.g., a plasmid), or as part of a general strategy to deliver genes, e.g., as part of recombinant retrovirus or adenovirus (Ram et al. *Cancer Res.* 53:83-88, (1993)). As used herein, plasmid or viral vectors are agents that transport the disclosed nucleic acids, such as VLR into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a VLR is disclosed and discussed and a number of modifications that can be made to a number of molecules including the VLR are discussed, each and every combination and permutation of the VLR and the modifications that are possible are specifically contemplated unless specifically indicated to the contrary. Thus, if a class of molecules A, B, and C are disclosed as well as a class of molecules D, E, and F and an example of a combination molecule, A-D, is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed that are discussed throughout the application, it is understood that each of these additional steps can be performed with any specific embodiment or combination of embodiments of the disclosed methods, and that each such combination is specifically contemplated and should be considered disclosed.

As used herein, subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. As used herein, patient or subject may be used interchangeably and can refer to a subject with a disease or disorder. The term patient or subject includes human and veterinary subjects.

As used in the specification and the appended claims, the singular forms a, an and the include plural referents unless the context clearly dictates otherwise. Thus, for example, reference to a VLR includes mixtures of two or more VLRs, and the like.

As used herein the terms isolated or purified include compositions (e.g., a polypeptide, cell or nucleic acid) that are substantially free from materials with which the composition is normally associated in nature. The polypeptides, or fragments thereof, can be obtained, for example, by extraction from a natural source, by expression of a recombinant nucleic acid encoding the polypeptide (e.g., in a cell or in a cell-free translation system), or by chemically synthesizing the polypeptide.

Ranges may be expressed herein as from about one particular value, and/or to about another particular value. When such a range is expressed, another embodiment includes from the one particular value and/or to the other particular value. Similarly, when values are expressed as approximations, by use of the antecedent about, it will be understood that the particular value forms another embodiment. It will be further understood that the endpoints of each of the ranges are significant both in relation to the other endpoint, and independently of the other endpoint.

Optional or optionally means that the subsequently described event or circumstance may or may not occur, and that the description includes instances where said event or circumstance occurs and instances where it does not.

As used herein, polypeptide, protein, and peptide are used interchangeably to refer to amino acid sequences.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It is to be understood that the present compounds, compositions, articles, devices, and/or methods disclosed and described are not limited to specific synthetic methods, specific recombinant biotechnology methods unless otherwise specified, or to particular reagents unless otherwise specified, as such may, of course, vary.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1 VLRs that Specifically Bind *Bacillus anthracis*

Figures 3A, 3B, 3C:
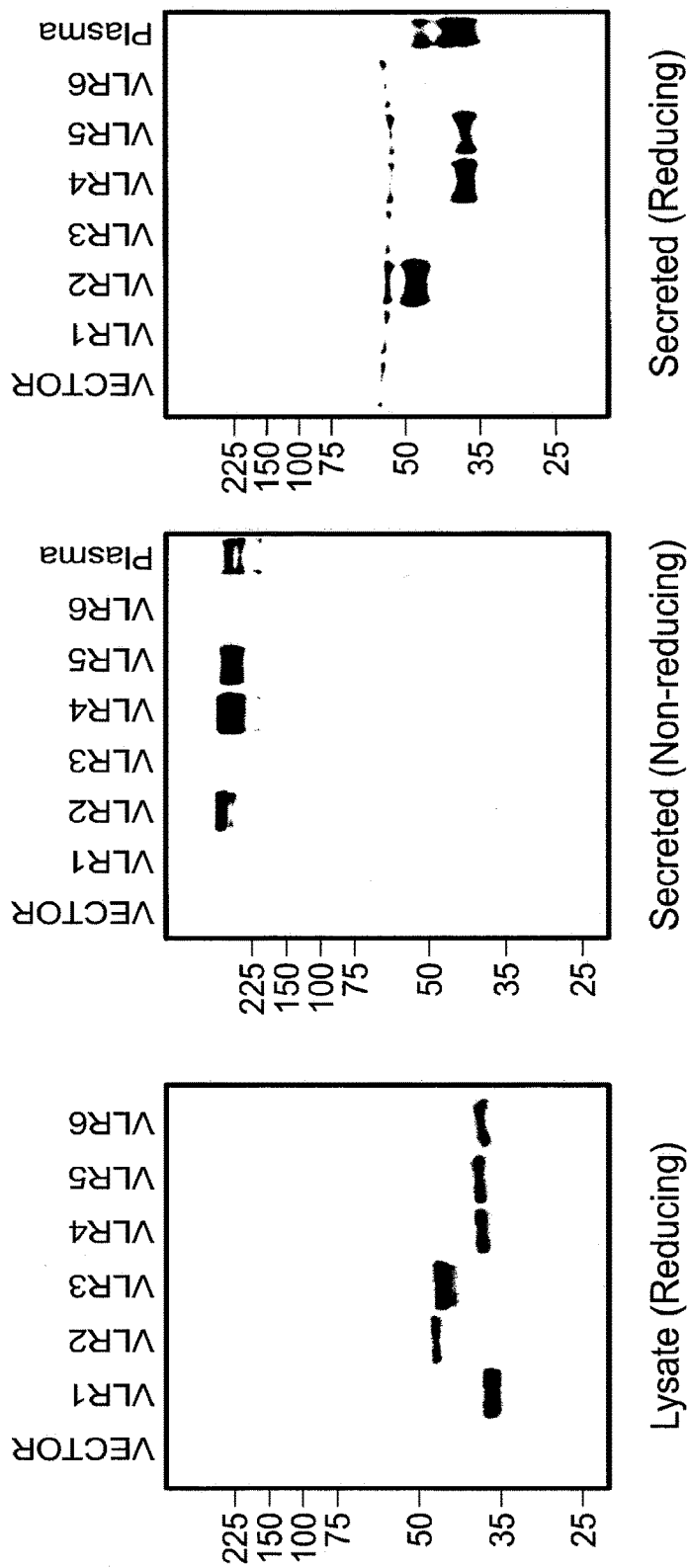
FIGS. 3A, 3B and 3C are Western blots of multimeric VLRs secreted from transfected HEK-293 cells.

VLR-positive lymphocytes from *Bacillus anthracis* exosporium immunized lamprey were harvested and their RNA isolated. Primers were used to amplify VLR cDNAs which were cloned into an expression vector and transformed into bacteria. Selected colonies were screened by PCR with VLR specific primers. The heterogeneous size of the PCR products indicated the diversity of the VLR cDNA library. Plasmids were purified from individual colonies and transfected into HEK-293 cells, which were tested for VLR expression by Western blotting of detergent-soluble cell lysates with anti-VLR mAb under reducing conditions. The first six VLRs expressed were composed of monomeric VLR units of different sizes (FIGS. 3A, 3B and 3C) due to variable numbers of their constituent LRR modules. When the culture supernatants of the transfected HEK-293 cells were examined for the presence of secreted VLRs, the products of three of these six VLR clones were secreted spontaneously. Under non-reducing conditions, the secreted VLRs are multimers with similar molecular weights to the VLR multimers found in lamprey plasma (FIG. 3B). In the presence of 2-mercaptoethanol, the secreted VLRs are reduced to monomers of about the same molecular weights as the lamprey plasma-derived VLR monomeric units (FIG. 3C). These transfection experiments have been repeated and VLR-2, -4, and -5 were detected in the culture supernatants, while VLR-1, -3, and -6 were not. DNA sequence analysis suggests a correlation between secretion and a peptide motif in the C-terminal LRR.

The secretion of recombinant VLRs into the culture medium of transfected HEK-293 allowed screening of VLR clones for antigen binding by ELISA. The C-terminal domain of BclA is the dominant epitope recognized by monoclonal antibodies derived from *B. anthracis* exosporium immunized mice. BclA is also recognized by polyclonal VLRs in the plasma of immunized lamprey. Therefore, ELISA plate wells were coated with the following antigens: purified recombinant BclA-CTD, wild-type *Bacillus anthracis* spores, BclA-deficient *Bacillus anthracis* spores, and spores from *Bacillus cereus* whose BclA-CTD differs by 15 (out of 134) amino acids from the BclA-CTD of *Bacillus anthracis*. The supernatant of VLR4 transfected HEK-293 cells reacted specifically with recombinant BclA-CTD and wild-type *B. anthracis* spores (FIG. 4). VLR4 does not recognize BclA-deficient *B. anthracis* spores or the *B. cereus* BclA protein that has extensive homology to *B. anthracis* BclA (FIG. 4).

Remarkably, VLR4 and VLR5 differ by only twenty amino acids, even though the former recognizes BclA-CTD and the latter does not (FIG. 5A). Amino acid differences are noted at positions predicted to be located on the inner surface of the VLR solenoid structure and to have been selected for during evolution (Alder, et al., Science 310: 1970, 2005). The VLR-4 transfected HEK-293 cells express both membrane-bound VLR and secreted VLR multimers (FIG. 1A).

Example 2 VLRs that Specifically Bind H Blood Group Determinant

Figures 5B, 6:
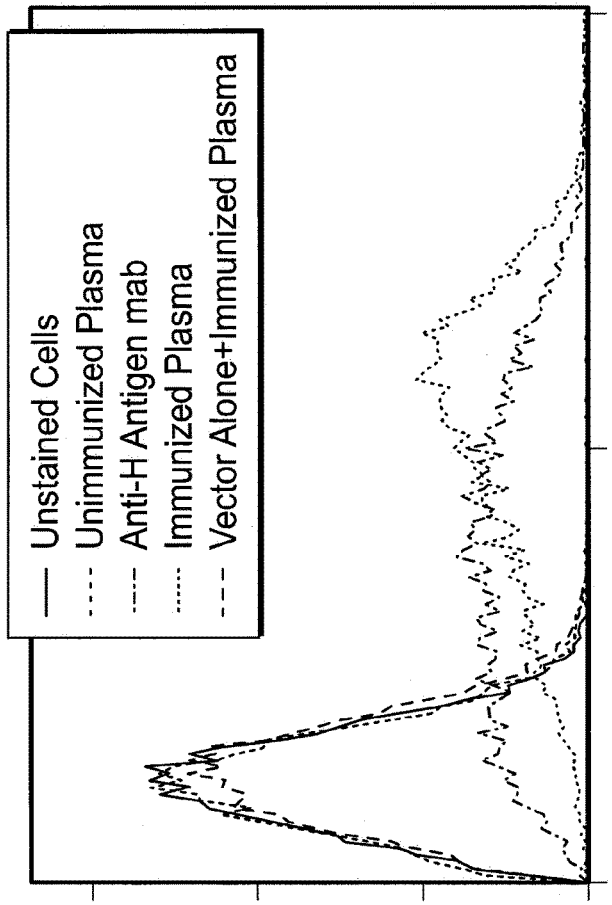
FIG. 5A is an alignment of B. anthracis (SEQ ID NO: 1) and B. cereus (SEQ ID NO:2) BclA-CTD amino acid sequence. Non-conserved residues are ences, San Jose, Calif.)).

Lampreys were immunized with $1\times10^7$ type O human erythrocytes once a week for four weeks. One week following the last immunization, lamprey plasma was collected. Two CHO cell lines were also employed, one transfected with α1,2-fucosyltransferase to produce the H antigen on the surface of CHO cells and the other transfected with the vector alone (Prieto et al., J Biol. Chem. 1997 Jan. 24; 272(4):2089-97.) Cells were first incubated in 1:10 dilution of lamprey plasma or 1:50 of the monoclonal antibody 92 FR A2, which is specific for the H antigen. All cells were washed and those cells incubated with lamprey plasma were then incubated in mAb 4C4 which recognized VLR molecules and then washed. All cells were stained with a goat anti mouse-RPE secondary antibody and then washed twice. FACS histogram shows that only plasma from lamprey immunized with human erythrocytes stained CHO cells transfected with the enzymes to produce the H antigen (FIG. 6). Thus, the lamprey VLR recognized carbohydrate antigens.

Example 3 Production and Characterization of Lamprey Monoclonal VLR-B Antibodies of Defined Antigen Specificity Isolation of Antigen Specific VLR-B Clones.

To surmount the constraints for culturing VLR-producing lamprey cells or hybridomas, a heterologous expression system was developed utilizing HEK-293T cells transfected with full-length VLR-B cDNAs, which spontaneously secrete recombinant oligomeric VLR-B antibodies into the tissue culture supernatant. The secretion of VLR-B clones by HEK-293T cells provided the means to screen a large number of clones for antigen binding using a methodology similar to hybridoma screening. The procedure enables antigen specific VLR-B clones to be isolated utilizing techniques accessible to biological laboratories and requires a time investment comparable to monoclonal antibody production (FIGS. 8A and 8B). Lamprey larvae were immunized every two weeks for a total of eight weeks before FACS isolation of VLR-B$^+$ lymphocytes from blood samples by FACS. RNA was isolated from sorted VLR-B$^+$ cells and VLR-B cDNA clones were amplified by PCR with primers specific for constant portions of the VLR-B transcript. The VLR-B cDNAs were cloned into a mammalian expression vector for transient transfection of HEK-293T cells. Tissue culture supernatants were then screened to identify clones that produced antigen-specific VLR-B antibodies by ELISA and flow cytometry.

Figures 9A, 9B:
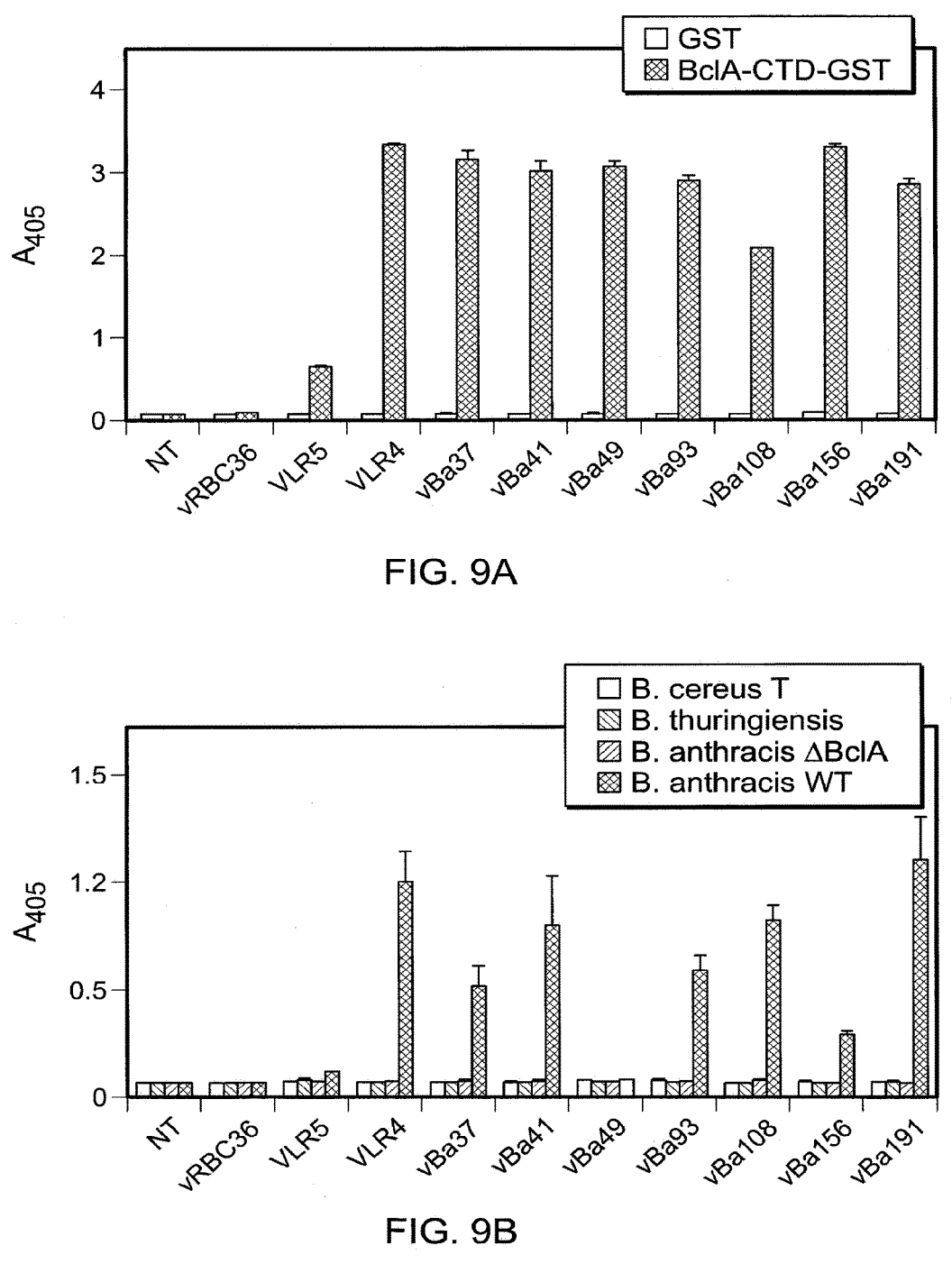

B. anthracis exosporium was chosen as the immunogen because as described herein the C-terminal domain (CTD) of the BclA spore coat protein is the immunodominant epitope recognized by VLR-B antibodies made in the in vivo response. HEK-293T cells in 24-well plates were transiently transfected with purified plasmid derived from a single bacterial colony so that every well represented a single VLR-B cDNA clone. When purified plasmids containing VLR-B cDNAs from B. anthracis exosporium-immunized lamprey were transfected in this manner and supernatants screened for BclA-CTD binding, 14 of the 212 clones (6.6%) secreted VLR-B antibodies that recognize BclA-CTD and not the GST control protein. Eight of the 14 antigen reactive clones recognized BclA-CTD at levels 10-fold above background (FIG. 9A). The specificity of these recombinant VLR-B antibodies was evaluated by testing for binding to B. anthracis and two closely related Bacillus species, B. cereus and B. thuringiensis. The VLR-B antibodies were found to react with B. anthracis spores, and not with B. cereus, B. thuringiensis, or BclA-deficient B. anthracis spores (FIG. 9B). Only one of the VLR-B antibodies that recognized the BclA-CTD recombinant protein (vBa49) did not recognize the B. anthracis spores. All of the recombinant VLR-B antibodies that reacted with the spores by ELISA also specifically recognized the B. anthracis spores in a flow cytometric immunofluorescence assay (FIG. 9C).

Figure 10A:
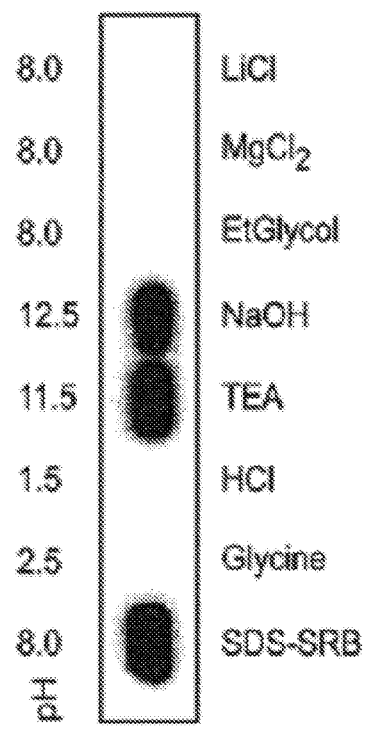
FIGS. 10A-D show that recombinant VLR-B is assembled into disulfide-linked multimeric complexes.
Figure 10B:
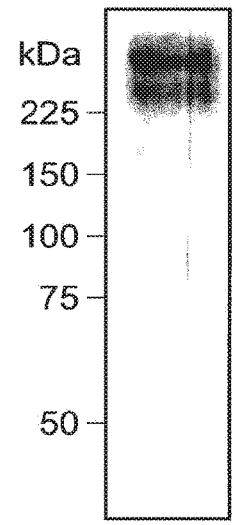
Figure 10C:
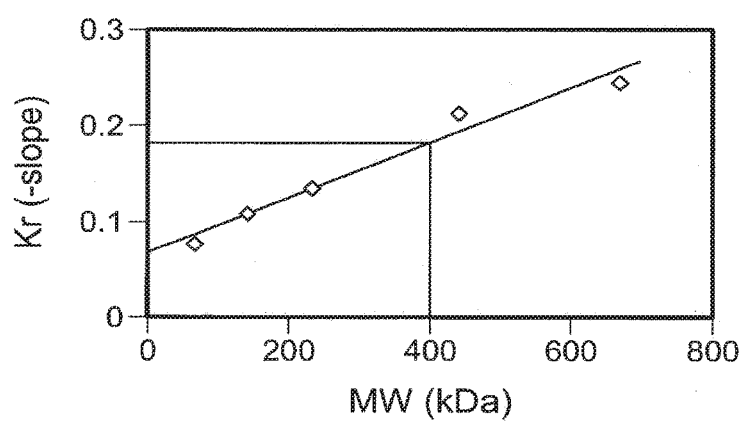
Figure 10D:
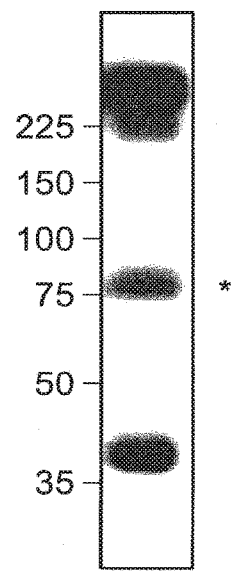

None of the seven recombinant VLR-B antibodies that recognized B. anthracis spores reacted with spores of closely related Bacillus species, even though, B. anthracis BclA-CTD differs from B. cereus BclA-CTD at only 14 of 134 amino acids positions, only nine of which are solvent exposed (FIG. 10D). Moreover, most of the BclA-CTD sequence disparities involve chemically similar amino acids. When the solvent-exposed amino acid differences were plotted onto the crystal structure coordinates of BclA-CTD, it was noted that the amino acid differences were dispersed over the face of the molecule, rather than being clustered. Since it is unlikely that the VLR-B antibody makes contact with all of the disparate amino acids, we conclude that the VLR-B antibodies can discriminate between related proteins on the basis of a few subtle amino acid variations.

VLR-B Antibody Purification by Antigen Affinity Chromatography.

The ease with which the VLR-B antibodies detected the BclA-CTD antigen by ELISA and immunofluorescence assays suggested the VLR-B antibody interaction with antigen would be of sufficient strength and stability to facilitate purification by affinity chromatography. Therefore, supernatant from the VLR-4 antibody-producing HEK-293T cell clone was incubated with sepharose beads covalently conjugated to BclA-CTD. Next, the conditions required to elute VLR4 from the BclA-CTD beads was tested using 5M LiCl, 3.5M MgCl$_2$, 0.1M glycine pH 2.5, 0.1M HCl, 50% ethylene glycol, 0.1M triethylamine pH 11.5, and 0.1M NaOH, pH 12.5. 0.1M triethylamine pH 11.5 and 0.1M NaOH pH 12.5 treatments were capable of dissociating VLR4 from the antigen-coated beads (FIG. 10A). By examining a gradient of pH conditions we found that pH≥11.0 was required to dissociate the recombinant VLR4 antibody from BclA-CTD. Having determined the optimal VLR4 binding and elution conditions, stable clones of VLR-4-secreting cells were selected and expanded to obtain larger quantities of the VLR-4 antibody, which was purified by BclA-CTD affinity chromatography and eluted with 0.1M triethylamine pH 11.5. The purified VLR4 antibody retained its ability to bind antigen despite the harsh elution conditions and was stored for >6 months at 4° C. in pH 7.2 MOPS-buffered saline without loss of antigen reactivity.

Two molecular weight forms of the VLR4 antibody eluted from the BclA-CTD affinity column, both of which were larger than 225 kDa standards on a non-reducing SDS-PAGE gel (FIG. 10B). Both protein bands were detected by western blotting with anti-VLR-B mAb (4C4) in the supernatant before purification and in the eluate from the antigen affinity column. To gain a more precise estimate of the molecular weight, the relative mobility of the recombinant VLR4 antibody and molecular weight standards were measured in native acrylamide gels (5, 6, 7, 8, 10, and 12%) and the data was used to construct Ferguson plots (FIG. 10C). By this method, the larger VLR4 band was shown to have a molecular weight of ~400 kDa. The molecular weight of the monomer was estimated to be 40 kDa, hence suggesting that the oligomer is composed of 10 subunits. Similarly, the lower molecular weight VLR4 oligomer was estimated to contain eight VLR subunits. A partially reduced band of ~80 kDa was observed on western blots of supernatants exposed to relatively low concentrations of reducing agents, which suggests the oligomeric VLR-B antibodies may be composed of dimeric subunits (FIG. 10D). From these findings, a model was generated in which the quaternary structure of lamprey VLR-B antibody is composed of a disulfide-linked pentamer or tetramer of dimers, much like IgM (FIG. 1B).

Analysis of VLR-B Antibody Assembly.

Figures 11A, 11B:
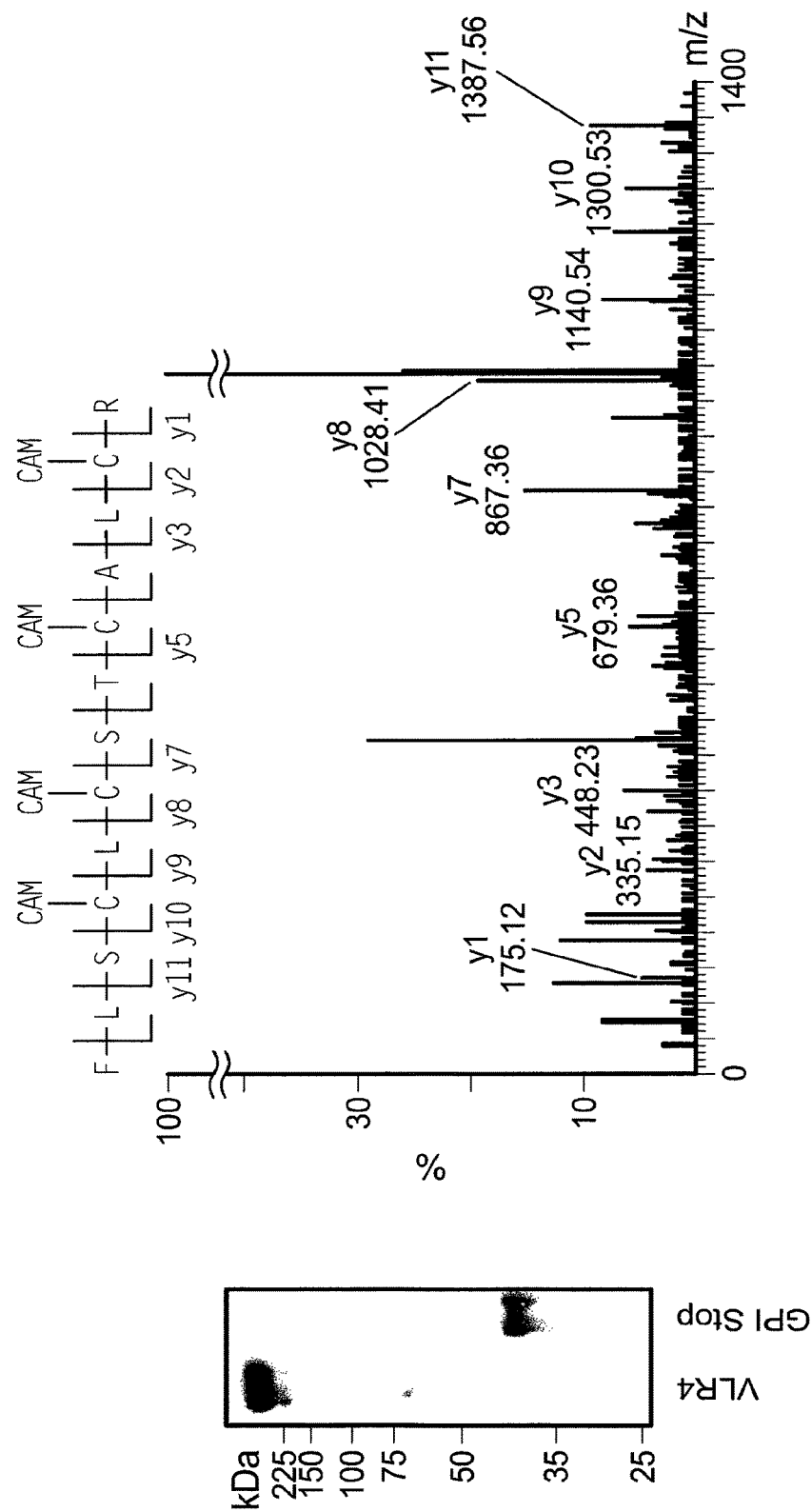
FIGS. 11A-D show that the cysteine-rich C-terminus of VLR-B is required for oligomer assembly.

VLR-B cell surface molecules are tethered to the lymphocyte surface by GPI-linkage. The plasmacytoid cells that secrete VLR-B antibodies also express cell surface VLR-B. If the GPI-linked VLR-B on the surface of the cell were liberated by a phospholipase, the cysteines used for oligomer formation should have to be located N-terminal to the GPI cleavage site, because amino acids C-terminal to the GPI cleavage site would be removed by GPI addition in the ER. To evaluate this issue, a construct encoding the VLR4 antibody from the start codon to the GPI cleavage site ($VLR4^{GPI-stop}$) was expressed in HEK-293T cells. The resultant wild-type VLR4 ($VLR4^{WT}$) and $VLR4^{GPI-stop}$ molecules were separated by non-reducing SDS-PAGE and their molecular weights were determined by western blotting with anti-VLR-B mAb (4C4). This analysis confirmed the $VLR4^{WT}$ molecular weight of >225 kDa, while the $VLR4^{GPI-stop}$ molecule migrated as a ~40 kDa monomer (FIG. 11A). This observation suggested that the cysteines that are used for VLR-B oligomerization are located C-terminal of the GPI cleavage site.

Figure 11C:
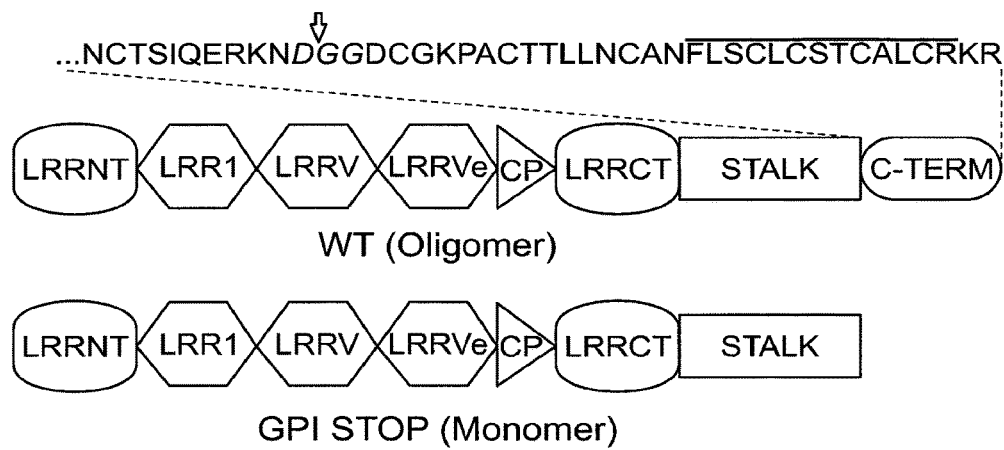

To determine whether the cysteine-rich C-terminus of secreted VLR4 is not removed by GPI cleavage during processing in the ER, the purified VLR4 antibody was separated by reducing SDS-PAGE and visualized by Gelcode Blue staining. This allowed the VLR4 antibody to be excised from the acrylamide gel before acetylated by iodoacetamide to prevent disulfide bond re-formation and digestion with trypsin. The trypsinized peptides were then separated by reverse phase chromatography for sequencing by MS/MS. This analysis revealed that the entire cysteine-rich peptide sequence was present in the C-terminus of the secreted form of the VLR4 antibody indicating that the multimeric VLR4 antibody is not derived from a GPI-linked precursor. The results of these experiments also indicate that the cysteines responsible for oligomer formation are located in the relatively hydrophobic C-terminus of the VLR-B antibody (FIGS. 11B and 11C).

Figure 11D:
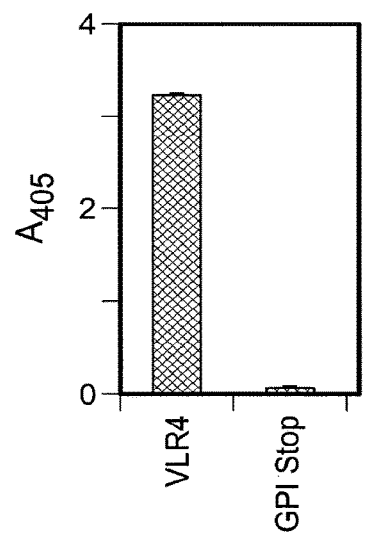

[The secretion of $VLR4^{GPI-stop}$ as a monomer allowed investigation of the contribution to antigen binding by the individual VLR4 antibody units. In this ELISA evaluation, BclA-CTD coated wells were incubated with supernatants containing the oligomeric VLR4 or monomeric $vLR4^{GPI-stop}$ antibodies. The oligomeric VLR4 antibody induced a strong binding signal, indicative of a tight interaction with BclA-CTD, while the monomeric VLR4 antibody form interacted with BclA-CTD to yield a barely detectable signal above the background (FIG. 11D). These composite results indicate that even when the antigen binding affinity for VLR-B monomeric units is relatively low, the antigen binding avidity of the oligomeric VLR-B antibody is relatively high.

VLR-B Antigen Binding Site.

The concave surface of VLR-B is composed of parallel β-strands, one each from LRR-NT, LRR1, LRR-V(s), LRRVe, and LRR-CP. The parallel β-strands of the concave surface have been proposed to be the antigen binding site because the highest sequence variability is observed there. Therefore, it was determined whether the amino acid residues responsible for antigen binding are located on the β-strands of the concave surface of VLR-B. The availability of multiple BclA-CTD specific VLR-B clones provided the means for this test using site directed mutagenesis. Four of the recombinant VLR-B antibodies against BclA-CTD exhibited high sequence identity. Three of these bind to BclA-CTD with high avidity (VLR4, vBA41, vBA191), while the other (VLR5) binds this antigen weakly. The weakly binding VLR5 antibody differs from the consensus sequence of the high avidity anti-BclA-CTD clones at six of the twenty possible hyper-variable amino acid positions on the concave surface (H34, Y55, T58, Q101, S103, W127) (FIGS. 12A and 12B). This finding suggests that one or more of these six amino acid residues are responsible for the decreased avidity of VLR5 and implied that VLR5 avidity could be increased by changing these residues to the corresponding amino acid utilized by the recombinant VLR-B antibodies with high binding avidity for the BclA-CTD antigen.

Figure 12C:
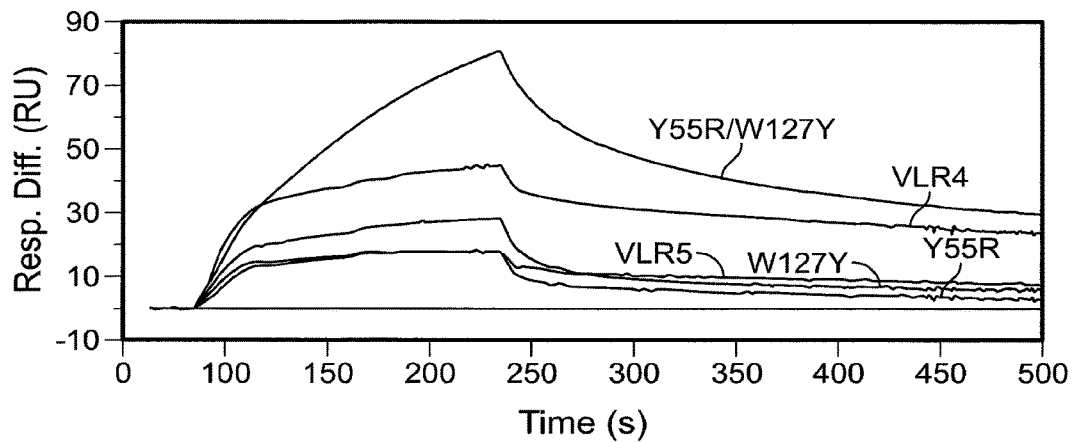

Surface Plasmon resonance was used to measure the relative binding avidities of VLR4, $VLR5^{wt}$, and the VLR5 antigen binding site mutants ($VLR5^{H34N}$, $VLR5^{Y55R}$, $VLR5^{T58I}$, $VLR5^{Q101H}$, $VLR5^{S103A}$, and $vLR5^{W127Y}$). This assay was conducted by flowing transfectant supernatants containing the various VLR-B antibodies over BclA-CTD covalently coupled to a Biacore chip. A heightened response, indicative of higher avidity binding to BclA-CTD, was evident for $VLR5^{Y55R}$ and $VLR5^{W127Y}$ relative to $VLR5^{wt}$ (FIG. 12C). The other mutant VLR5 antibodies displayed an equivalent or slightly weaker binding avidity than $VLR5^{wt}$ antibody.

Mutation of either antibody residues Y55 or W127, both of which are predicted to be aligned in the center of the VLR5 concave surface of VLR5 resulted in increased binding avidity of VLR5 (FIG. 12B). To test whether these residues could function cooperatively in antigen binding, a double mutant of VLR5 (Y55R/W127Y) was tested for binding to BclA-CTD by surface Plasmon resonance (FIG. 12C). Mutation of both Y55 and W127 resulted in increased binding avidity of VLR5.

Figure 13:
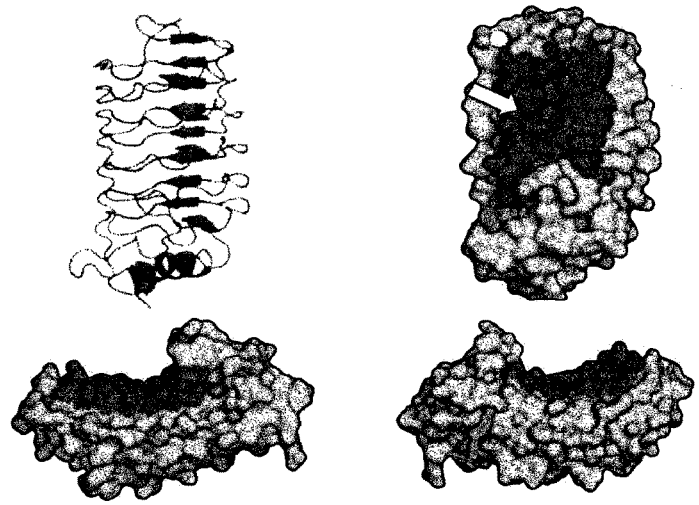
FIG. 13 is a model of anti-H antigen monoclonal VLR-B (vRBC-36 (SEQ ID NO:20)) antigen binding site. The vRBC-36 model was constructed by homology-based modeling to hagfish VLR-B (PDB ID: 2O6R) crystal structure data using SWISS-MODEL (http://swissmodel.expasy.org/). Hypervariable amino acid positions are highlighted dark grey. The arrow denotes a depression on the concave surface that is the likely contact surface of the fucose sugar that distinguishes the H antigen from other carbohydrate moieties.

A model of anti-H antigen monoclonal VLR-B (mVLR-B) (vRBC-36) antigen binding site was generated (FIG. 13). The vRBC-36 model was constructed by homology-based modeling to hagfish VLR-B (PDB ID: 2O6R) crystal structure data using SWISS-MODEL (http://swissmodel.expasy.org/). Hypervariable amino acid positions are highlighted purple. The red arrow denotes a depression on the concave surface that is the likely contact surface of the fucose sugar that distinguishes the H antigen from other carbohydrate moieties. Table 2 lists the amino acids encoded by the hypervariable residues of each LRR molecule.

TABLE 2

Amino acids encoded by hypervariable residues of anti-H antigen mVLR-B.

| LRR | Residues |
| --- | --- |
| LRRNT | SRDT (SEQ ID NO: 33) |
| LRR1 | DHYI (SEQ ID NO: 34) |
| LRRV | SGYE (SEQ ID NO: 35) |
| LRRV | TGDV (SEQ ID NO: 36) |
| LRRV | CCFE (SEQ ID NO: 37) |
| LRRVe | QDAH (SEQ ID NO: 38) |
| LRR-CP | GFYH (SEQ ID NO: 39) |

Example 4 VLR Antibody Responses in Jawless Vertebrates

Material and Methods:

Animal Maintenance and Immunization.

Sea lamprey larvae (11-15 cm) supplied by Lamprey Services (Ludington, Mich.) were maintained in sand-lined aquariums at 16-18° C. and fed brewer's yeast. Purified *Bacillus anthracis* exosporium, erythrocytes, LPS, or recombinant proteins were injected intraperitoneally into lamprey anesthetized by immersion in 0.1 g/L MS222 (Sigma, St. Louis, Mo.).

Monoclonal Anti-VLR Antibodies and Recombinant VLR Antibody.

Two mouse monoclonal antibodies were produced by hyper-immunization of mice with a recombinant VLR-B invariant stalk region protein produced in *E. coli* and subsequent fusion of regional lymph node cells with the non-productive Ag8.653 myeloma variant. Two hybridoma clones that produced antibodies with VLR-B specificity, 6C3 (IgM) and 4C4 (IgG2b), were identified by ELISA and flow cytometric screening. By immunofluorescence staining of viable cells and by immunohistochemical staining of fixed sections, the 6C3 and 4C4 antibodies were shown to recognize the same lymphocyte populations in lamprey blood and tissues. The 4C4 antibody was also reactive with VLR-B protein by Western blotting. A recombinant monoclonal VLR-B antibody (mVLR-RBC36) with human H antigen specificity was obtained by isolating RNA from the leukocytes of lamprey immunized with blood group O erythrocytes for production of cDNA with Superscript III (Invitrogen, Carlsbad, Calif.,). Primary and nested PCR was then carried out with primers specific for the VLR-B locus followed by cloning of PCR amplicons into the vector pIRESpuro2 (Clonetech, Mountain View, Calif.) and bacterial transformation. Plasmid DNA was isolated from single colonies (n=272) (Qiagen, Valencia, Calif.) before transfection into HEK 293T cells with LipofectAMINE (Invitrogen, Carlsbad, Calif.). Three days following transfection, supernatants from the HEK 293T cells were tested for H antigen specificity by their ability to stain CHO cells stably transfected with constructs for α1,2-fucosyltransferase, which produces the H antigen on the surface of the CHO cell.

Immunohistochemistry, Immunofluorescence and Electron Microscopy.

Lamprey were sacrificed by emersion in 1 g/L MS222 to obtain tissue and blood samples. For immunohistology, 1 cm corpse transections were fixed and embedded in paraffin. Cut sections were deparaffinized and rehydrated through sequential emersion in 100%, 95%, and 70% ethanol before antigen retrieval by heating the sections for 10 minutes at 15 psi in 0.01 M citric acid (pH 6) for the 6C3 anti-VLR antibody or in 0.01 M EDTA (pH 8) for 4C4 antibody staining. The sections were then treated with 3% hydrogen peroxide for five minutes before blocking with 3% goat serum for 30 minutes. Processed tissue sections were covered with one of the primary antibodies and incubated at room temperature for 1 hour before washing with Tris buffered saline and addition of a biotinylated secondary antibody and streptavidin-HRP (Signet Laboratories, Dedham, Mass.), 20 minutes each, followed by addition of the diaminobenzidine substrate (BioGenex, San Ramon, Calif.) for chromogenic labeling. Labeled slides were immersed briefly in Mayer's hematoxylin for counterstaining, then dehydrated through sequential baths of ethanol and xylene before application of cover slips. The same protocol was used for immunofluorescence, except that cover slips were placed after addition of the secondary antibody with Prolong Gold with DAPI mounting media (Invitrogen, Carlsbad, Calif.). For electron microscopy, sorted blood cells were resuspended in sodium cacodylate or Sorsenson's buffer with 2.5% glutaraldehyde for four hours at 4° C. Cells were then post-fixed in 1% osmium tetroxide for 1 hour, dehydrated in a series of graded acetone, and embedded in epoxy resin.

Antigens and VLR Antibody Assays.

BSA immunizations were injections of 10 µg of BSA in 50 µl of one of the following vehicles: sterile 0.66% PBS, 200 µg Al(OH)$_3$ absorbed with protein for four hours before injection, or emulsions with Ribi and Titermax Gold (Sigma, St. Louis, Mo.) adjuvants prepared according to manufacturer's protocol. For BSA coated beads, BSA was conjugated to 1 micron carboxylate polystyrene beads with the carbodiimide kit according to manufactures protocol (Polysciences, Warrington, Pa.) with lipopolysaccharide, lipoteichoic acid, and peptidoglycan (Invivogen, San Diego, Calif.) being added before injection. Erythrocytes were from B6 mice or human blood group 0 donors and were washed three times prior to injection. For antibody assays, washed erythrocytes ($5\times10^6$) mixed with lamprey plasma at varying dilutions were allowed to settle in conical bottom microwell plates for 1 hour before visual assessment of agglutination after tilting the plate at 80° C. for two minutes. ELISA assays were performed as previously described (Alder et al, *Science* 310:1970-3 (2005)). VLR reactivity with H antigen was determined by incubating CHO cells that were stably transfected with constructs for α1,2-fucosyltransferase or vector alone with test plasma samples. The CHO cells were then stained by incubation with 4C4 VLR mAb and goat anti mouse Ig (H+L)-RPE (Southern Biotech, Birmingham, Ala.) for 10 minutes each before analysis of immunofluorescence using a Cyan™ flow cytometer (Cytomation, Fort Collins, Colo.). For plasma VLR adsorption, test samples were mixed with the 4C4 anti-VLR mAb conjugated to sepharose or CHO cells ($3\times10^6$) fixed by paraformaldehyde for one hour at 4° C. Beads or cells were spun down and the supernatant transferred to a new test tube before repeating the adsorption process prior to the analysis of antigen reactivity by agglutination or western blot assays. For staining of lamprey lymphocytes with fluorescent spores, $4\times10^6$ leukocytes were mixed with 4C4 anti-VLR monoclonal antibody and $4\times10^6$ spores labeled with Alexa 488 (Invitrogen, Carlsbad, Calif.) on ice for 10 minutes. Cells were then washed and a goat anti-mouse Ig (H+L)-RPE was added for 10 minutes on ice before two washes. Flow cytometric analysis was then carried out on a Cyan™ cytometer (Cytomation, Fort Collins, Colo.).

ELISPOT Analysis of VLR Secreting Cells.

Microwells in 96 well plates (Millipore, Billerica, Mass.) were coated overnight at 4° C. with 100 µl of 50 µg/ml of recombinant BclA C-terminal domain protein (ref) then blocked with 1% BSA in PBS for 2 hours at 37° C. before adding test cell suspensions in IDMEM (Mediatech, Herndon, Va.) supplemented with 10% FBS, L-glutamine, penicillin, streptomycin, insulin, and transferrin for 18 hours at 25° C. in 5% CO2. The cells were then washed away with PBS before adding 1 µg/ml VLR antibody in 1% BSA for one hour at 37° C. After washing the wells with PBS-0.5% tween, goat anti mouse conjugated with horseradish peroxidase (Southern Biotech, Birmingham, Ala.) was added for one hour at 37° C. before washing the wells once with PBS-tween and three times with PBS. AEC peroxidase substrate (Moss Inc, Pasadena, Md.) was then added for one hour before washing with deionized water and counting of VLR antibody spots using Immunospot 2.0 software (Cellular Technology Ltd., Cleveland, Ohio).

Western Blots.

Plasma samples (1 μl) were electrophoresed on a 10% SDS page gel with or without 2-mercaptoethanol before transfer onto a nitrocellulose membrane which was blocked with 3% milk followed by incubation with the 4C4 anti-VLR mAb for one hour. The membranes were then washed 5 times with PBS-0.5% tween before adding goat anti-mouse HRP (Southern Biotech, Birmingham, Ala.) and a final wash one hour later. A SuperSignal chemiluminescent kit (Pierce, Rockford, Ill.) was used to detect VLR-antibody conjugates.

Quantitative PCR.

RNA was extracted from VLR-B+ and VLR-B− sorted cells using Trizol (Invitrogen, Carlsbad, Calif.) and RNeasy with the on-column DNA digestion (Qiagen, Valencia, Calif.) according to manufacturer's protocol. First strand cDNA was generated using random hexamer primers with Superscript III (Invitrogen, Carlsbad, Calif.). Quantitative PCR was carried out with primers designed at splice sites, when known, using SYBR Green on a 7900HT ABI Prism (Applied Biosystems, Foster City, Calif.).

Results.

Analysis of the VLR-B Antibody Response to a Model Protein Antigen.

The present examples employ VLR-B stalk region specific monoclonal antibodies 6C3 (IgM isotype) and 4C4 (IgG2b isotype) for detection of the lamprey VLR-B antibodies. Initially, relatively large sea lamprey larvae (~13 cm long) were immunized with soluble bovine serum albumin (BSA)(10 μg) either in unmodified form, alum precipitated, or combined with commercially available adjuvants, Ribi® (Ribi Immunochem Research, Inc., Hamilton, Mont.) and Titermax® (CytRx Corporation, Los Angeles, Calif.), both of which contain bacterial products in a water-in-oil emulsion. For other immunizations, BSA was conjugated to the surface of polystyrene beads, $1 \times 10^8$ of which were injected either alone or together with 1 μg each of lipopolysaccharide, lipoteichoic acid, or peptidoglycan. An immunization protocol was used that elicited a strong VLR humoral response to anthrax exosporium proteins: primary immunization followed by booster immunization two weeks later and collection of plasma samples for testing at four weeks. None of these methods of BSA immunization resulted in the production of VLR-B antibodies that could be detected by ELISA (n+30, 4-5 per immunization group). Moreover, the immunized lamprey did not respond with the lymphoblastoid transformation of circulating lymphocytes that was observed after hyperimmunizating lamprey with anthrax exosporium. BSA as a model protein immunogen thus failed to induce a VLR-B antibody response, even when given with adjuvants, in aggregated form or coated onto the surface of a solid matrix.

Lamprey Produce Agglutinating VLR-B Antibodies in Response to Mammalian Erythrocytes.

Figure 14A:
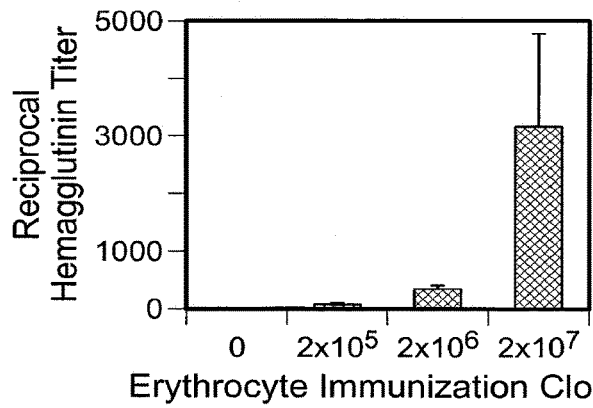
FIGS. 14A-D show the analysis of VLR-B antibodies produced after immunization with human blood group O erythrocytes.

To examine the possible role of VLR antibodies in the erythrocyte agglutinin response, lamprey were immunized intraperitoneally with either mouse or human erythrocytes. In accordance with previous reports, erythrocyte hemagglutinin responses were elicited that were antigen dose dependent and specific for the donor erythrocyte immunogen (FIG. 14A, Table 3).

TABLE 3

Specificity of the Agglutinin Response to Human or Mouse Erythrocytes.

| Erythrocyte Immunogen[a] | Reciprocal Erythrocyteagglutinin Titers | |
|---|---|---|
| | Human | Mouse |
| Human 1 | 400 | 0 |
| Human 2 | 800 | 0 |
| Human 3 | 1600 | 0 |
| Mouse 1 | 0 | 3200 |
| Mouse 2 | 0 | 1600 |
| Mouse 3 | 0 | 400 |

[a]Three lamprey larvae were immunized on days 0 and 14 with $1 \times 10^7$ human or mouse erythrocytes an dplasma samples were obtained on day 28.

Figure 14B:
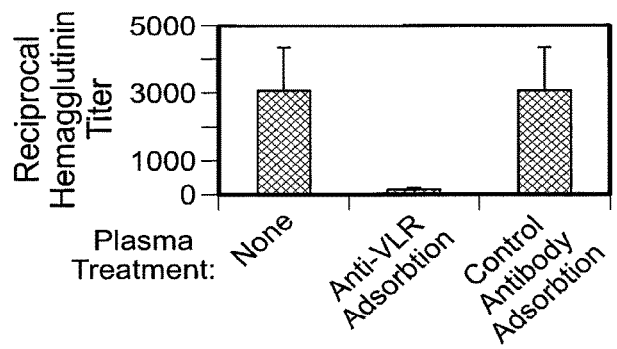

To determine whether the erythrocyte agglutination was mediated by VLR-B antibodies, sepharose beads coated with an anti-VLR-B antibody were used to remove VLR-B antibodies from the plasma samples. The adsorption with anti-VLR-B coated beads was found to remove the vast majority of the hemagglutinins, whereas adsorption with beads coated with a control antibody of irrelevant specificity had no demonstrable effect (FIG. 14B). These findings indicate that the hemagglutinins made by erythrocyte immunized lamprey are VLR-B antibodies.

Carbohydrate H Antigen Specificity of VLR-B Antibodies to Blood Group O Erythrocytes.

Figure 14C:
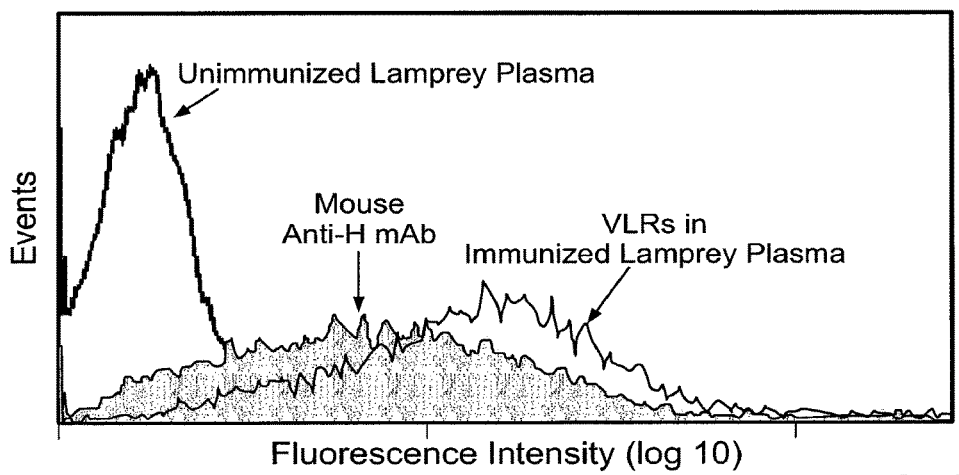
Figure 14D:
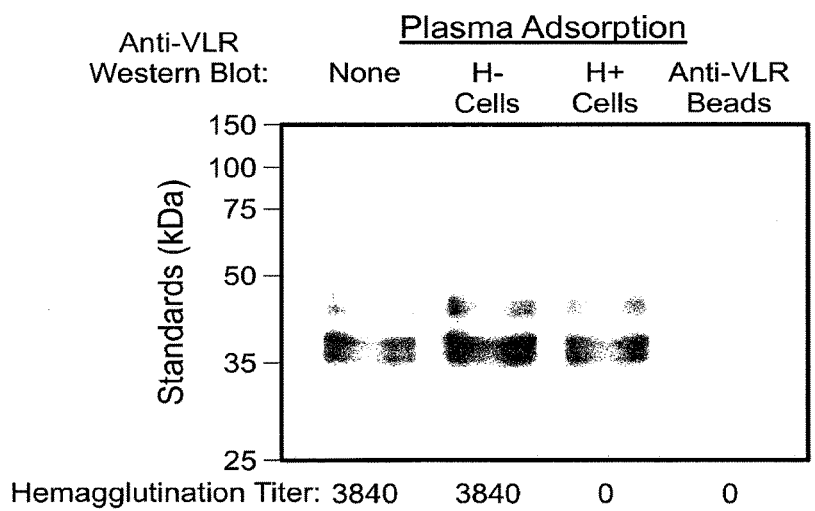

Earlier studies suggested the hemagglutinins made by lamprey that were immunized with human blood group O erythrocytes were specific for the H trisaccharide cell surface antigen that defines this blood type. To test for H antigen specificity of the VLR-B antibodies, CHO cells were employed that were stably transfected with the α1,2-fucosyltransferase enzyme that generates the H trisaccharide. Animals immunized with blood group O erythrocytes were shown to produce VLR-B antibodies that recognized CHO cells expressing the H trisaccharide antigen (FIG. 14C), while they did not produce VLR antibodies that recognized the control CHO cells that were transfected with the vector alone. Moreover, adsorption of the immune plasma samples with H antigen-positive CHO cells removed the agglutinating VLR antibodies without noticeably affecting the plasma level of the VLR-B antibody pool (FIG. 14D). These findings confirm that the H trisaccharide determinant is a dominant antigenic determinant in the lamprey response to blood group O erythrocytes. They also show that this humoral response is attributable primarily to the production of VLR-B antibodies and demonstrate that the VLR-B antibodies produced in respond to this antigen comprise only a minor portion of the circulating VLR-B antibody pool.

The H Antigen Specific VLR-B Antibodies are Disulfide-Linked Multimers.

The ability of VLR-B antibodies to agglutinate erythrocytes inferred their multivalence. To examine the composition of these antibodies, a recombinant VLR-B antibody with H antigen specificity was generated. For this purpose, a VLR-B cDNA library was prepared from blood leukocytes of immunized animals and individual VLR-B clones were transfected into HEK 293T cells. When the transfected cells were screened for clones producing antigen specific VLR-Bs, one clone was identified that produced a VLR antibody that reacted with H antigen+ CHO cells and not with H antigen− CHO cells (FIG. 15A). The antigen binding by this recombinant VLR antibody was inhibited by preincubation with soluble H antigen. Western blots analysis revealed that this VLR antibody is a large multimeric protein of >250 kDa that is composed by multiple individual VLR-B subunits of ~35 kDa linked together by disulfide bonds (FIG. 15B).

Dose Dependency and Antigen Specificity of the Anthrax VLR-B Antibody Response.

Figures 16A, 16B, 16C:
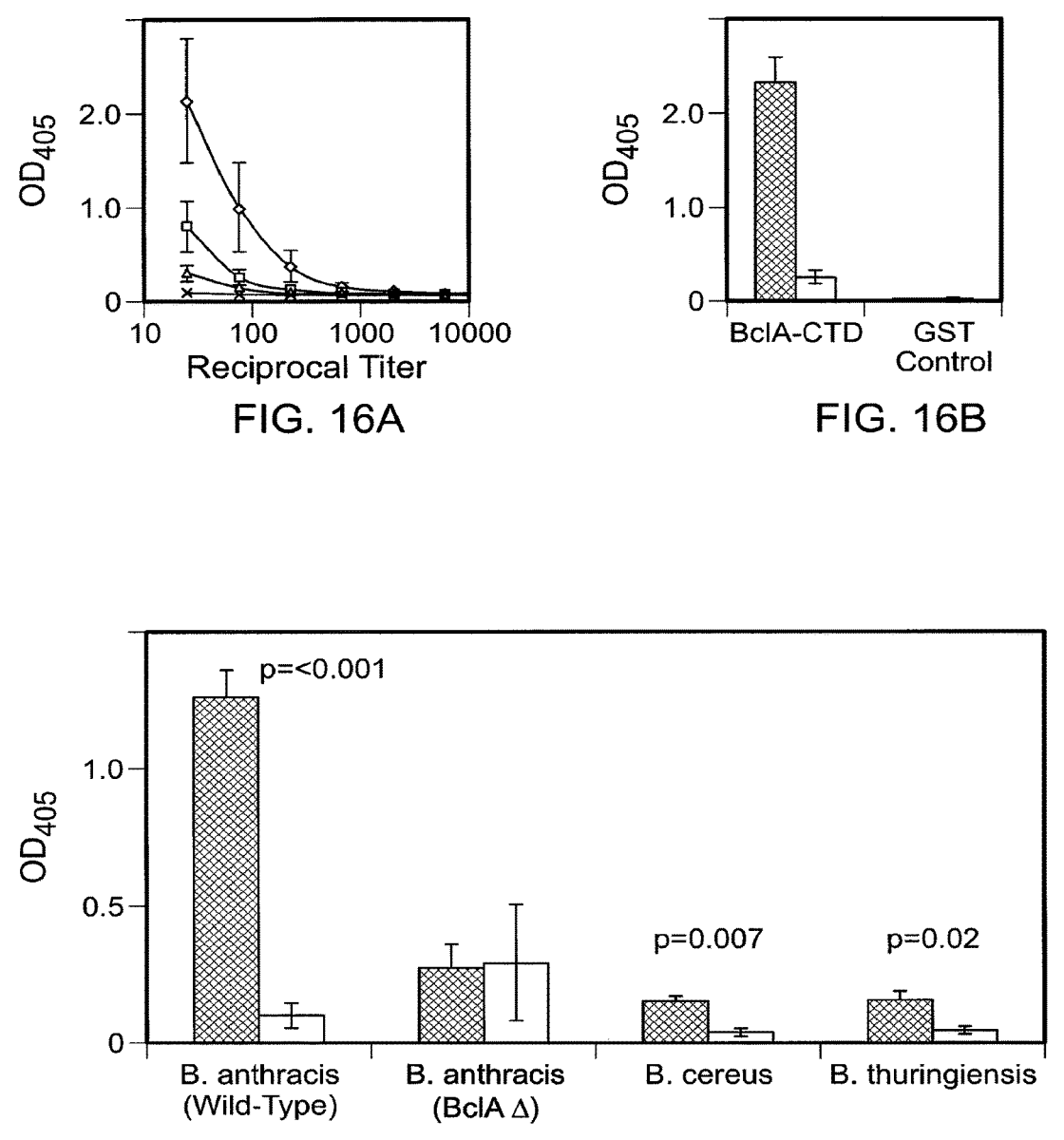

As described herein, lamprey immunized with *Bacillus anthracis* exosporium produced VLR antibodies against the spore surface protein BclA. This response was examined in order to define the antigen dosage requirement to elicit the VLR-B antibody response and to determine the epitope specificity. Increasing the immunogen dosage led to the production of higher titers of VLR-B antibodies to the BclA surface protein (FIG. 16A).

In view of the finding that anthrax immunized mice make antibodies mainly against the C-terminal domain (CTD) of BclA, the lamprey response to the BclA-CTD determinant was examined. The VLR-B antibodies produced by immunized lamprey were also found to be reactive with the BclA-CTD and not with a control protein (FIG. 16B). Moreover, the VLR-B antibody response appeared to be directed primarily against non-crossreactive determinants of *B. anthracis*, since only minimal reactivity was detected for the closely related *B. thuringiensis* and *B. cereus* spores (FIG. 16C). Notably, the BclA protein of *B. cereus* differs in only 10% of the amino acids from the BclA protein of *B. anthracis*. These observations indicate that the lamprey VLR response to anthrax exosporium is dose-dependent, highly specific, and focused primarily on the CTD determinant of the BclA surface protein.

Tissue Distribution of VLR-B$^+$ Lymphocytes in the Lamprey.

To examine the cellular basis for the lamprey humoral response to immunization, the tissue distribution of the VLR-B$^+$ cells was determined by immunohistochemical staining using the two antibodies that are specific for the invariant stalk region of VLR-B. Discrete localization of VLR-B$^+$ cells was observed using monoclonal 6C3 anti-VLR-B antibody in the kidney and typhlosole, two hematopoietic organs, as well as in the gills. VLR-B$^+$ lymphocytes were not detected in the epithelium of the intestine, which in the larval filter-feeding stage is a straight tube beginning near the last gill slit and terminating at the cloaca. Over most of its length, the intestine is folded like an elongated horseshoe over the typhlosole, which is comprised primarily by hematopoietic lineage cells lining the blood filled sinuses. The VLR-B$^+$ lymphocytes were found to be dispersed throughout the typhlosole, wherein they exhibited greater morphological diversity and variability in staining intensity than the VLR-B$^+$ lymphocytes in other tissues (FIG. 17A). Small VLR-B$^+$ cells were intermixed with other hematopoietic cells in the kidneys, which extend over most of the body length and flank the lateral and dorsal surfaces of the lamprey intestine. The VLR-B$^+$ lymphocytes were most abundant in the most ventral aspects of the kidneys. The gills displayed the greatest accumulation of VLR$^+$ lymphocytes in terms of the density of positively staining cells. The VLR-B$^+$ cells were especially abundant within the vessels located at the gill bases. The immunofluorescence staining pattern of these intravascular lymphocytes was suggestive of extensive intracellular VLR-B accumulation (FIG. 17B). VLR-B staining in the tissue sections was also consistently evident along the inner surface of blood vessels and sinuses, reflecting the abundant pool of circulating VLR-B antibodies, and was not evident in the intercellular spaces outside of the vasculature.

The distribution of VLR-B bearing cells was examined further by the staining of viable cells in fluid suspensions freshly prepared from the blood, kidney, and typhlosole. When light scatter characteristics were used to examine the lymphocyte-like cells by immunofluorescence flow cytometry, 15-35% of the blood cells in the 'lymphocyte gate' were VLR-B$^+$, ~50% were VLR-B$^+$ in the kidney cell suspensions, and 15-30% were VLR-B$^+$ in the typhlosole (FIG. 17C). The VLR-B$^+$ cells from blood and kidney consistently expressed relatively high VLR-B levels, whereas VLR-B$^+$ cells from the typhlosole exhibited greater variability and lower levels of cell surface VLR-B.

VLR-B$^+$ Lymphocyte Morphology and Gene Expression Profile.

The VLR-B$^+$ and VLR-W cells within the 'lymphocyte gate' were isolated by fluorescence activated cell sorting and examined by transmission electron microscopy. The VLR-B$^+$ cells in these studies resembled small lymphocytes in jawed vertebrates in that they have a relatively large nucleus, which contains a compacted chromatin concentrated in a peripheral pattern, surrounded by a narrow rim of cytoplasm that contains relatively few distinguishable organelles, such as mitochondria. In contrast, the vast majority of VLR-W cells in the 'lymphocyte gate' displayed thrombocyte morphology, which is characterized by a deep nuclear cleft and relatively abundant cytoplasm (FIG. 17D).

The isolated VLR-B$^+$ and VLR-B$^-$ populations of cells were also used to compare their gene expression profiles. In this analysis the purified VLR-B$^+$ cells were found to express VLR-B transcripts, and not VLR-A transcripts. Conversely, the VLR-W cells in the 'lymphocyte gate' expressed VLR-A and not VLR-B transcripts (FIG. 18). When the expression of other currently known genes that have potential links to lamprey immune cell function were compared, CD45 and GATA were found to be expressed at higher levels in the VLR-B-population, whereas the TCR-like, CD4-like, and TNFR14 genes were expressed at higher levels in the VLR-B$^+$ lymphocytes. These results indicate that the VLR-B$^+$ cells and VLR-A$^+$ cells represent distinct lymphocyte populations, confirm that lymphoid lineage cells preferentially express the TCR-like and CD-4-like genes and suggest that the TNFR14 gene may also be preferentially expressed by lymphocytes.

VLR-B$^+$ Lymphocyte Responses to In Vivo Antigenic Stimulation.

Immunization of lamprey with a cocktail of antigens and phytomitogens was shown to induce a global lymphoblastoid response. This type of lymphoblastoid response was reproduced by injecting the lamprey larvae with a large dose (>2 µg) of anthrax exosporium intraperitoneally (FIG. 19A). When blood cells from these animals were stained with the anti-VLR-B antibodies, most of large lymphoblastoid cells were found to be VLR-B$^+$, although the level of cell surface VLR-B was noticeably diminished (FIG. 19B). This result suggested that, given in sufficient dosage, the anthrax exosporium can serve as a mitogen for lamprey lymphocytes.

To evaluate the specific antigen response at a cellular level, the frequency of antigen binding cells was determined before and after immunization with anthrax exosporium. In these experiments, fluorescence labeled anthrax spores were used to detect antigen-binding VLR-B$^+$ cells. Whereas a small subpopulation of the VLR-B bearing lymphocytes (~1%) in naive animals were found to bind *B. anthracis* or *B. cereus* spores, a four-fold increase of *B. anthracis* binding VLR-B$^+$ cells was observed following immunization with *B. anthracis* exosporium (FIGS. 20A and 20B) and the frequency of *B. cereus*-binding cells was unchanged.

To identify cells that secrete the VLR-B antibodies in response to antigenic stimulation, the VLR-B$^+$ and VLR-B$^-$ subpopulations of cells from immunized lamprey were separated according to their light scatter characteristics and evaluated by ELISPOT assays for their ability to secrete VLR-B antibodies to the BclA-CTD antigen. Cells isolated from the blood, kidney and typhlosole were placed in culture for 18 hours before their evaluation for VLR-B antibody secretion. The cells which secreted BclA-CTD specific antibodies were found only among the VLR-B+ cells with the highest forward and side light scatter characteristics, a finding that indicated their relatively large cell size (FIG. 21A). When large VLR-B producing cells were isolated for evaluation by transmission electron microscopy, they were found to have plasmacytoid morphology featuring extensive cytoplasm with multiple organelles and an expanded network of rough endoplasmic reticulum (FIG. 21B). In a typical response to anthrax exosporium, four weeks after the first immunization, the VLR-B antibody secreting cells were most abundant in either the blood or the kidney and were less abundant in the typhlosole. These observations indicate that immunization with an effective immunogen induces antigen-specific lymphocytes to undergo lymphoblastoid transformation, proliferation, and differentiation into plasmacytoid cells that secrete antigen-specific VLR-B antibodies.

Example 5 Lamprey Produce VLR-B Antibodies in Response to Viral Immunization

For influenza virus, lamprey were immunized intraperitoneally with 25 µg of formalin fixed influenza virus diluted in 50 µl of ⅔ PBS. Two weeks later, the animals received a secondary injection with the same amount of immunogen. Plasma samples were collected two weeks after the secondary immunization and tested for reactivity.

ELISA assays were carried out by coating plates overnight at 4° C. with 10 µg/mL formalin killed influenza virus diluted in PBS. Purified adenovirus was used to coat plates as a control. Plates were then washed and blocked with 3% BSA. Detection of VLR-B antibodies was carried out using monoclonal anti-VLR-B (4C4) antibody followed by a secondary antibody with enzyme conjugate.

Viral neutralization activity was tested by hemagglutinin inhibition assays and plaque neutralization assays.

As shown in FIG. 23, lamprey immunized with influenza virus produce VLRs specific for immunogen.

Table 4 shows influenza virus hemagglutinin inhibition and neutralization titers for plasma from immunized and naive lamprey.

TABLE 4

|  | Hemagglutinin Inhibition Titers | Neutralization Assay Titers |
|---|---|---|
| Naïve 1 | <20 | <20 |
| Naïve 2 | <20 | <20 |
| Flu 1 | <20 | <20 |
| Flu 2 | <20 | 40 |
| Flu 3 | 40 | 40 |
| Flu 4 | 40 | 40 |
| Flu 5 | 160 | 160 |

For HIV virus, virus-like particles (VLPs) were injected intraperitoneally such that an equivalent of 25 µg of HIV envelope protein (Env) protein was administered. Animals received a booster immunization two weeks after the initial immunization. Two weeks after booster immunization, plasma was collected and reactivity of VLR-B antibodies to HIV was tested by ELISA assays.

For ELISA, plates were coated with 1 µg/mL soluble gp120 overnight at 4° C. Plates were then washed and blocked with 3% BSA. Detection of VLR was carried out using monoclonal anti-VLR-B (4C4) antibody followed by a secondary antibody with enzyme conjugate.

As shown in FIG. 24, lamprey immunized with HIV VLPs produce VLR-B antibodies specific for HIV envelope protein gp120 subunit.

These results demonstrate that immunization with formalin fixed influenza virus or HIV VLPs induces a potent immune response in lamprey resulting in the production of antigen specific VLR-B antibodies. In the case of influenza, the plasma from immunized animals inhibited agglutination of erythrocytes and plaque formation by live influenza virus in vitro studies. The gp120 subunit of the HIV envelope protein, which is the target of the VLR-B antibody response, is responsible for viral entry into host cells through interaction with CD4. Therefore, the interaction of the large (400 kDa) multivalent VLR-B antibodies with HIV gp120 is likely to block the interaction of HIV envelope proteins with CD4 and hence prevent viral entry.

It will be apparent to those skilled in the art that various modifications and variations can be made without departing from the scope or spirit of the compositions and methods described herein. Other embodiments will be apparent to those skilled in the art from consideration of the specification and practice of the compositions and methods disclosed herein.

What is claimed is:

1. A method of making a plurality of purified multimers comprising a plurality of soluble, monoclonal antigen specific polypeptides comprising
    a) isolating a cDNA clone encoding an antigen specific polypeptide, wherein the antigen specific polypeptide comprises an N-terminal leucine rich repeat (LRRNT), one or more leucine rich repeats (LRRs), a C-terminal leucine rich repeat (LRRCT), and a connecting peptide, wherein the connecting peptide comprises an alpha helix;
    b) transfecting a mammalian cell in culture medium with the cDNA clone of step (a); and
    c) isolating the plurality of multimers from the culture medium.

2. The method of claim 1, wherein the antigen specific polypeptides bind a target protein, a target carbohydrate or a target pathogen.

3. The method of claim 1, further comprising the step of generating a stable mammalian cell line comprising the cDNA clone.

* * * * *